US010736893B2

(12) United States Patent
Barf et al.

(10) Patent No.: US 10,736,893 B2
(45) Date of Patent: Aug. 11, 2020

(54) IMIDAZOPYRAZINE INHIBITORS OF BRUTON'S TYROSINE KINASE

(71) Applicant: Acerta Pharma B.V., Oss (NL)

(72) Inventors: Tjeerd Barf, Ravenstein (NL); Edwin de Zwart, Dreumel (NL); Saskia Verkaik, Macharen (NL); Niels Hoogenboom, Rijen (NL); Dennis Demont, Oss (NL)

(73) Assignee: Acerta Pharma B.V., Oss (NL)

( * ) Notice: Subject to any disclaimer, the term of this patent is extended or adjusted under 35 U.S.C. 154(b) by 0 days.

(21) Appl. No.: 15/773,846

(22) PCT Filed: Nov. 4, 2016

(86) PCT No.: PCT/IB2016/056661
§ 371 (c)(1),
(2) Date: May 4, 2018

(87) PCT Pub. No.: WO2017/077507
PCT Pub. Date: May 11, 2017

(65) Prior Publication Data
US 2018/0318297 A1 Nov. 8, 2018

Related U.S. Application Data

(60) Provisional application No. 62/252,420, filed on Nov. 6, 2015, provisional application No. 62/261,228, filed on Nov. 30, 2015.

(51) Int. Cl.
| | |
|---|---|
| C07D 487/04 | (2006.01) |
| A61P 35/02 | (2006.01) |
| A61P 35/04 | (2006.01) |
| A61P 29/00 | (2006.01) |
| A61K 31/4985 | (2006.01) |

(52) U.S. Cl.
CPC .......... *A61K 31/4985* (2013.01); *A61P 29/00* (2018.01); *A61P 35/02* (2018.01); *A61P 35/04* (2018.01); *C07D 487/04* (2013.01)

(58) Field of Classification Search
CPC ........ C07D 487/04; A61P 35/02; A61P 35/04; A61P 29/00; A61K 31/4985
USPC ........................................... 514/250
See application file for complete search history.

(56) References Cited

U.S. PATENT DOCUMENTS 9,290,504 B2 * 3/2016 Barf .................. A61K 31/55

FOREIGN PATENT DOCUMENTS

| WO | 2013010868 A1 | 1/2013 |
| WO | WO-2015057992 A1 * | 4/2015 |
| WO | 2015110923 A2 | 7/2015 |
| WO | 2016024227 A1 | 2/2016 |

OTHER PUBLICATIONS

RN1420478-14-3, registry database compound, entry date Feb. 13, 2013.*
O'Cruz; Uckun: "Novel Bruton's tyrosine kinase inhibitors currently in development", Oncotargets and Therapy, vol. 6, Mar. 6, 2013 (Mar. 6, 2013), pp. 161-176.
International Search Report dated Dec. 15, 2016 for International Patent Application No. PCT/IB2016/056661, 4 pages.
Written Opinion dated Dec. 15, 2016 for International Patent Application No. PCT/IB2016/056661, 4 pages.

* cited by examiner

*Primary Examiner* — Sun Jae Yoo
(74) *Attorney, Agent, or Firm* — Morgan, Lewis & Bockius LLP

(57) ABSTRACT

In some embodiments, the invention relates to a BTK inhibitor or a pharmaceutically acceptable salt, cocrystal, ester, prodrug, solvate, hydrate or derivative thereof, or to pharmaceutical compositions comprising these compounds and to their use in therapy. In particular, in some embodiments, the present invention relates to imidazopyrazine compounds, pharmaceutical compositions thereof, and the use of the compounds and pharmaceutical compositions in the treatment of a hyperproliferative disorder, an inflammatory disorder, an immune disorder, or an autoimmune disorder.

2 Claims, No Drawings

IMIDAZOPYRAZINE INHIBITORS OF BRUTON'S TYROSINE KINASE

FIELD OF THE INVENTION

In some embodiments, the present invention relates to heterocyclic compounds, to pharmaceutical compositions comprising these compounds, and to their use in therapy. In some embodiments, the present invention relates to the use of imidazopyrazine compounds in the treatment of a hyperproliferative disorder, an inflammatory disorder, an immune disorder, or an autoimmune disorder.

BACKGROUND OF THE INVENTION

B lymphocyte activation is critical in the generation of adaptive immune responses. Derailed B lymphocyte activation is a hallmark of many autoimmune diseases and modulation of this immune response is therefore of therapeutic interest. Recently, the success of B cell therapies in autoimmune diseases has been established. Treatment of rheumatoid arthritis (RA) patients with rituximab (anti-CD20 therapy) is an accepted clinical therapy. More recent clinical trial studies show that treatment with rituximab also ameliorates disease symptoms in relapsing remitting multiple sclerosis (RRMS) and systemic lupus erythematosus (SLE) patients. This success supports the potential for future therapies in autoimmune diseases targeting B cell immunity.

Bruton's tyrosine kinase (BTK) is a Tec family non-receptor protein kinase expressed in B cells and myeloid cells. The function of BTK in signaling pathways activated by the engagement of the B cell receptor (BCR) and FcɛR1 on mast cells is well established. In addition, a function for BTK as a downstream target in Toll like receptor signaling is suggested. BTK is composed of the pleckstrin homology (PH), Tec homology (TH), Src homology 3 (SH3), Src homology 2 (SH2), and tyrosine kinase or Src homology 1 (TK or SH1) domains. The function of BTK in signaling pathways activated by the engagement of the B cell receptor (BCR) in mature B cells and FCER1 on mast cells is well established. Functional mutations in BTK in humans result in a primary immunodeficiency disease (X-linked agammaglobuinaemia) characterized by a defect in B cell development with a block between pro- and pre-B cell stages. The result is an almost complete absence of B lymphocytes, causing a pronounced reduction of serum immunoglobulin of all classes. These findings support a key role for BTK in the regulation of the production of auto-antibodies in autoimmune diseases.

BTK is expressed in numerous B cell lymphomas and leukemias. Other diseases with an important role for dysfunctional B cells are B cell malignancies, as described in Hendriks, et al., *Nat. Rev. Cancer,* 2014, 14, 219-231. The reported role for BTK in the regulation of proliferation and apoptosis of B cells indicates the potential for BTK inhibitors in the treatment of B cell lymphomas. BTK inhibitors have thus been developed as potential therapies for many of these malignancies, as described in D'Cruz, et al., *Onco-Targets and Therapy* 2013, 6, 161-176. With the regulatory role reported for BTK in FccR-mediated mast cell activation, BTK inhibitors may also show potential in the treatment of allergic responses, as described in Gilfillan, et al., *Immunologic. Rev.* 2009, 288, 149-169. Furthermore, BTK is also reported to be implicated in RANKL-induced osteoclast differentiation, as described in Shinohara, et al., *Cell* 2008, 132, 794-806, and therefore may also be of interest for the treatment of bone resorption disorders. Other diseases with an important role for dysfunctional B cells are B cell malignancies. Indeed anti-CD20 therapy is used effectively in the clinic for the treatment of follicular lymphoma, diffuse large B-cell lymphoma and chronic lymphocytic leukemia, as described in Lim, et al., *Haematologica,* 2010, 95, 135-143. The reported role for BTK in the regulation of proliferation and apoptosis of B cells indicates there is potential for BTK inhibitors in the treatment of B cell lymphomas as well. Inhibition of BTK seems to be relevant in particular for B cell lymphomas due to chronic active BCR signaling, as described in Davis, et al., *Nature,* 2010, 463, 88-94.

In many solid tumors, the supportive microenvironment (which may make up the majority of the tumor mass) is a dynamic force that enables tumor survival. The tumor microenvironment is generally defined as a complex mixture of "cells, soluble factors, signaling molecules, extracellular matrices, and mechanical cues that promote neoplastic transformation, support tumor growth and invasion, protect the tumor from host immunity, foster therapeutic resistance, and provide niches for dominant metastases to thrive," as described in Swartz, et al., *Cancer Res.,* 2012, 72, 2473. Although tumors express antigens that should be recognized by T cells, tumor clearance by the immune system is rare because of immune suppression by the microenvironment. Addressing the tumor cells themselves with e.g. chemotherapy has also proven to be insufficient to overcome the protective effects of the microenvironment. New approaches are thus urgently needed for more effective treatment of solid tumors that take into account the role of the microenvironment.

Some of the BTK inhibitors reported to date are not selective over Src-family kinases. With dramatic adverse effects reported for knockouts of Src-family kinases, especially for double and triple knockouts, this is seen as prohibitive for the development of BTK inhibitors that are not selective over the Src-family kinases. Both Lyn-deficient and Fyn-deficient mice exhibit autoimmunity mimicking the phenotype of human lupus nephritis. In addition, Fyn-deficient mice also show pronounced neurological defects. Lyn knockout mice also show an allergic-like phenotype, indicating Lyn as a broad negative regulator of the IgE-mediated allergic response by controlling mast cell responsiveness and allergy-associated traits, as described in Odom, et al., *J. Exp. Med.,* 2004, 199, 1491-1502. Furthermore, aged Lyn knock-out mice develop severe splenomegaly (myeloid expansion) and disseminated monocyte/macrophage tumors, as described in Harder, et al., *Immunity,* 2001, 15, 603-615. These observations are in line with hyperresponsive B cells, mast cells and myeloid cells, and increased Ig levels observed in Lyn-deficient mice. Female Src knock-out mice are infertile due to reduced follicle development and ovulation, as described in Roby, et al., *Endocrine,* 2005, 26, 169-176. The double knockouts Src−/−Fyn−/− and Src−/− Yes−/− show a severe phenotype with effects on movement and breathing. The triple knockouts Src−/− Fyn−/− Yes−/− die at day 9.5, as shown by Klinghoffer, et al., *EMBO* 1, 1999, 18, 2459-2471. For the double knockout Src−/− Hck−/−, two thirds of the mice die at birth, with surviving mice developing osteopetrosis, extramedullary hematopoiseis, anemia, leukopenia, as shown by Lowell, et al., *Blood,* 1996, 87, 1780-1792. Hence, an inhibitor that inhibits multiple or all kinases of the Src-family kinases simultaneously may cause serious adverse effects.

SUMMARY OF THE INVENTION

In one aspect, the BTK inhibitor is a compound of Formula (I) having the structure:

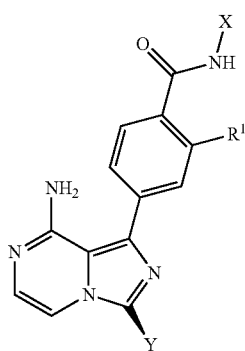

(I)

or a pharmaceutically acceptable salt, cocrystal, ester, prodrug, solvate, hydrate or derivative thereof thereof, wherein:
$R^1$ is hydrogen or methoxy, wherein methoxy is optionally substituted with one or two fluoro;
X is:

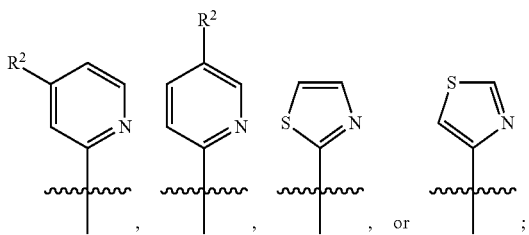

$R^2$ is hydrogen, halogen, methyl, methoxy, or ethoxy, wherein methyl, methoxy, and ethoxy are each optionally substituted with one, two, or three fluoro;
Y is:

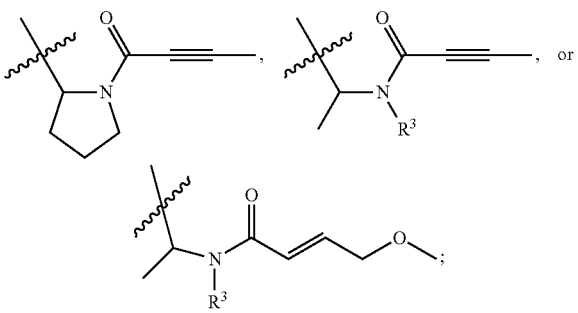

$R^3$ is H or methyl.

In an embodiment, the invention includes a compound of Formula (I) selected from the group consisting of:
4-[8-amino-3-[(1S)-1-[but-2-ynoyl(methyl)amino]ethyl]imidazo[1,5-a]pyrazin-1-yl]-N-(2-pyridyl)benzamide (Formula E-1);
4-[8-amino-3-[(1S)-1-[but-2-ynoyl(methyl)amino]ethyl]imidazo[1,5-a]pyrazin-1-yl]-2-methoxy-N-(2-pyridyl)benzamide (Formula E-2);
4-[8-amino-3-[(1S)-1-[but-2-ynoyl(methyl)amino]ethyl]imidazo[1,5-a]pyrazin-1-yl]-N-(5-methyl-2-pyridyl)benzamide (Formula E-3);
4-[8-amino-3-[(1S)-1-[but-2-ynoyl(methyl)amino]ethyl]imidazo[1,5-a]pyrazin-1-yl]-2-methoxy-N-(5-methyl-2-pyridyl)benzamide (Formula E-4);
4-[8-amino-3-[(2S)-1-but-2-ynoylpyrrolidin-2-yl]imidazo[1,5-a]pyrazin-1-yl]-2-methoxy-N-[4-(trifluoromethyl)-2-pyridyl]benzamide (Formula E-5);
4-[8-amino-3-[(1S)-1-[[(E)-4-methoxybut-2-enoyl]-methylamino]ethyl]imidazo[1,5-a]pyrazin-1-yl]-N-(5-methyl-2-pyridyl)benzamide (Formula E-6);
4-[8-amino-3-[(1S)-1-[but-2-ynoyl(methyl)amino]ethyl]imidazo[1,5-a]pyrazin-1-yl]-2-methoxy-N-[4-(trifluoromethyl)-2-pyridyl]benzamide (Formula E-7);
4-[8-amino-3-[(1S)-1-(but-2-ynoylamino)ethyl]imidazo[1,5-a]pyrazin-1-yl]-2-methoxy-N-[4-(trifluoromethyl)-2-pyridyl]benzamide (Formula E-8);
4-[8-amino-3-[(1S)-1-(but-2-ynoylamino)ethyl]imidazo[1,5-a]pyrazin-1-yl]-2-methoxy-N-(2-pyridyl)benzamide (Formula E-9);
4-[8-amino-3-[(1S)-1-(but-2-ynoylamino)ethyl]imidazo[1,5-a]pyrazin-1-yl]-N-[4-(trifluoromethyl)-2-pyridyl]benzamide (Formula E-10);
4-[8-amino-3-[(1S)-1-(but-2-ynoylamino)ethyl]imidazo[1,5-a]pyrazin-1-yl]-N-(5-methyl-2-pyridyl)benzamide (Formula E-11);
4-[8-amino-3-[(1S)-1-(but-2-ynoylamino)ethyl]imidazo[1,5-a]pyrazin-1-yl]-2-methoxy-N-(5-methyl-2-pyridyl)benzamide (Formula E-12);
4-[8-amino-3-[(1S)-1-[[(E)-4-methoxybut-2-enoyl]amino]ethyl]imidazo[1,5-a]pyrazin-1-yl]-N-(5-methyl-2-pyridyl)benzamide (Formula E-13);
4-[8-amino-3-[(1S)-1-[[(E)-4-methoxybut-2-enoyl]amino]ethyl]imidazo[1,5-a]pyrazin-1-yl]-2-methoxy-N-(5-methyl-2-pyridyl)benzamide (Formula E-14);
4-[8-amino-3-[(2S)-1-but-2-ynoylpyrrolidin-2-yl]imidazo[1,5-a]pyrazin-1-yl]-2-methoxy-N-thiazol-2-yl-benzamide (Formula E-15);
4-[8-amino-3-[(2S)-1-but-2-ynoylpyrrolidin-2-yl]imidazo[1,5-a]pyrazin-1-yl]-N-(5-methyl-2-pyridyl)benzamide (Formula E-16);
4-[8-amino-3-[(2S)-1-but-2-ynoylpyrrolidin-2-yl]imidazo[1,5-a]pyrazin-1-yl]-2-methoxy-N-(5-methyl-2-pyridyl)benzamide (Formula E-17);
(R)-4-(8-amino-3-(1-(but-2-ynoyl)pyrrolidin-2-yl)imidazo[1,5-a]pyrazin-1-yl)-N-(thiazol-4-yl)benzamide (Formula E-24); and a pharmaceutically acceptable salt, cocrystal, ester, prodrug, solvate, hydrate or derivative thereof.

DETAILED DESCRIPTION OF THE INVENTION

While preferred embodiments of the invention are shown and described herein, such embodiments are provided by way of example only and are not intended to otherwise limit the scope of the invention. Various alternatives to the described embodiments of the invention may be employed in practicing the invention.

Unless defined otherwise, all technical and scientific terms used herein have the same meaning as is commonly understood by one of skill in the art to which this invention belongs. All patents and publications referred to herein are incorporated by reference in their entireties.

The terms "co-administration," "co-administering," "administered in combination with," and "administering in combination with" as used herein, encompass administration of two or more agents to a subject so that both agents and/or their metabolites are present in the subject at the same time. Co-administration includes simultaneous administration in separate compositions, administration at different times in separate compositions, or administration in a composition in which two or more agents are present.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, etc., which can readily be determined by one of ordinary skill in the art. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "pharmaceutically acceptable salt" refers to salts derived from a variety of organic and inorganic counter ions known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid and phosphoric acid. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In selected embodiments, the pharmaceutically acceptable base addition salt is chosen from ammonium, potassium, sodium, calcium, and magnesium salts. The term "cocrystal" refers to a molecular complex derived from a number of cocrystal formers known in the art. Unlike a salt, a cocrystal typically does not involve hydrogen transfer between the cocrystal and the drug, and instead involves intermolecular interactions, such as hydrogen bonding, aromatic ring stacking, or dispersive forces, between the cocrystal former and the drug in the crystal structure.

"Pharmaceutically acceptable carrier" or "pharmaceutically acceptable excipient" is intended to include any and all solvents, dispersion media, coatings, antibacterial and antifungal agents, isotonic and absorption delaying agents. The use of such media and agents for pharmaceutically active substances is well known in the art. Except insofar as any conventional media or agent is incompatible with the active ingredient, its use in the therapeutic compositions of the invention is contemplated. Supplementary active ingredients can also be incorporated into the described compositions.

"Prodrug" is intended to describe a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers the advantages of solubility, tissue compatibility or delayed release in a mammalian organism (see, e.g., Bundgaard, Design of Prodrugs, Elsevier, Amsterdam, 1985). The term "prodrug" is also intended to include any covalently bonded carriers, which release the active compound in vivo when administered to a subject. Prodrugs of an active compound, as described herein, may be prepared by modifying functional groups present in the active compound in such a way that the modifications are cleaved, either in routine manipulation or in vivo, to yield the active parent compound. Prodrugs include, for example, compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetates, formates and benzoate derivatives of an alcohol, various ester derivatives of a carboxylic acid, or acetamide, formamide and benzamide derivatives of an amine functional group in the active compound.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

"Isomers" are different compounds that have the same molecular formula. "Stereoisomers" are isomers that differ only in the way the atoms are arranged in space—i.e., having a different stereochemical configuration. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon can be specified by either (R) or (S). Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R) or (S). The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

The term "hydrate" includes but is not limited to hemihydrate, monohydrate, dihydrate, trihydrate and the like. Hydrates of the BTK inhibitors may be prepared by contacting the BTK inhibitors with water under suitable conditions to produce the hydrate of choice.

In some embodiments, the enantiomerically enriched composition has a higher potency with respect to therapeutic utility per unit mass than does the racemic mixture of that composition. Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., Enantiomers, Racemates and Resolutions, Wiley Interscience, New York, 1981; Eliel, Stereochemistry of Carbon Compounds, McGraw-Hill, N Y, 1962; and Eliel and Wilen, Stereochemistry of Organic Compounds, Wiley, New York, 1994.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

"Solvate" refers to a compound in physical association with one or more molecules of a pharmaceutically acceptable solvent.

"Substituted" means that the referenced group may have attached one or more additional groups, radicals or moieties individually and independently selected from, for example, acyl, alkyl, alkylaryl, cycloalkyl, aralkyl, aryl, carbohydrate, carbonate, heteroaryl, heterocycloalkyl, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamidyl, sulfoxyl, sulfonate, urea, and amino, including mono- and di-substituted amino groups, and protected derivatives thereof. The substituents themselves may be substituted, for example, a cycloalkyl substituent may itself have a halide substituent at one or more of its ring carbons. The term "optionally substituted" means optional substitution with the specified groups, radicals or moieties.

Compounds of the invention also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

BTK Inhibitors

BTK inhibitors of the present invention include BTK inhibitors that bind covalently to the target (in an irreversible manner) and BTK inhibitors that bind non-covalently to the target (in a reversible manner). In an embodiment, the BTK inhibitor binds covalently to the cysteine residue at position 481 of BTK.

In one aspect, the BTK inhibitor is a compound of Formula (I) having the structure:

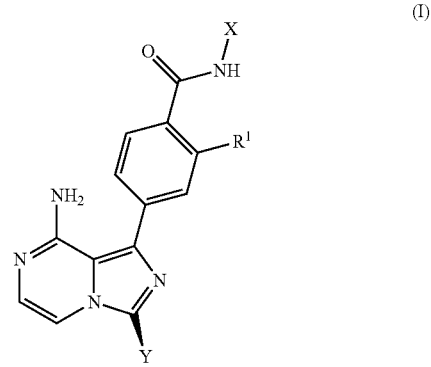

(I)

or a pharmaceutically acceptable salt, cocrystal, ester, prodrug, solvate, hydrate or derivative thereof, wherein:

$R^1$ is hydrogen or methoxy, wherein methoxy is optionally substituted with one or two fluoro;

X is:

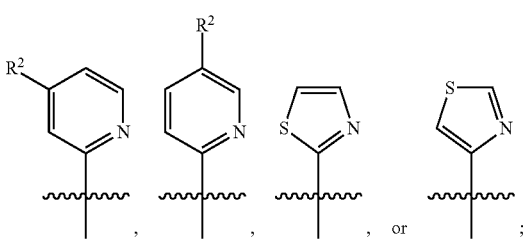

$R^2$ is hydrogen, halogen, methyl, methoxy, or ethoxy, wherein methyl, methoxy, and ethoxy are each optionally substituted with one, two, or three fluoro;

Y is:

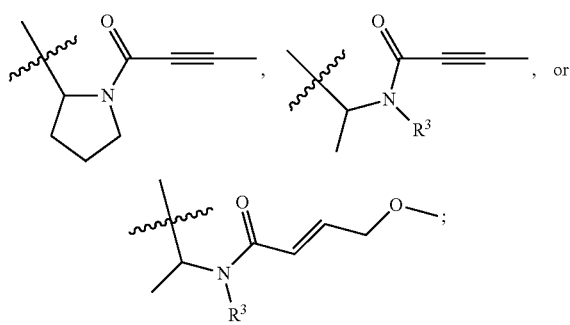

R³ is H or methyl.

In an embodiment, the BTK inhibitor is a compound of Formula (I), wherein:

R¹ is hydrogen;

X is:

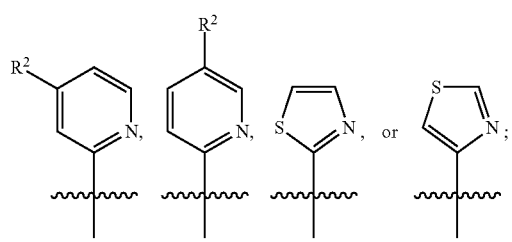

R² is hydrogen, halogen, methyl, methoxy, or ethoxy, wherein methyl, methoxy, and ethoxy are each optionally substituted with one, two, or three fluoro;

Y is:

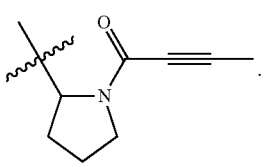 [SMILES: *C1CCCN1C(=O)C#CC]

In an embodiment, the BTK inhibitor is a compound of Formula (I), wherein:

R¹ is methoxy;

X is:

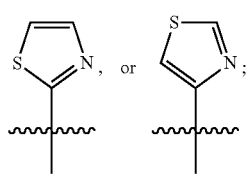 [SMILES: *c1nccs1 ; "," ; "or" ; *c1cscn1 ; ";"]

Y is:

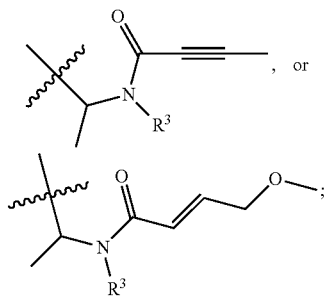

R³ is H or methyl.

In an embodiment, the BTK inhibitor is a compound of Formula (I), wherein:

R¹ is hydrogen;

X is:

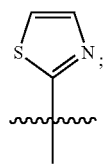

Y is:

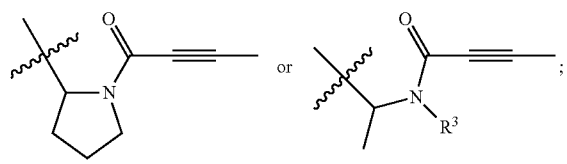

R³ is H or methyl.

In an embodiment, the BTK inhibitor is a compound of Formula (I), wherein R¹ is hydrogen or methoxy, wherein methoxy is optionally substituted with one or two fluoro;

X is:

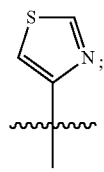 [SMILES: *c1cscn1 ; ";"]

R² is hydrogen, halogen, methyl, methoxy, or ethoxy, wherein methyl, methoxy, and ethoxy are each optionally substituted with one, two, or three fluoro;

Y is:

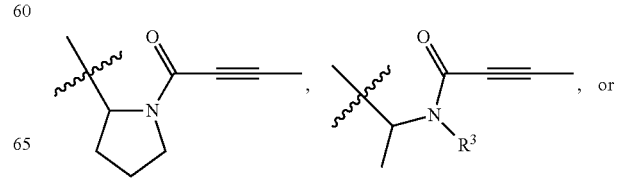

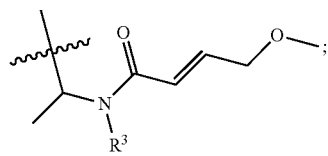

R³ is H or methyl.

In an embodiment, the BTK inhibitor is a compound of Formula (I), wherein R¹ is hydrogen or methoxy, wherein methoxy is optionally substituted with one or two fluoro;

X is:

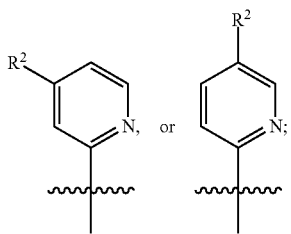

R² is hydrogen, halogen, methyl, methoxy, or ethoxy, wherein methyl, methoxy, and ethoxy are each optionally substituted with one, two, or three fluoro;

Y is:

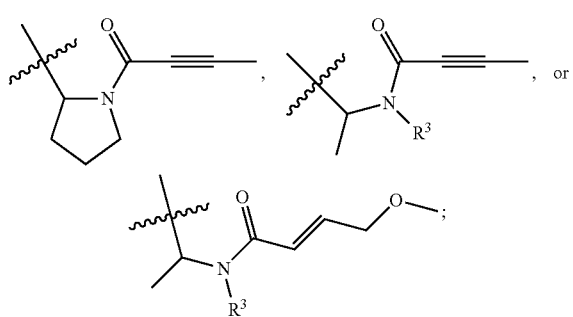

R³ is H or methyl.

In an embodiment, the BTK inhibitor is a compound of Formula (I), wherein R¹ is hydrogen or methoxy, wherein methoxy is optionally substituted with one or two fluoro;

X is:

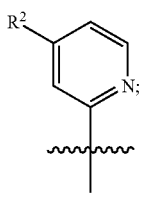

R² is hydrogen, halogen, methyl, methoxy, or ethoxy, wherein methyl, methoxy, and ethoxy are each optionally substituted with one, two, or three fluoro;

Y is:

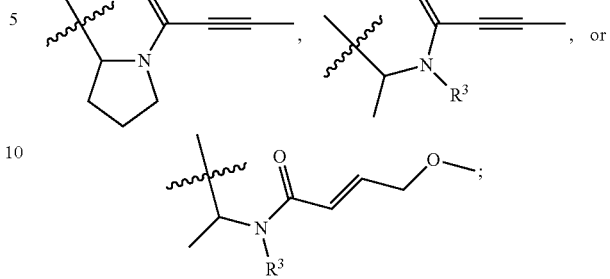

R³ is H or methyl.

In an embodiment, the BTK inhibitor is a compound of Formula (I), wherein R¹ is hydrogen or methoxy, wherein methoxy is optionally substituted with one or two fluoro;

X is:

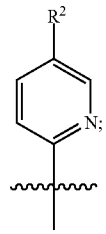

R² is hydrogen, halogen, methyl, methoxy, or ethoxy, wherein methyl, methoxy, and ethoxy are each optionally substituted with one, two, or three fluoro;

Y is:

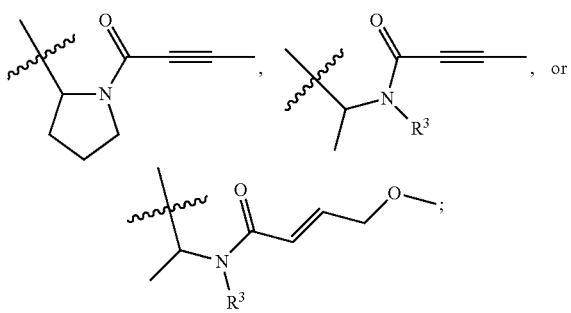

R³ is H or methyl.

In an embodiment, the BTK inhibitor is a compound of Formula (I), wherein R¹ is hydrogen or methoxy, wherein methoxy is optionally substituted with one or two fluoro;

X is:

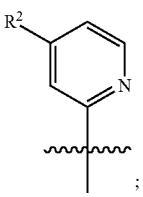

R² is hydrogen, halogen, methyl, methoxy, or ethoxy, wherein methyl, methoxy, and ethoxy are each optionally substituted with one, two, or three fluoro; Y is:

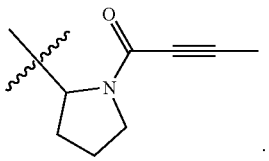 [SMILES: *C1CCCN1C(=O)C#CC]

In an embodiment, the BTK inhibitor is a compound of Formula (I), wherein R¹ is hydrogen or methoxy, wherein methoxy is optionally substituted with one or two fluoro; X is:

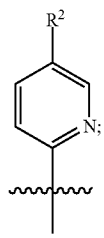

R² is hydrogen, halogen, methyl, methoxy, or ethoxy, wherein methyl, methoxy, and ethoxy are each optionally substituted with one, two, or three fluoro; Y is:

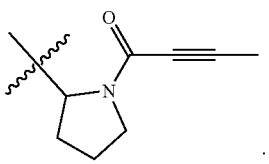

In an embodiment, the BTK inhibitor is a compound of Formula (I) selected from the group consisting of:

4-[8-amino-3-[(1S)-1-[but-2-ynoyl(methyl)amino]ethyl]imidazo[1,5-a]pyrazin-1-yl]-N-(2-pyridyl)benzamide (Formula E-1);

4-[8-amino-3-[(1S)-1-[but-2-ynoyl(methyl)amino]ethyl]imidazo[1,5-a]pyrazin-1-yl]-2-methoxy-N-(2-pyridyl)benzamide (Formula E-2);

4-[8-amino-3-[(1S)-1-[but-2-ynoyl(methyl)amino]ethyl]imidazo[1,5-a]pyrazin-1-yl]-N-(5-methyl-2-pyridyl)benzamide (Formula E-3);

4-[8-amino-3-[(1S)-1-[but-2-ynoyl(methyl)amino]ethyl]imidazo[1,5-a]pyrazin-1-yl]-2-methoxy-N-(5-methyl-2-pyridyl)benzamide (Formula E-4);

4-[8-amino-3-[(2S)-1-but-2-ynoylpyrrolidin-2-yl]imidazo[1,5-a]pyrazin-1-yl]-2-methoxy-N-[4-(trifluoromethyl)-2-pyridyl]benzamide (Formula E-5);

4-[8-amino-3-[(1S)-1-[[(E)-4-methoxybut-2-enoyl]-methylamino]ethyl]imidazo[1,5-a]pyrazin-1-yl]-N-(5-methyl-2-pyridyl)benzamide (Formula E-6);

4-[8-amino-3-[(1S)-1-[but-2-ynoyl(methyl)amino]ethyl]imidazo[1,5-a]pyrazin-1-yl]-2-methoxy-N-[4-(trifluoromethyl)-2-pyridyl]benzamide (Formula E-7);

4-[8-amino-3-[(1S)-1-(but-2-ynoylamino)ethyl]imidazo[1,5-a]pyrazin-1-yl]-2-methoxy-N-[4-(trifluoromethyl)-2-pyridyl]benzamide (Formula E-8);

4-[8-amino-3-[(1S)-1-(but-2-ynoylamino)ethyl]imidazo[1,5-a]pyrazin-1-yl]-2-methoxy-N-(2-pyridyl)benzamide (Formula E-9);

4-[8-amino-3-[(1S)-1-(but-2-ynoylamino)ethyl]imidazo[1,5-a]pyrazin-1-yl]-N-[4-(trifluoromethyl)-2-pyridyl]benzamide (Formula E-10);

4-[8-amino-3-[(1S)-1-(but-2-ynoylamino)ethyl]imidazo[1,5-a]pyrazin-1-yl]-N-(5-methyl-2-pyridyl)benzamide (Formula E-11);

4-[8-amino-3-[(1S)-1-(but-2-ynoylamino)ethyl]imidazo[1,5-a]pyrazin-1-yl]-2-methoxy-N-(5-methyl-2-pyridyl)benzamide (Formula E-12);

4-[8-amino-3-[(1S)-1-[[(E)-4-methoxybut-2-enoyl]amino]ethyl]imidazo[1,5-a]pyrazin-1-yl]-N-(5-methyl-2-pyridyl)benzamide (Formula E-13);

4-[8-amino-3-[(1S)-1-[[(E)-4-methoxybut-2-enoyl]amino]ethyl]imidazo[1,5-a]pyrazin-1-yl]-2-methoxy-N-(5-methyl-2-pyridyl)benzamide (Formula E-14);

4-[8-amino-3-[(2S)-1-but-2-ynoylpyrrolidin-2-yl]imidazo[1,5-a]pyrazin-1-yl]-2-methoxy-N-thiazol-2-yl-benzamide (Formula E-15);

4-[8-amino-3-[(2S)-1-but-2-ynoylpyrrolidin-2-yl]imidazo[1,5-a]pyrazin-1-yl]-N-(5-methyl-2-pyridyl)benzamide (Formula E-16);

4-[8-amino-3-[(2S)-1-but-2-ynoylpyrrolidin-2-yl]imidazo[1,5-a]pyrazin-1-yl]-2-methoxy-N-(5-methyl-2-pyridyl)benzamide (Formula E-17);

(R)-4-(8-amino-3-(1-(but-2-ynoyl)pyrrolidin-2-yl)imidazo[1,5-a]pyrazin-1-yl)-N-(thiazol-4-yl)benzamide (Formula E-24);

and a pharmaceutically acceptable salt, cocrystal, ester, prodrug, solvate, hydrate or derivative thereof.

In an embodiment, the BTK inhibitor is a compound selected from the group consisting of:

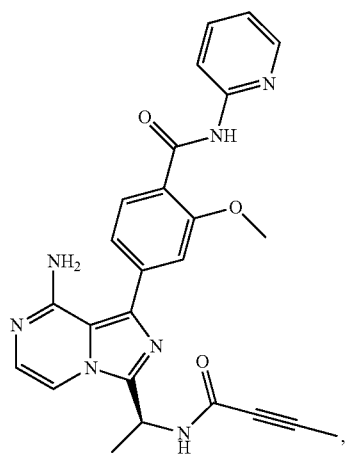

-continued
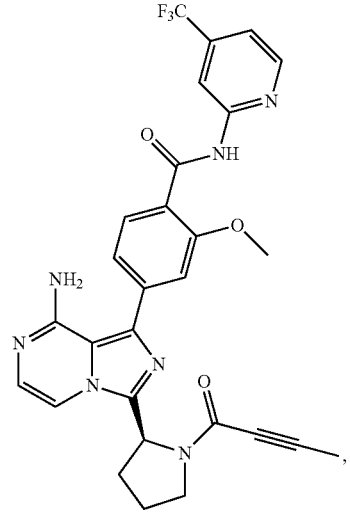
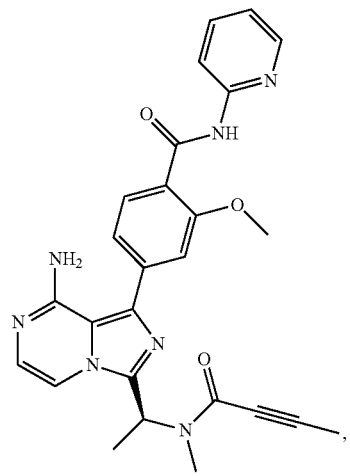
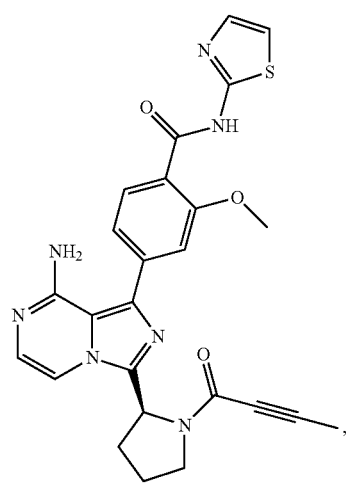
-continued
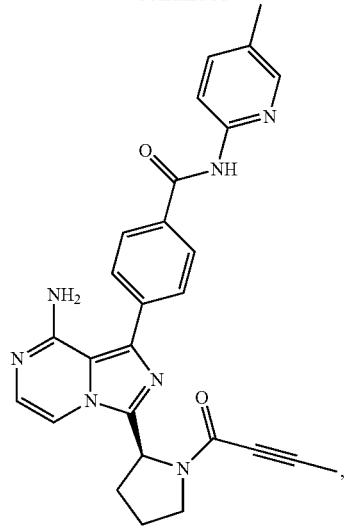
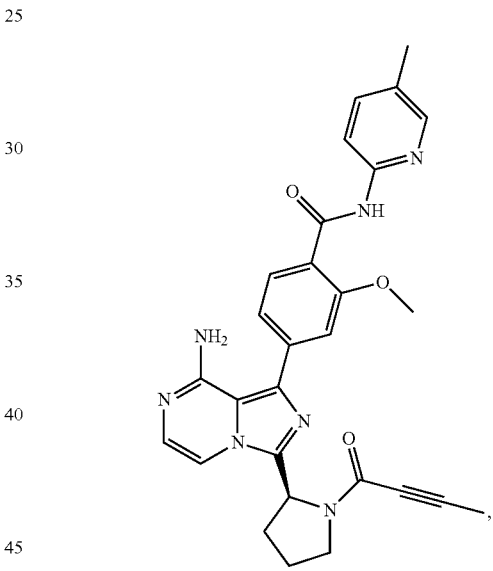
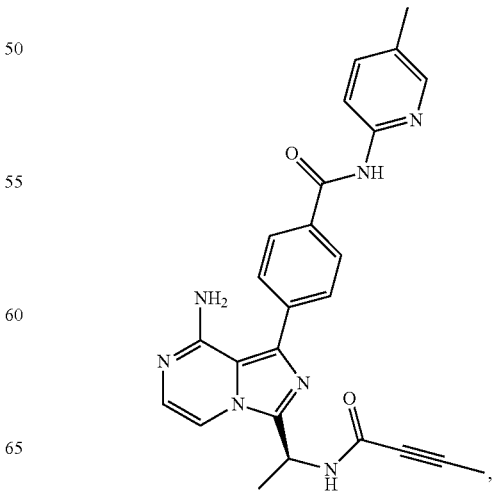

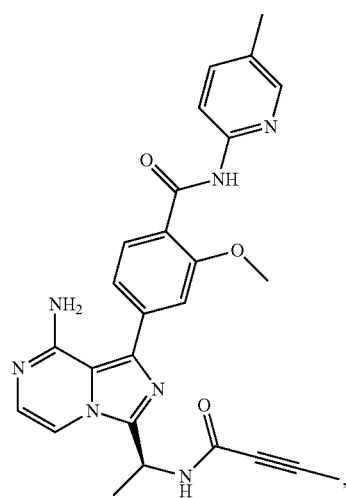
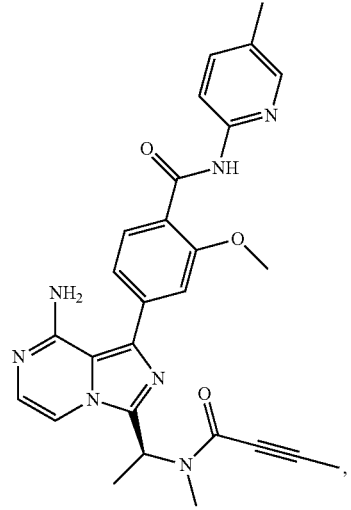
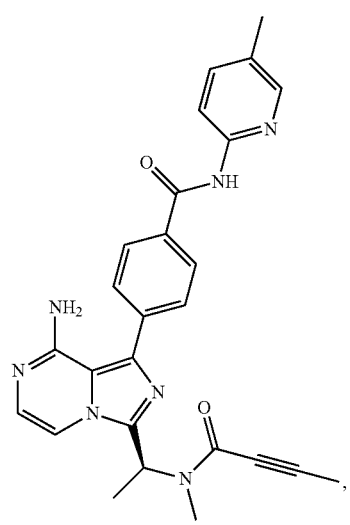
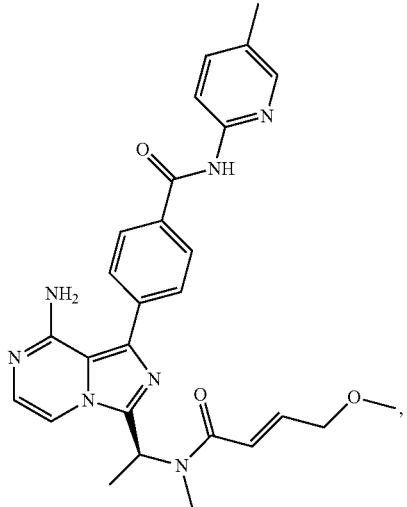
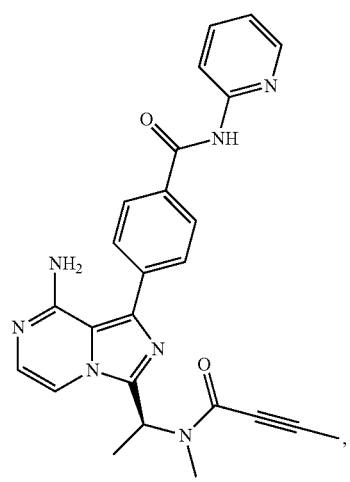

-continued

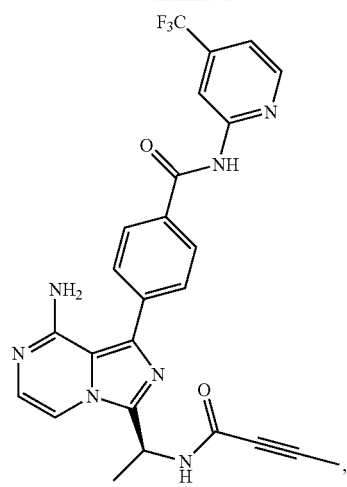

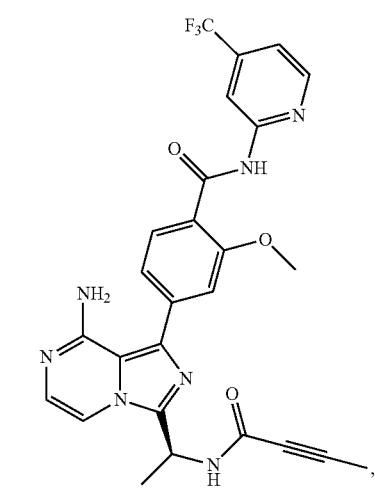

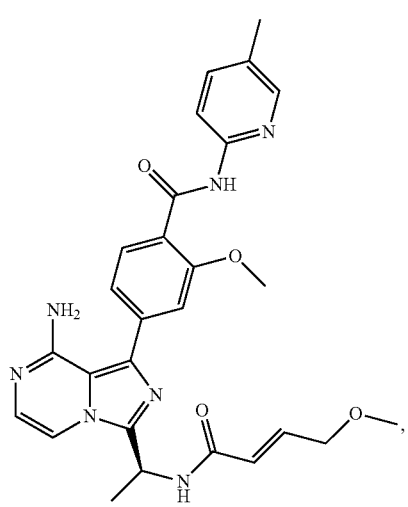

-continued

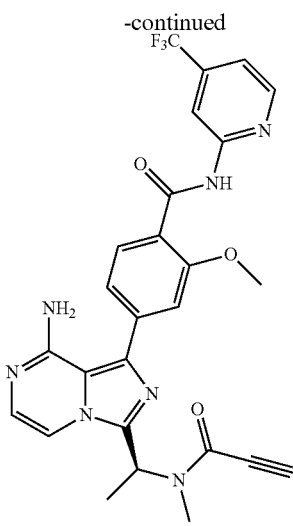

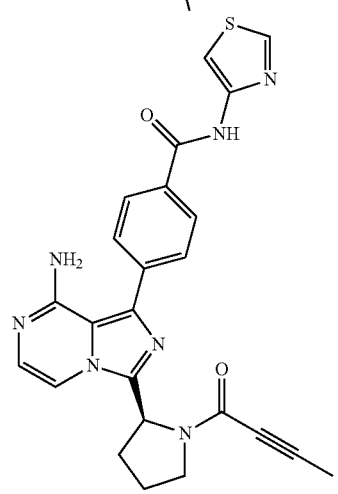

enantiomers thereof, and a pharmaceutically acceptable salt, cocrystal, ester, prodrug, solvate, hydrate or derivative thereof.

Pharmaceutical Compositions

In selected embodiments, the invention provides pharmaceutical compositions for treating solid tumor cancers, lymphomas and leukemia.

The pharmaceutical compositions are typically formulated to provide a therapeutically effective amount of a BTK inhibitor as the active ingredients, or a pharmaceutically acceptable salt, cocrystal, ester, prodrug, solvate, hydrate or derivative thereof. Where desired, the pharmaceutical compositions contain a pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The pharmaceutical compositions are administered as BTK inhibitor. Where desired, other agent(s) may be mixed into a preparation or both components may be formulated into separate preparations for use in combination separately or at the same time.

In selected embodiments, the concentration of each of the BTK inhibitors provided in the pharmaceutical compositions of the invention is independently less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v, relative to the total mass or volume of the pharmaceutical composition.

In selected embodiments, the concentration of each of the BTK inhibitors provided in the pharmaceutical compositions of the invention is independently greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v, relative to the total mass or volume of the pharmaceutical composition.

In selected embodiments, the concentration of each of the BTK inhibitors of the invention is independently in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12% or approximately 1% to approximately 10% w/w, w/v or v/v, relative to the total mass or volume of the pharmaceutical composition.

In selected embodiments, the concentration of each of the BTK inhibitors of the invention is independently in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v, relative to the total mass or volume of the pharmaceutical composition.

In selected embodiments, the amount of each of the BTK inhibitors of the invention is independently equal to or less than 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g or 0.0001 g.

In selected embodiments, the amount of each of the BTK inhibitors of the invention is independently more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, or 3 g.

Each of the BTK inhibitors according to the invention is effective over a wide dosage range. For example, in the treatment of adult humans, dosages independently range from 0.01 to 1000 mg, from 0.5 to 100 mg, from 1 to 50 mg per day, and from 5 to 40 mg per day are examples of dosages that may be used. The exact dosage will depend upon the route of administration, the form in which the compound is administered, the gender and age of the subject to be treated, the body weight of the subject to be treated, and the preference and experience of the attending physician.

Described below are non-limiting pharmaceutical compositions and methods for preparing the same.

Pharmaceutical Compositions for Oral Administration

In selected embodiments, the invention provides a pharmaceutical composition for oral administration containing a BTK inhibitor disclosed herein and a pharmaceutical excipient suitable for oral administration.

In selected embodiments, the invention provides a solid pharmaceutical composition for oral administration containing: (i) an effective amount of a BTK inhibitor disclosed herein and (ii) a pharmaceutical excipient suitable for oral administration.

In selected embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient(s) into association with the carrier, which constitutes one or more necessary ingredients. In general, the compositions are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The invention further encompasses anhydrous pharmaceutical compositions and dosage forms since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

Each of the BTK inhibitors as active ingredients can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which disintegrate in the bottle. Too little may be insufficient for disintegration to occur, thus altering the rate and extent of release of the active ingredients from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactants which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10.

However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In an embodiment, the composition may include a solubilizer to ensure good solubilization and/or dissolution of the compound of the present invention and to minimize precipitation of the compound of the present invention. This can be especially important for compositions for non-oral use—e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, epsilon-caprolactone and isomers thereof, 6-valerolactone and isomers thereof, (3-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals and alkaline earth metals. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid.

Pharmaceutical Compositions for Injection

In selected embodiments, the invention provides a pharmaceutical composition for injection containing the BTK inhibitors and a pharmaceutical excipient suitable for injection. Components and amounts of agents in the compositions are as described herein.

The forms in which the compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol and liquid polyethylene glycol (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, and thimerosal.

Sterile injectable solutions are prepared by incorporating the BTK inhibitors in the required amounts in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are spray-drying, vacuum-drying and freeze-drying (lyophilization) techniques which yield a powder of the active ingredient plus any additional desired ingredient from a previously sterile-filtered solution thereof. Other lyophilized or spray-dried formulations known to those of skill in the art may also be employed with the present invention. Such formulations include those disclosed in U.S. Pat. Nos. 5,908,826, 6,267,958, 7,682,609, 7,592,004, and 8,298,530, and U.S. Patent Application Publication No. 2010/0158925, the teachings of which are specifically incorporated by reference herein.

Dosages and Dosing Regimens

The amounts of the BTK inhibitors administered will be dependent on the mammal being treated, the severity of the disorder or condition, the rate of administration, the disposition of the compounds and the discretion of the prescribing physician. However, an effective dosage is in the range of about 0.001 to about 100 mg per kg body weight per day, such as about 1 to about 35 mg/kg/day, in single or divided doses. For a 70 kg human, this would amount to about 0.05 to 7 g/day, such as about 0.05 to about 2.5 g/day. In some instances, dosage levels below the lower limit of the aforesaid range may be more than adequate, while in other cases still larger doses may be employed without causing any harmful side effect—e.g., by dividing such larger doses into several small doses for administration throughout the day.

In selected embodiments, the BTK inhibitor is administered in a single dose. Typically, such administration will be by injection, for example by intravenous injection, in order to introduce the agents quickly. However, other routes may be used as appropriate. A single dose of the BTK inhibitor may also be used for treatment of an acute condition.

In selected embodiments, the BTK inhibitor is administered in multiple doses. Dosing may be about once, twice, three times, four times, five times, six times, or more than six times per day. Dosing may be about once a month, once every two weeks, once a week, or once every other day. In other embodiments, the BTK inhibitor is administered about once per day to about 6 times per day. In another embodiment the administration of the BTK inhibitor continues for less than about 7 days. In yet another embodiment the administration continues for more than about 6, 10, 14, 28 days, two months, six months, or one year. In some cases, continuous dosing is achieved and maintained as long as necessary.

Administration of the agents of the invention may continue as long as necessary. In selected embodiments, the BTK inhibitor is administered for more than 1, 2, 3, 4, 5, 6, 7, 14, or 28 days. In some embodiments, the BTK inhibitor is administered for less than 28, 14, 7, 6, 5, 4, 3, 2, or 1 day. In selected embodiments, the BTK inhibitor is administered chronically on an ongoing basis—e.g., for the treatment of chronic effects.

An effective amount of the combination of the BTK inhibitor may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

Methods of Treatment

In some embodiments, the invention relates to a method of treating a hyperproliferative disorder, an inflammatory disorder, an immune disorder, or autoimmune disorder in a mammal that comprises administering to said mammal a therapeutically effective amount of a BTK inhibitor, or a pharmaceutically acceptable salt, cocrystal, ester, prodrug, solvate, hydrate or derivative of the BTK inhibitor.

In some embodiments, the invention relates to a method of treating, with a BTK inhibitor, a hyperproliferative disorder in a mammal selected from the group consisting of bladder cancer, head and neck cancer, pancreatic ductal adenocarcinoma (PDA), pancreatic cancer, colon carcinoma, mammary carcinoma, breast cancer, fibrosarcoma, mesothelioma, renal cell carcinoma, lung carcinoma, thyoma, prostate cancer, colorectal cancer, ovarian cancer, acute myeloid leukemia, thymus cancer, brain cancer, squamous cell cancer, skin cancer, eye cancer, retinoblastoma, melanoma, intraocular melanoma, oral cavity and oropharyngeal cancers, gastric cancer, stomach cancer, cervical cancer, head, neck, renal cancer, kidney cancer, liver cancer, ovarian cancer, prostate cancer, colorectal cancer, esophageal cancer, testicular cancer, gynecological cancer, thyroid cancer, acquired immune deficiency syndrome (AIDS)-related cancers (e.g., lymphoma and Kaposi's sarcoma), viral-induced cancer, glioblastoma, esophogeal tumors, hematological neoplasms, primary central nervous system lymphoma, non-small-cell lung cancer (NSCLC), chronic myelocytic leukemia, diffuse large B-cell lymphoma (DLBCL), esophagus tumor, follicle center lymphoma, head and neck tumor, hepatitis C virus infection, hepatocellular carcinoma, Hodgkin's disease, metastatic colon cancer, multiple myeloma, non-Hodgkin's lymphoma, ovary tumor, pancreas tumor, renal cell carcinoma, small-cell lung cancer, or stage IV melanoma. In selected embodiments, the invention relates to a method of treating with a BTK inhibitor disorders such as hyperproliferative disorder, including but not limited to cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g., lymphoma and Kaposi's sarcoma) or viral-induced cancer. In some embodiments, said pharmaceutical composition is for the treatment of a non-cancerous hyperproliferative disorder such as benign hyperplasia of the skin (e.g., psoriasis), restenosis, or prostate (e.g., benign prostatic hypertrophy (BPH)).

In some embodiments, the invention relates to a method of treating an inflammatory, immune, or autoimmune disorder in a mammal with a BTK inhibitor. In selected embodiments, the invention also relates to a method of treating a disease with a BTK inhibitor, wherein the disease is selected from the group consisting of tumor angiogenesis, chronic inflammatory disease, rheumatoid arthritis, atherosclerosis, inflammatory bowel disease, skin diseases such as psoriasis, eczema, and scleroderma, Type 1 diabetes, Type 2 diabetes, diabetic retinopathy, retinopathy of prematurity, age-related macular degeneration, hemangioma, glioma and melanoma, ulcerative colitis, atopic dermatitis, pouchitis, spondylarthritis, uveitis, Behcets disease, polymyalgia rheumatica, giant-cell arteritis, sarcoidosis, Kawasaki disease, juvenile idiopathic arthritis, hidradenitis suppurativa, Sjögren's syndrome, psoriatic arthritis, juvenile rheumatoid arthritis, ankylosing spondylitis, Crohn's Disease, lupus, lupus nephritis, human leukocyte antigen (HLA) associated diseases, autoantibodies, immunotherapy, Addison's disease, autoimmune polyendocrine syndrome type 1 (APS-1), autoimmune polyendocrine syndrome type 2 (APS-2), Grave's disease, Hashimoto's thyroiditis, polyendocrine autoimmunity, iatrogenic autoimmunity, idiopathic hypoparathyroidism, vitilago, and lupus nephritis.

In some embodiments, the invention provides a method of treating an inflammatory, immune, or autoimmune disorder that is a chronic B cell disorder in which BCR signaling leads to the inappropriate production of autoimmune antibodies or release of pro-inflammatory cytokines and activation of immune cells including inflammatory T cells. In diseases of this type, reducing BCR signaling by inhibition of BTK may lead to therapeutic benefit. In some embodiments, the invention provides a method of treating an inflammatory, immune, or autoimmune disorder selected from the group consisting of rheumatoid arthritis (RA), juvenile RA, juvenile idiopathic arthritis, osteoarthritis, psoriatic arthritis, psoriasis vulgaris, pemphigus, bullous pemphigoid, osteoarthritis, infectious arthritis, progressive chronic arthritis, polymyalgia rheumatic, deforming arthritis, traumatic arthritis, gouty arthritis, Reiter's syndrome, polychrondritis, acute synovitis, ankylosing spondylitis, spondylitis, Sjogren's syndrome (SS), systemic lupus erythromatosus (SLE), discoid lupus erythromatosus (discoid LE), LE tumidus, lupus nephritis (LN), antiphospholipidosis, dermatomyositis, polymyositis, autoimmune hematologic disorders, thrombocytopenia, idiopathic thrombocytopenia purpura, thrombotic thrombocytopenia purpura, autoimmune (cold) agglutinin disease, autoimmune hemolytic anemia, cryoglobulinemia, aplastic anemia, neutropenia, autoimmune vasculitis, Behcet's disease, anti-neutrophil cytoplasmic antibody (ANCA)-associated vasculitis, scleroderma, systemic sclerosis, myasthenia gravis, multiple sclerosis (MS), chronic focal encephalitis, Guillian-Barre syndrome, chronic fatigue syndrome, systemic exertion intolerance disease, neuromyelitis optica, autoimmune uveitis, conjunctivitis, keratoconjuctivitis, Grave's disease, thyroid associated opthalmopathy, chronic thyroiditis, granulomatosis with microscopic polyangitis, Wegener's granulomatosis, autoimmune gastritis, autoimmune inflammatory bowel diseases, ulcerative colitis, Crohn's disease, graft versus host disease, idiopathic sprue, autoimmune hepatitis, active hepatitis (acute and chronic), idiopathic pulmonary fibrosis, bronchitis, pulmonary interstitial fibrosis, chronic inflammatory pulmonary disease, sarcoidosis, idiopathic membranous nephropathy, IgA nephropathy, glomerulosclerosis, glomerulonephritis (with or without nephrotic syndrome), pancreatitis and Type 1 or Type 2 diabetes.

In some embodiments, the invention provides a method of treating an inflammatory, immune, or autoimmune disorder, wherein the inflammatory, immune, or autoimmune disorder is a chronic autoimmune and inflammatory disorder in which BTK signaling in myeloid cells and mast cells leads to the inappropriate release of pro-inflammatory cytokines and activation of immune cells including inflammatory T cells, autoreactive B cells, activated tissue macrophages, activated mast cells, infiltrating monocytes and granulocytic inflammatory infiltrates, and activation of tissue-resident dendritic cell populations. In diseases of this nature, reducing BTK signaling through surface or endocytic receptors on the myeloid cells may lead to therapeutic benefit. In some embodiments, the invention provides a method of treating an inflammatory, immune, or autoimmune disorder selected from the group consisting of diabetic retinopathy, giant cell arteritis, Kawasaki disease, inflammatory bowel disease, irritable bowel disease, idiopathic sprue, enteropathy, post-herpetic neuralgia, polymyalgia rheumatic, primary biliary cirrhosis, myasthenia gravis, inflammatory pain, cachexia, periodontal disease, otitis media, pneumoconiosis, mononucleosis, pulmonary emphysema, pulmonary fibrosis, silicosis, chronic inflammatory pulmonary disease, chronic obstructive pulmonary disease, pulmonary insufficiency, pulmonary interstitial fibrosis, whipple, benign hyperplasia of the skin (e.g., psoriasis), myalgias caused by infections, cachexia secondary to infections, systemic exertion intolerance disease, atherosclerosis, granulomatosis, granulomatosis with microscopic polyangitis, hidradenitis suppurativa, age-related macular degeneration, and amyloidosis.

In some embodiments, the invention provides a method of treating an inflammatory, immune, or autoimmune disorder, wherein the inflammatory, immune, or autoimmune disorder is a dermatosis in which BTK-mediated signals are involved with the recruitment, activation and/or proliferation of inflammatory cells and production of inflammatory mediators and antimicrobial peptides in the skin. In some embodiments, the invention provides a method of treating a dermatosis wherein the dermatosis results from dermal manifestations of systemic diseases where sensitization, lymphocyte recruitment, lymphocyte skewing by local or lymph-node antigen presenting cells, activation of skin-resident or skin-homing lymphocytes, innate immune sensing, keratinocyte antimicrobial responses, activation of resident or infiltrating myeloid dendritic cells, plasmacytoid dendritic cells, macrophages, mast cells, neutrophils, and/or Langerhans cells leads to development of skin lesions. In some embodiments, the invention provides a method of treating a dermatosis selected from the group consisting of psoriasis vulgaris, guttate psoriasis, erythrodermic psoriasis, psoriatic nails, annular pustular psoriasis, pustular psoriasis, inverse psoriasis, psoriatic arthritis, keratoderma blennorrhagicum, parapsoriasis, erythema nodosum, palmoplantar hidradentitis, atopic dermatitis, atopic eczema, seborrheic eczema, seborrheic dermatitis, dyshidrosis, rosacea, cutaneous lupus erythematosus, acute cutaneous lupus erythematosus, subacute cutaneous lupus erythematosus, discoid lupus erythematosus, lupus erythromatosus tumidus, lupus nephritis (LN), lupus erythematosus panniculitis, erythema multiforme, verruca, verrucous lupus erythematosus, vitiligo, alopecia areata, purigo nodularis, lichen planus, purigo pigmentosum, pemphigus vulgaris, bullous pemphigoid, pemphigus erythematosus, pemphigus nodularis, erythrodermic sarcoidosis, granulomatous dermatisis, scleroderma, systemic sclerosis, cutaneous manifestations of systemic sclerosis, diffuse cutaneous mastocytosis, erythrodermic mastocytosis, granuloma annulare, chondrodermatitis nodularis, contact dermatitis, drug eruptions, linear IgA bullous dermatosis, eosinophilic dermatitis, keratosis pilaris, lymphomatoid papulosis, pityriasis lichenoides et varioliformis acuta (PLEVA), lichenoides chronica (PLC), febrile ulceronecrotic Mucha-Habermann disease (FUMHD), chronic urticaria, rheumatoid neutrophilic dermatitis, cryoglobulinemic purpura, and purpura hyperglobulinemica.

In some embodiments, the invention provides a method of treating a hyperproliferative disorder, wherein the hyperproliferative disorder is a chronic autoimmune and inflammatory disorder of the bone in which BTK signaling in osteoclasts, mast cells, and myeloid cells is involved in osteolysis, osteoclastic processes, imbalance of bone remodeling processes, or loss of bone density. Diseases of this nature, which often have an autoimmune component as well, include osteoarthritis, bone loss due to metastases, osteolytic lesions, osteoporosis, ankylosing spondylitis, spondylarthritis, diffuse idiopathic skeletal hyperostosis, gouty arthritis, and bone disorders related to multiple myeloma. In some embodiments, the invention provides a method of treating a hyperproliferative disorder, wherein the hyperproliferative disorder is selected from the group consisting of osteoarthritis, bone loss due to metastases, osteolytic lesions, osteoporosis, ankylosing spondylitis, spondylarthritis, diffuse idiopathic skeletal hyperostosis, gouty arthritis, and bone disorders related to multiple myeloma.

In some embodiments, the invention provides a method treating allergic and atopic diseases in which activated B cells produce IgE antibodies and mast cells degranulate following engagement of the FcεR leading to release of pro-inflammatory factors and acute activation of local tissue responses as well as chronic changes to endothelial cells, neuroreceptors and other proximal structures which govern organ function. Such conditions include atopic dermatitis, contact dermatitis, eczema, atopic eczema, pemphigus vulgaris, bullous pemphigus, prurigo nodularis, Stevens-Johnson syndrome, asthma, airway hypersensitivity, bronchospasm, bronchitis, reactive asthma, chronic obstructive pulmonary disease, type 1 hypersensitivity, type 2 hypersensitivity, allergic rhinitis, allergic conjunctivitis, and other inflammatory or obstructive disease on airways. Allergies that can be treated or prevented include, among others, allergies to foods, food additives, insect poisons, dust mites, pollen, animal materials, metals, and certain drugs.

In an embodiment, the invention provides a method of suppressing an immune response before or after organ or cell transplantation in a human subject comprising administering to said human subject a therapeutically effective amount of a BTK inhibitor, or a pharmaceutically acceptable salt, cocrystal, ester, prodrug, solvate, hydrate or derivative of the BTK inhibitor. In an embodiment, the invention provides a method of suppressing an immune response before or during organ or cell transplantation in a human subject, wherein the human subject is the donor of the transplant, comprising administering to said human subject a therapeutically effective amount of a BTK inhibitor, or a pharmaceutically acceptable salt, cocrystal, ester, prodrug, solvate, hydrate or derivative of the BTK inhibitor. In an embodiment, the invention provides a method of suppressing an immune response before or after organ or cell transplantation in a human subject, wherein the human subject is the recipient of the transplant, comprising administering to said human subject a therapeutically effective amount of a BTK inhibitor, or a pharmaceutically acceptable salt, cocrystal, ester, prodrug, solvate, hydrate or derivative of the BTK inhibitor. In an embodiment, the invention provides a method of treating patients with high levels of anti-allo-HLA antibodies with a BTK inhibitor prior to transplant to reduce the anti-allo-HLA burden as part of the transplant conditioning treatment. In some embodiments, the invention provides a method of treating patients with a BTK during, or after transplant to reduce de novo generation of anti-allo antibodies. In an embodiment, the invention provides a method of suppressing allograft rejection prior to, during, or after organ or cell transplantation in a human subject comprising administering to said human subject a therapeutically effective amount of a BTK inhibitor, or a pharmaceutically acceptable salt, cocrystal, ester, prodrug, solvate, hydrate or derivative of the BTK inhibitor. In an embodiment, the invention provides a method of the pre-transplant conditioning regimen of patients receiving solid organ transplant using a BTK inhibitor. In an embodiment, the invention provides a method of suppressing humoral acute rejection with a BTK inhibitor prior to, during, or after organ transplantation during the early post-operative stages of engraftment in a human subject comprising administering to said human subject a therapeutically effective amount of a BTK inhibitor, or a pharmaceutically acceptable salt, cocrystal, ester, prodrug, solvate, hydrate or derivative of the BTK inhibitor. In an embodiment, the invention provides a method of suppressing the infiltration of myeloid cells into the tissue allograft by inhibition of BTK prior to, during or after organ transplantation. In an embodiment, the invention provides a method of reducing the physiological changes associated with ischemia/reperfusion in organs following transplantation and thus reducing the pro-inflammatory signals that result in leukocyte migration. In an embodiment, the invention provides a method of inhibiting effective B cell antigen presentation to T lymphocytes during the post-engraftment phase of organ transplantation, and therefore reduces the development of allograft-specific cytotoxic and helper T cell populations, including CD8 T cells, Th1 T cells, Th2 T cells and Th17 T cells, and other pro-inflammatory T cell populations. In an embodiment, the invention provides a method of preventing de novo activation of B cells after transplantation by treatment with a BTK inhibitor at a dose that prevents signaling through the BCR in the compartment described by the transplanted organ. In an embodiment, the invention provides a method of preventing de novo activation of B cells after transplantation by treatment with a BTK inhibitor at a dose that prevents signaling through the BCR in the compartment described by the draining lymph nodes from the transplanted organ. In an embodiment, the invention provides a method of treating acute or chronic graft rejection with a BTK inhibitor after organ transplantation at a dose that prevents signaling through the BCR in the compartment described by the inflamed tissue within the transplanted organ. In any of the foregoing embodiments, the organ or cell transplantation is selected from the group consisting of heart transplantation, renal transplantation, kidney transplantation, lung transplantation, liver transplantation, ABO-incompatible transplantation, and stem cell transplantation. In some embodiments, the invention provides a method of treating a human subject wherein the human subject is a transplant recipient, comprising the step of administering a BTK inhibitor.

In an embodiment, the invention provides a method of treating graft-versus-host disease (GVHD), comprising the step of administering a BTK inhibitor, wherein the GVHD is selected from the group consisting of GVHD associated with stem cell transplant, GVHD associated with bone marrow transplant, thymus GVHD, skin GVHD, gastrointestinal GVHD, liver GVHD, acute GVHD, and chronic GVHD.

In one embodiment, the medicament inhibits neurodegenerative diseases that involve the activation of microglia, recruitment and activation of macrophages, infiltration of inflammatory cells including myeloid cells that require BTK signaling to transmit activation signals, recognize integrins on activated endothelial cells, extravasate, or develop into cytokine and/or chemokine producing cells in situ. The inhibition of BTK by Formula (I) would inhibit disease activity or disease progression by inhibiting neurodegenerative diseases associated with the toxic aggregation of protein, such as accumulation of beta amyloid deposits (amyloid plaque), neurofibrillary tangles, tau aggregation and hyper-phosphorylation, intracytoplasmic inclusion bodies, intracytoplasmic paired helical filaments, polyglucosan inclusions, Papp-Lantos bodies, ubiquitin-containing inclusions, and disorders where inadequate control of protein degradation and/or inability to dispose of mis-folded proteins leads to neurodegeneration. Such diseases include sporadic and familial Alzheimer's disease, mild cognitive impairment, cerebral amyloid angiopathy, Lewy body dementia, Lewy body variant of Alzheimer's disease, Down's syndrome, Huntington's disease, striatonigral degeneration, multiple system atrophy (MSA-P, MSA-C, Shy-Drager syndrome), sporadic or hereditary amyotrophic lateral sclerosis (ALS or Lou Gehrig disease), primary lateral sclerosis, juvenile primary lateral sclerosis, neurodegenerative tauopathies, sporadic or hereditary synucleinopathies, neuronal intranuclear inclusion disease, Parkinson's disease, frontotemporal dementia with Parkinsonism linked to chromosome 17 (FTDP-17).

In an embodiment, the invention relates to a method of treating, with a BTK inhibitor, a neurodegenerative disorder in a mammal wherein the inhibition of inflammatory processes in glial cells, myeloid cells, Schwann cells, oligodendrocytes and other myeloid-derived cell types resident in the CNS is accomplished through its covalent interaction with BTK and inhibition of signaling through the BTK pathway. Administration of Formula (I) would prevent or reduce neurodegeneration by inhibiting immune recognition and inflammatory responses toward misfolded and/or accumulated intracellular proteins due to trinucleotide repeat disorders (polyglutamine diseases), Huntington disease, spinocerebellar ataxia Types 1, 2, 3 (Machado-Joseph disease), 6, 7, and 17; spinal and bulbar muscular atrophy, Dentatorubral-pallidoluysian atrophy, neuronal ceroid lipofucsinoses, frontotemporal dementia (Pick's disease, primary progressive aphasia, and semantic dementia), corticobasal degeneration and progressive supranuclear palsy.

In another embodiment, administration of Formula (I) may be used to inhibit BTK in a mammal and thereby ameliorate inflammation-mediated neuronal death and other neuroinflammatory effects due to sporadic or hereditary prion disease, prion-disorders such as Creutzfeldt-Jakob disease, kuru, Gerstmann-Straussler-Scheinker syndrome, and disorders leading to olivopontocerebellar atrophy, sporadic fatal insomnia, fatal familial insomnia. In the case of familial prion disorders, administration of Formula (I) in a mammal may also be used to prevent and/or delay the occurrence of clinical manifestations of disease, in addition to reducing disease symptoms and slowing disease progression after the onset of clinical signs.

In an embodiment, the invention relates to a method of treating, with a BTK inhibitor, a neuroinflammatory disorder in a mammal that results from CNS ischemia. Treatment with Formula (I) may be used shortly after onset of symptoms and/or imaging that identifies a recent event of CNS ischemia, to prevent microglial activation, inflammatory cell infiltration, vascular permeation and subsequent reperfusion injury by reducing BTK mediated signals in resident cells in the oxygen-deprived tissue. By administering a covalent BTK inhibitor during the hours or days following the ischemic event, the treatment would diminish and/or prevent the neuroinflammatory and neurodegenerative disorders associated with ischemic brain injury, including vascular dementia, mild cognitive impairment, cerebrovascular accident, stroke, transient ischemic attack (mini-stroke), focal brain ischemia, multifocal brain ischemia, thrombotic stroke, embolic stroke, and the development of an infarct or penumbra around an area of restricted or constrained blood flow.

In an embodiment, the invention pertains to a method of treating, with a BTK inhibitor, an autoimmune mediated neurodegenerative disorder in the central and/or peripheral nervous system. Through the inhibition of BTK mediated autoantibody production, Formula (I) may reduce the activation of myeloid derived cells resident in the tissues and inhibit transcytosis, extravasation and infiltration of circulating myeloid cells, thereby reducing inflammation. In addition, treatment with Formula (I) may reduce the activation of inflammatory processes at the endothelial-microglial interface and interstitial spaces, where lymphoid aggregates have been observed in autoimmune neuropathies, by 1) altering cross-talk between microglia and endothelial cells, 2) inhibiting the activation of B lymphocytes and their cognate antigen presentation to circulating or infiltrating T cells, and 3) reducing cytokine and/or chemokine production. These effects of BTK inhibition by covalent interaction with Formula (I) are thought to reduce infiltration of autoimmune T cells into grey matter and white matter, by inhibition of B cell activation, cytokine activation, and APC function, as well as by altering the development and maturation status of professional APCs including infiltrating monocytes, activated microglia, and oligodendrocytes. Thus, the method of treatment for autoimmunity-mediated neurodegenerative disorders with a covalent BTK inhibitor such as Formula (I) may impair disease progression by inhibiting innate immune processes as well as reducing antibody production and the activation of autoimmune T cells. The invention may slow the progression or induce remission of experimental autoimmune encephalopathy in animal models, and in human neuropathies including neuromyelitis optica (Devic's syndrome), Guillain-Barre syndrome, multiple sclerosis, clinically isolated syndrome, relapsing-remitting multiple sclerosis, malignant multiple sclerosis, primary progressive multiple sclerosis, neuromyelitis optica spectrum diseases, Balo concentric sclerosis, Marburg multiple sclerosis, diffuse myelinoclastic sclerosis, chronic focal encephalitis, Rasmussen's encephalitis, stiff person syndrome, myasthenia gravis, polyneuropathy associated with anti-MAG IgM monoclonal gammopathy.

In another embodiment, the invention relates to a method of treating, with a BTK inhibitor, polyneuropathies resulting from infection or post-infection neuroinflammation in a mammal, including Bannworth syndrome (Lyme disease), chronic encephalomyelitis (Lyme disease); post-herpetic neuralgia; HTLV-1 associated myelopathy; progressive multifocal leukoencephalopathy; chronic fatigue syndrome (CFS), systemic exertion intolerance disease (SEID), myalgic encephalomyelitis (ME), post-viral fatigue syndrome (PVFS), chronic fatigue immune dysfunction syndrome (CFIDS); Meniere's disease (vertigo-inner ear endolymph fluid regulation), Guillain-Barre syndrome, amyotrophic lateral sclerosis, progressive bulbar palsy, infantile progressive bulbar palsy (or juvenile progressive bulbar palsy), Bell's palsy, vestibular neuritis, acute disseminated encephalomyelitis, recurrent or multiphasic disseminated encephalomyelitis, and chronic encephalomyelitis.

In some embodiments, the invention relates to a method of treating, with a BTK inhibitor, a heritable neurodegenerative disorder wherein a genetic mutation results in degeneration in peripheral or central nerves, spinal nerves, dorsal root ganglia or particularly in the myelin sheath protecting these structures; and/or causes inflammatory responses secondary to defects of the neurons, Schwann cells, glial cells or astrocytes. Diseases selected from the group consisting of Charcot-Marie-Tooth disease, Dejerine-Sottas disease, hypertrophic interstitial neuropathy, Rett syndrome, lysosomal storage diseases and/or lipid storage disorders (Gaucher disease, Tay-Sachs disease, Neimann-Pick disease Types A, B and C; Farber's disease, GM1 gangliosidosis, GM2 gangliosidosis, mucopolysaccharidoses type I (including Hurler, Hurler-Scheie, and Scheie syndromes), neuronal ceroid lipofucsinoses (Santavuori-Haltia disease, Jansky-Bielschowsky disease, Batten disease, Kufs disease, and other childhood/juvenile neuronal ceroid lipofucsinoses), leukodystrophies (including adrenoleukodystrophy, metachromatic leukodystrophy, Canavan disease, Alexander disease, Pelizaeus-Merzbacher disease); and mitochrondrial dysfunctions such as Friedreich's ataxia chronic progressive external ophthalmoplegia, Alper's disease, spinal muscular atrophy (inherited SMN1 or SMN2 mutation), infantile spinal muscular atrophy (Werdnig-Hoffman disease), juvenile spinal muscular atrophy (Wohlfart-Kugelberg-Welander disease), Arthrogyrposis multiplex congenital, and diseases in which inflammation may lead to loss of motor nerves (long nerves especially) such as hereditary spastic paraplegia.

In some embodiments, the invention relates to a method of treating a solid tumor cancer in a human with a composition including a BTK inhibitor, wherein the dose is effective to inhibit signaling between the solid tumor cells and at least one microenvironment selected from the group consisting of macrophages, monocytes, mast cells, helper T cells, cytotoxic T cells, regulatory T cells, natural killer cells, myeloid-derived suppressor cells, regulatory B cells, neutrophils, dendritic cells, and fibroblasts. In selected embodiments, the invention relates to a method of treating pancreatic cancer, breast cancer, ovarian cancer, melanoma, lung cancer, head and neck cancer, and colorectal cancer using a BTK inhibitor, wherein the dose is effective to inhibit signaling between the solid tumor cells and at least one microenvironment selected from the group consisting of macrophages, monocytes, mast cells, helper T cells, cytotoxic T cells, regulatory T cells, natural killer cells, myeloid-derived suppressor cells, regulatory B cells, neutrophils, dendritic cells, and fibroblasts.

In some embodiments, the hyperproliferative disorder is a solid tumor cancer selected from the group consisting of bladder cancer, squamous cell carcinoma, head and neck cancer, pancreatic ductal adenocarcinoma (PDA), pancreatic cancer, colon carcinoma, mammary carcinoma, breast cancer, fibrosarcoma, mesothelioma, renal cell carcinoma, lung carcinoma, thyoma, prostate cancer, colorectal cancer, ovarian cancer, acute myeloid leukemia, thymus cancer, brain cancer, squamous cell cancer, skin cancer, eye cancer, retinoblastoma, melanoma, intraocular melanoma, oral cavity cancer, oropharyngeal cancer, gastric cancer, stomach cancer, cervical cancer, renal cancer, kidney cancer, liver cancer, ovarian cancer, prostate cancer, colorectal cancer, esophageal cancer, testicular cancer, gynecological cancer, thyroid cancer, acquired immune deficiency syndrome (AIDS)-related cancers (e.g., lymphoma and Kaposi's sarcoma), viral-induced cancers such as cervical carcinoma (human papillomavirus), B-cell lymphoproliferative disease, nasopharyngeal carcinoma (Epstein-Barr virus), Kaposi's sarcoma and primary effusion lymphomas (Kaposi's sarcoma herpesvirus), hepatocellular carcinoma (hepatitis B and hepatitis C viruses), and T-cell leukemias (Human T-cell leukemia virus-1), glioblastoma, esophogeal tumors, head and neck tumor, metastatic colon cancer, head and neck squamous cell carcinoma, ovary tumor, pancreas tumor, renal cell carcinoma, hematological neoplasms, small-cell lung cancer, non-small-cell lung cancer, stage IV melanoma, and glioma.

In some embodiments, the hyperproliferative disorder is a B cell hematological malignancy selected from the group consisting of chronic lymphocytic leukemia (CLL), small lymphocytic leukemia (SLL), non-Hodgkin's lymphoma (NHL), diffuse large B cell lymphoma (DLBCL), follicular lymphoma (FL), mantle cell lymphoma (MCL), Hodgkin's lymphoma, B cell acute lymphoblastic leukemia (B-ALL), Burkitt's lymphoma, Waldenstrom's macroglobulinemia (WM), Burkitt's lymphoma, multiple myeloma, myelodysplastic syndromes, or myelofibrosis. In an embodiment, the invention relates to a method of treating a cancer in a mammal, wherein the cancer is chronic myelocytic leukemia, acute myeloid leukemia, DLBCL (including activated B-cell (ABC) and germinal center B-cell (GCB) subtypes), follicle center lymphoma, Hodgkin's disease, multiple myeloma, indolent non-Hodgkin's lymphoma, and mature B-cell ALL.

In some embodiments, the hyperproliferative disorder is a subtype of CLL. A number of subtypes of CLL have been characterized. CLL is often classified for immunoglobulin heavy-chain variable-region (IgVH) mutational status in leukemic cells. R. N. Damle, et al., *Blood* 1999, 94, 1840-47; T. J. Hamblin, et al., *Blood* 1999, 94, 1848-54. Patients with IgVH mutations generally survive longer than patients without IgVH mutations. ZAP70 expression (positive or negative) is also used to characterize CLL. L. Z. Rassenti, et al., *N. Engl. J. Med.* 2004, 351, 893-901. The methylation of ZAP-70 at CpG3 is also used to characterize CLL, for example by pyrosequencing. R. Claus, et al., *J. Clin. Oncol.* 2012, 30, 2483-91; J. A. Woyach, et al., *Blood* 2014, 123, 1810-17. CLL is also classified by stage of disease under the Binet or Rai criteria. J. L. Binet, et al., *Cancer* 1977, 40, 855-64; K. R. Rai, T. Han, *Hematol. Oncol. Clin. North Am.* 1990, 4, 447-56. Other common mutations, such as 11q deletion, 13q deletion, and 17p deletion can be assessed using well-known techniques such as fluorescence in situ hybridization (FISH). In an embodiment, the invention relates to a method of treating a CLL in a human, wherein the CLL is selected from the group consisting of IgVH mutation negative CLL, ZAP-70 positive CLL, ZAP-70 methylated at CpG3 CLL, CD38 positive CLL, chronic lymphocytic leukemia characterized by a 17p13.1 (17p) deletion, and CLL characterized by a 11q22.3 (11q) deletion.

In some embodiments, the hyperproliferative disorder is a CLL wherein the CLL has undergone a Richter's transformation. Methods of assessing Richter's transformation, which is also known as Richter's syndrome, are described in P. Jain and S. O'Brien, *Oncology*, 2012, 26, 1146-52. Richter's transformation is a subtype of CLL that is observed in 5-10% of patients. It involves the development of aggressive lymphoma from CLL and has a generally poor prognosis.

In some embodiments, the hyperproliferative disorder is a CLL or SLL in a patient, wherein the patient is sensitive to lymphocytosis. In an embodiment, the invention relates to a method of treating CLL or SLL in a patient, wherein the patient exhibits lymphocytosis caused by a disorder selected from the group consisting of a viral infection, a bacterial infection, a protozoal infection, or a post-splenectomy state. In an embodiment, the viral infection in any of the foregoing embodiments is selected from the group consisting of infectious mononucleosis, hepatitis, and cytomegalovirus. In an embodiment, the bacterial infection in any of the foregoing embodiments is selected from the group consisting of pertussis, tuberculosis, and brucellosis.

In some embodiments, the hyperproliferative disorder is selected from the group consisting of myeloproliferative disorders (MPDs), myeloproliferative neoplasms, polycythemia vera (PV), essential thrombocythemia (ET), primary myelofibrosis (PMF), myelodysplastic syndrome, chronic myelogenous leukemia (BCR-ABL 1-positive), chronic neutrophilic leukemia, chronic eosinophilic leukemia, or mastocytosis.

In some embodiments, the inflammatory, immune, or autoimmune disorder is selected from the group consisting of tumor angiogenesis, chronic inflammatory disease, rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma and melanoma, ulcerative colitis, atopic dermatitis, pouchitis, spondylarthritis, uveitis, Behcet's disease, polymyalgia rheumatica, giant-cell arteritis, sarcoidosis, Kawasaki disease, juvenile idiopathic arthritis, hidratenitis suppurativa, Sjögren's syndrome, psoriatic arthritis, juvenile rheumatoid arthritis, ankylosing spondylitis, Crohn's disease, lupus, and lupus nephritis.

In some embodiments, the inflammatory, immune, or autoimmune disorder is a disease related to vasculogenesis or angiogenesis in a mammal which can manifest as tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

In some embodiments, the inflammatory, immune, or autoimmune disorder is the treatment, prevention, and/or management of asthma. As used herein, "asthma" encompasses airway constriction regardless of the cause, including reactive airway disease. Common triggers of asthma include, but are not limited to, exposure to an environmental stimulants (e.g., allergens), cold air, warm air, perfume, moist air, exercise or exertion, and emotional stress. Also provided herein is a method of treating, preventing and/or managing one or more symptoms associated with asthma. Examples of the symptoms include, but are not limited to, severe coughing, airway constriction, and mucus production.

Efficacy of the compounds and combinations of compounds described herein in treating, preventing and/or managing other indicated diseases or disorders described here can also be tested using various models known in the art. Efficacy in treating, preventing and/or managing asthma can be assessed using the ova induced asthma model described, for example, in Lee, et al., J. Allergy Clin. Immunol. 2006, 118, 403-9. Efficacy in treating, preventing and/or managing arthritis (e.g., rheumatoid or psoriatic arthritis) can be assessed using the autoimmune animal models described in, for example, Williams, et al., Chem. Biol. 2010, 17, 123-34, WO 2009/088986, WO 2009/088880, and WO 2011/008302. Efficacy in treating, preventing and/or managing psoriasis can be assessed using transgenic or knockout mouse model with targeted mutations in epidermis, vasculature or immune cells, mouse model resulting from spontaneous mutations, and immuno-deficient mouse model with xenotransplantation of human skin or immune cells, all of which are described, for example, in Boehncke, et al., Clinics in Dermatology, 2007, 25, 596-605. Efficacy in treating, preventing and/or managing fibrosis or fibrotic conditions can be assessed using the unilateral ureteral obstruction model of renal fibrosis, which is described, for example, in Chevalier, et al., Kidney International 2009, 75, 1145-1152; the bleomycin induced model of pulmonary fibrosis described in, for example, Moore, et al., Am. J. Physiol. Lung. Cell. Mol. Physiol. 2008, 294, L152-L160; a variety of liver/biliary fibrosis models described in, for example, Chuang, et al., Clin. Liver Dis. 2008, 12, 333-347 and Omenetti, et al., Laboratory Investigation, 2007, 87, 499-514 (biliary duct-ligated model); or any of a number of myelofibrosis mouse models such as described in Varicchio, et al., Expert Rev. Hematol. 2009, 2, 315-334. Efficacy in treating, preventing and/or managing scleroderma can be assessed using a mouse model induced by repeated local injections of bleomycin described, for example, in Yamamoto, et al., J. Invest. Dermatol. 1999, 112, 456-462. Efficacy in treating, preventing and/or managing dermatomyositis can be assessed using a myositis mouse model induced by immunization with rabbit myosin as described, for example, in Phyanagi, et al., Arthritis & Rheumatism, 2009, 60(10), 3118-3127. Efficacy in treating, preventing and/or managing lupus can be assessed using various animal models described, for example, in Ghoreishi, et al., Lupus, 2009, 19, 1029-1035; Ohl, et al., J. Biomed. & Biotechnol., Article ID 432595 (2011); Xia, et al., Rheumatology, 2011, 50, 2187-2196; Pau, et al., PLoS ONE, 2012, 7(5), e36761; Mustafa, et al., Toxicology, 2011, 90, 156-168; Ichikawa et al., Arthritis & Rheumatism, 2012, 62(2), 493-503; Rankin, et al., J. Immunology, 2012, 188, 1656-1667. Efficacy in treating, preventing and/or managing Sjögren's syndrome can be assessed using various mouse models described, for example, in Chiorini, et al., J Autoimmunity, 2009, 33, 190-196.

Efficacy of the compounds and combinations of compounds described herein in treating, preventing and/or managing the indicated diseases or disorders can be tested using various models known in the art. For example, models for determining efficacy of treatments for pancreatic cancer are described in Herreros-Villanueva, et al., World J. Gastroenterol. 2012, 18, 1286-1294. Models for determining efficacy of treatments for breast cancer are described, e.g., in Fantozzi, Breast Cancer Res. 2006, 8, 212. Models for determining efficacy of treatments for ovarian cancer are described, e.g., in Mullany, et al., Endocrinology 2012, 153, 1585-92; and Fong, et al., J. Ovarian Res. 2009, 2, 12. Models for determining efficacy of treatments for melanoma are described, e.g., in Damsky, et al., Pigment Cell & Melanoma Res. 2010, 23, 853-859. Models for determining efficacy of treatments for lung cancer are described, e.g., in Meuwissen, et al., Genes & Development, 2005, 19, 643-664. Models for determining efficacy of treatments for lung cancer are described, e.g., in Kim, Clin. Exp. Otorhinolaryngol. 2009, 2, 55-60; and Sano, Head Neck Oncol. 2009, 1, 32. Models for determining efficacy of treatments for colorectal cancer, including the CT26 model, are described in Castle, et al., BMC Genomics, 2013, 15, 190; Endo, et al., Cancer Gene Therapy, 2002, 9, 142-148; Roth et al., Adv. Immunol. 1994, 57, 281-351; Fearon, et al., Cancer Res. 1988, 48, 2975-2980.

Models for determining efficacy of treatments in hematological malignancies, including B cell cancers, may also be used. For example, efficacy in diffuse large B cell lymphoma (DLBCL) may be assessed using the PiBCL1 murine model and BALB/c (haplotype H-2d) mice. Illidge, et al., Cancer Biother. & Radiopharm. 2000, 15, 571-80. Efficacy in non-Hodgkin's lymphoma (NHL) may be assessed using the 38C13 murine model with C3H/HeN (haplotype 2-Hk) mice or alternatively the 38C13 Her2/neu model. Timmerman, et al., Blood 2001, 97, 1370-77; Penichet, et al., Cancer Immunolog. Immunother. 2000, 49, 649-662. Efficacy in CLL may be assessed using the BCL1 model using BALB/c (haplotype H-2d) mice. Dutt, et al., Blood, 2011, 117, 3230-29.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein. Reagents described in the examples are commercially available or may be prepared according to procedures described in the literature.

The following abbreviations are used:
HATU O-(7-Azabenzotriazol-1-yl)-1,1,3,3-tetramethyluroniumhexafluoro phosphate
$POCl_3$ Phosphorus(V) oxychloride
DMF N,N-Dimethylformamide
NBS N-Bromosuccinimide
DCM Dichloromethane
EtOAc Ethyl acetate
KOAc Potassium acetate
IPA 2-Propanol ACN Acetonitrile
MW Microwave
AcOH Acetic acid
DIPEA N,N-Diisopropylethylamine
THF Tetrahydrofuran
EtOH Ethanol
EDCI 1-(3-Dimethylaminopropyl)-3-ethylcarbodiimide
DMAP Dimethylamino pyridine
HPLC High pressure liquid chromatography
LiHMDS Lithium hexamethyldisilazide
MeOH Methanol
n-BuLi n-Butyllithium
NMR Nuclear magnetic resonance
LC-MS Liquid chromatography—mass spectrometry
SCX-2 Strong cation exchange-2
KOtBu Potassium tert. butoxide
T3P Propylphosphonic anhydride
RT Room temperature
Rt Retention time
NMP 1-Methyl-2-pyrrolidinone
TFA Trifluoroacetic acid
DMSO Dimethyl sulfoxide
DIAD Diisopropyl azodicarboxylate
THP Tetrahydropyran
TBDMS tert-Butyldimethylsilyl
TEA Triethylamine
Pd$_2$(dba)$_3$ Tris(dibenzylideneacetone)dipalladium(0)
PdCl$_2$(dppf).DCM [1,1'-Bis(diphenylphosphino)ferrocene]dichloropalladium(II), complex with dichloromethane
TLC Thin layer chromatography
PE Phase exchange
CDCl$_3$ Chloroform-d
HBr Hydrogen bromide
K$_2$CO$_3$ Potassium carbonate
m/z Mass-to-charge ratio Example 1—Synthesis of BTK Inhibitors The BTK inhibitors included in the present invention can be prepared by methods well known in the art of organic chemistry. See, for example, March, *Advanced Organic Chemistry*, 4th Edition, John Wiley & Sons, 2001. During synthetic processes it may be necessary and/or desirable to protect sensitive or reactive groups on any of the molecules concerned. This is achieved by means of conventional protecting groups, such as those described in Greene and Wutts, *Protective Groups in Organic Synthesis*, 3rd Edition, John Wiley & Sons, 1999. The protective groups are optionally removed at a convenient subsequent stage using methods well known in the art.

The products of the reactions are optionally isolated and purified, if desired, using conventional techniques, but not limited to, filtration, distillation, crystallization, chromatography and the like. Such materials are optionally characterized using conventional means, including the measurement of physical constants and spectral data.

BTK inhibitors included in the present invention may be synthesized by the following routes. Boronic acid pinacol esters may be prepared as follows:

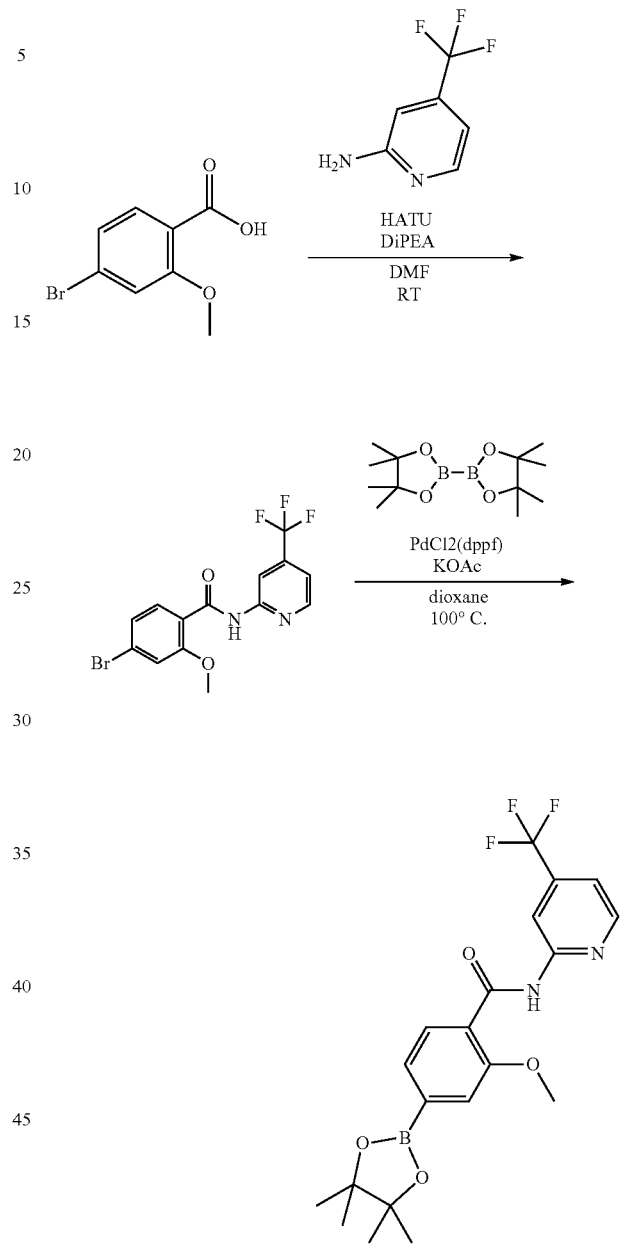

Scheme 1

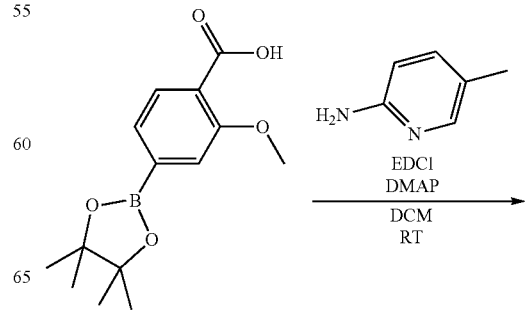

Scheme 2

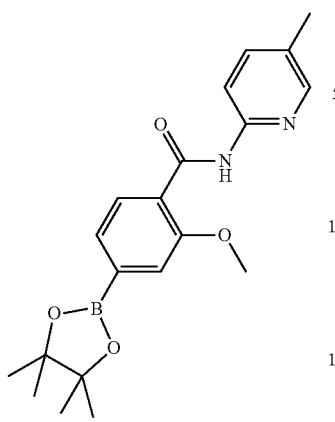
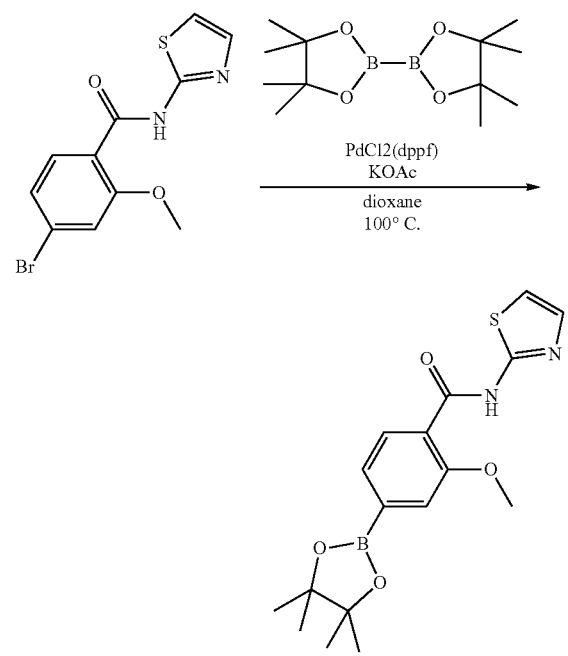
The following compound may be prepared in an analogous manner to the preparations shown in Scheme 1 and Scheme 2:
Scheme 3
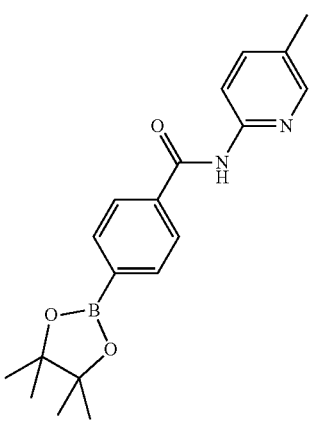
Additional boronic acid pinacol esters may be prepared as follows:
Scheme 4
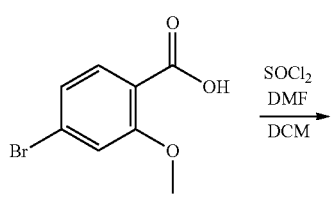
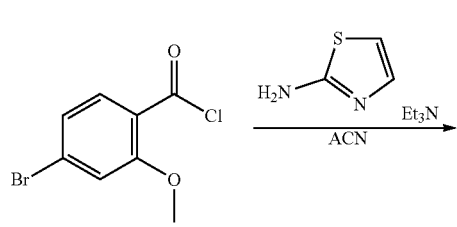
Boronic acids may be prepared as follows:
Scheme 5
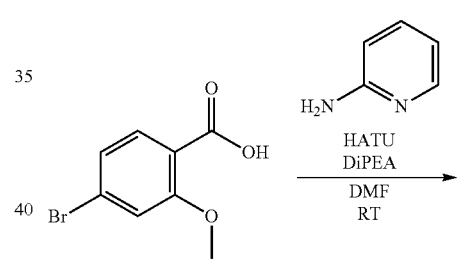
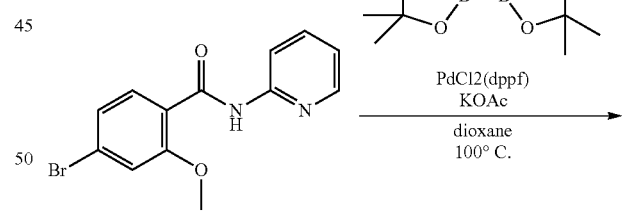
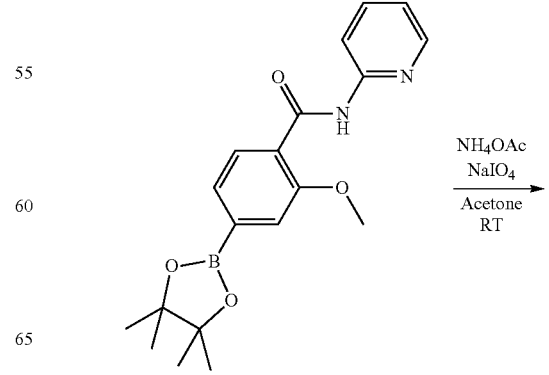

-continued
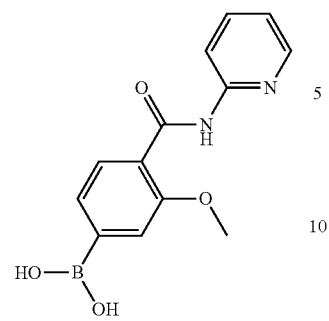
Pyrollidine derivatives may be prepared as follows (wherein CBz refers to carboxybenzyl):
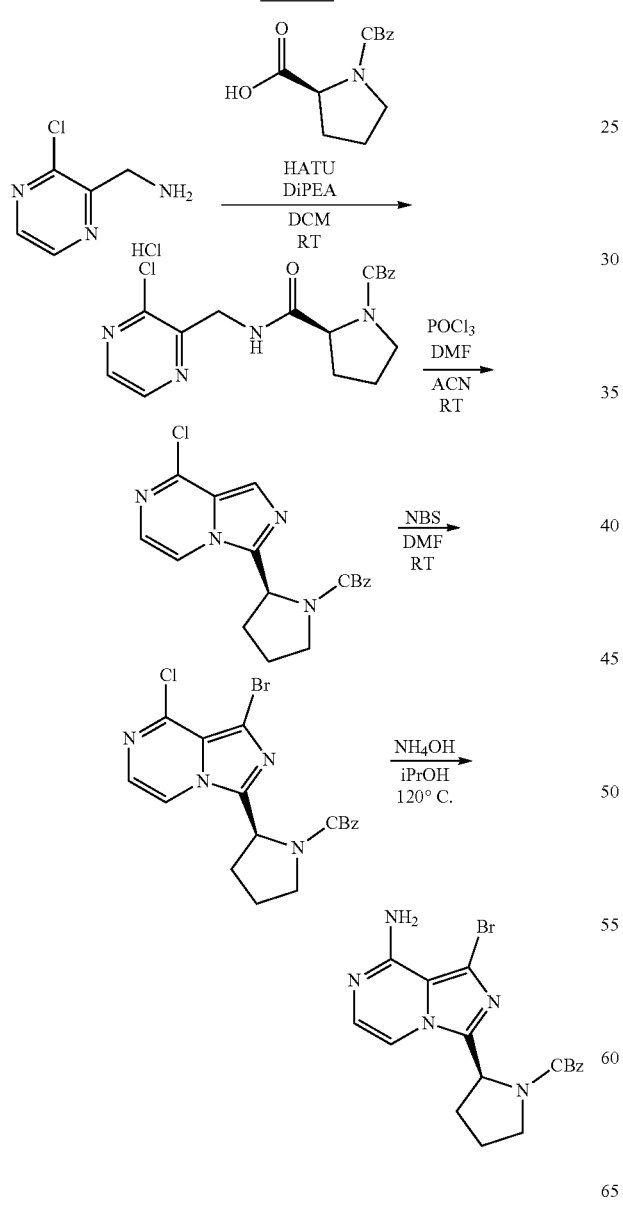
CBz-protected alanine and N-methylalanine derivatives are prepared in an analogous manner.
Pyrollidine derivatives may be also prepared as follows:
Scheme 7
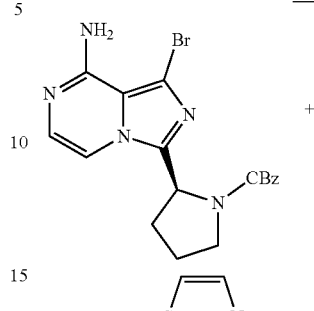
+
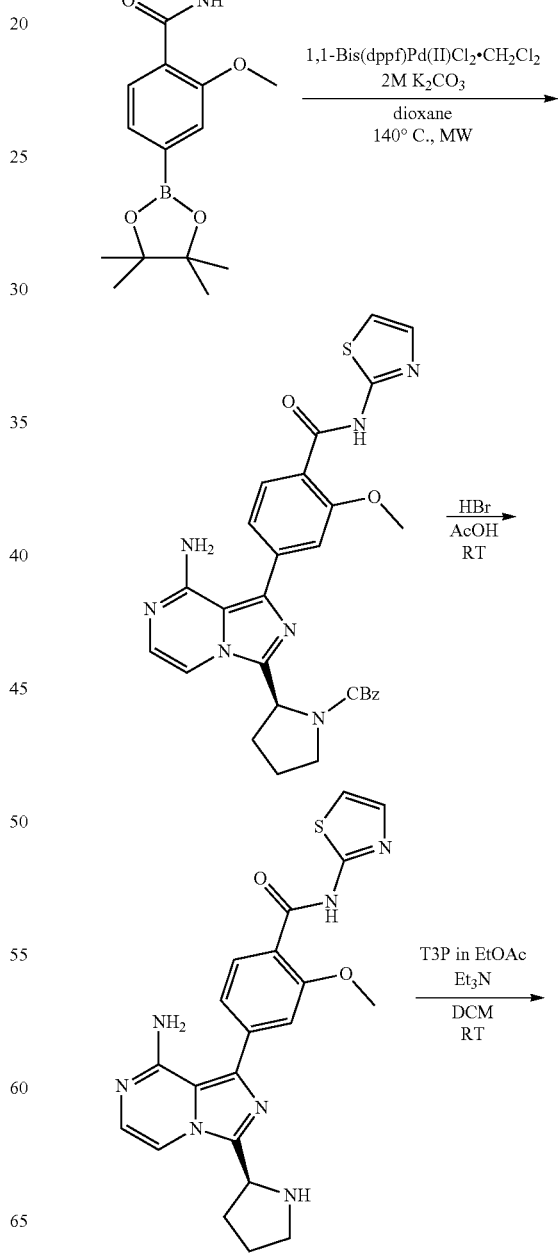

-continued

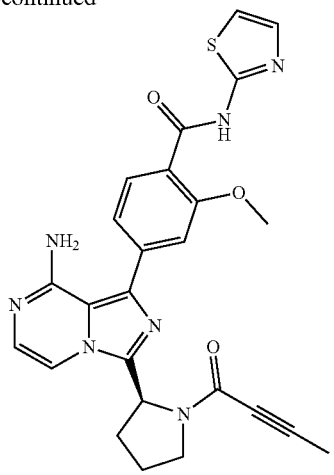

In the aforementioned syntheses, boronic acids and boronic acid pinacol esters perform equally well in the Suzuki coupling step.

The present invention also includes within its scope all stereoisomeric forms of the BTK inhibitors according to the present invention resulting, for example, because of configurational or geometrical isomerism. Such stereoisomeric forms include enantiomers, diastereoisomers, cis and trans isomers, etc. In the case of the individual stereoisomers of compounds described herein, the present invention also includes the aforementioned stereoisomers substantially free, i.e., associated with less than 5%, preferably less than 2% and in particular less than 1% of the other stereoisomer. Mixtures of stereoisomers in any proportion, for example a racemic mixture comprising substantially equal amounts of two enantiomers are also included within the scope of the present invention.

For chiral compounds, methods for asymmetric synthesis whereby the pure stereoisomers are obtained are well known in the art, e.g. synthesis with chiral induction, synthesis starting from chiral intermediates, enantioselective enzymatic conversions, separation of stereoisomers using chromatography on chiral media. Such methods are described in Collins, et al., eds., *Chirality in Industry*, John Wiley & Sons, 1992. Likewise, methods for synthesis of geometrical isomers are also well known in the art.

The compounds of the present invention, which can be in the form of a free base, may be isolated from the reaction mixture in the form of a pharmaceutically acceptable salt. The pharmaceutically acceptable salts may also be obtained by treating the free base of the BTK inhibitors disclosed herein with an organic or inorganic acid such as hydrogen chloride, hydrogen bromide, hydrogen iodide, sulfuric acid, phosphoric acid, acetic acid, propionic acid, glycolic acid, maleic acid, malonic acid, methanesulphonic acid, fumaric acid, succinic acid, tartaric acid, citric acid, benzoic acid, and ascorbic acid.

The compounds of the present invention disclosed herein may also exist as amorphous forms or as multiple crystalline forms, also known as polymorphic forms. All physical forms are included within the scope of the present invention. Preparation of solvates is generally known. Thus, for example, Caira, et al., *J. Pharm. Sci.*, 2004, 93, 601-611 describe the preparation of the solvates of the antifungal fluconazole in ethyl acetate as well as from water. Similar preparations of solvates, hydrates and the like are described by van Tonder, et al., *AAPS PharmSciTech.*, 2004, 5(1), article 12; and Bingham, et al., *Chem. Commun.* 2001, 603-604. A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example IR spectroscopy, show the presence of the solvent (or water) in the crystals as a solvate (or hydrate).

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{17}$O, $^{18}$O, $^{18}$F, $^{32}$P, $^{35}$S, and $^{36}$Cl, respectively.

Radioisotopically-labelled forms of the compounds disclosed herein (e.g., those labeled with $^3$H and $^{14}$C) are useful in compound and/or substrate tissue distribution assays. Tritium ($^3$H) and carbon-14 ($^{14}$C) isotopes are particularly preferred for their ease of preparation and detectability. Further, substitution with heavier isotopes such as deuterium ($^2$H) may afford certain therapeutic advantages resulting from greater metabolic stability (e.g., increased in vivo half-life or reduced dosage requirements) and hence may be preferred in some circumstances. Isotopically-labelled forms of the compounds disclosed herein can generally be prepared by following procedures analogous to those disclosed in the Schemes and/or in the Examples described below, by substituting an appropriate isotopically labeled reagent for a non-isotoplically labeled reagent.

Example 2—Analytical Methods

The following liquid chromatography (LC) and mass spectrometry (MS) methods may be used to characterize compounds included in the present invention.

Method A
LC-MS spectrometer (Agilent)
Detector: DAD (210, 254 and 280 nm)
Mass detector: API-ES (10-2000 amu, pos./neg. ion mode)
Eluents (mobile phase): A: 0.1% formic acid in MilliQ-water, B: acetonitrile
Column: Waters XTerra C18 MS, 50×4.6 mm ID, 2.5 m
Flow rate: 0.5 mL/min
Gradient elution program:

| Time (min) | A (%) | B (%) |
|---|---|---|
| 0.0 | 90 | 10 |
| 7.0 | 10 | 90 |
| 7.1 | 0 | 100 |
| 10.0 | 90 | 10 |

Method B
LC-MS spectrometer (Waters); Detector: DAD (214 nm)
Mass detector: API-ES (100-1000 amu, pos./neg. ion mode)
Eluents (mobile phase): A: 0.1% trifluoroacetic acid (TFA) in water; B: acetonitrile LC-MS flow method: Gradient
Column: Acquity HSS-T3 (2.1×100 mm×1.8 m)
Flow rate: 0.3 mL/min
Gradient elution program:

| Time (min) | A (%) | B (%) |
|---|---|---|
| 0.0 | 90.0 | 10.0 |
| 1.0 | 90.0 | 10.0 |
| 2.0 | 85.0 | 15.0 |
| 4.5 | 45.0 | 55.0 |
| 6.0 | 10.0 | 90.0 |
| 8.0 | 10.0 | 90.0 |
| 9.0 | 90.0 | 10.0 |
| 10.0 | 90.0 | 10.0 |

Method C
HPLC: Gilson analytical HPLC system
Column: Phenomenex Luna C18(2) (100×2.00 mm, 5 m)
Detector: UV/Vis (210/240 nm)
Flow rate: 1 mL/min
Eluents (mobile phase): A: acetonitrile, B: acetonitrile/MilliQ-water=1/9 (v/v), C: 0.1% TFA in MilliQ-water
Gradient elution program:

| Time (min) | A (%) | B (%) | C (%) |
|---|---|---|---|
| 0.00 | 0 | 97 | 3 |
| 11.90 | 97 | 0 | 3 |
| 14.40 | 97 | 0 | 3 |
| 15.40 | 0 | 97 | 3 |

Method D
HPLC: Waters analytical HPLC system; Column: SunFire-C18 (4.6×50 mm, 5 m)
Detector: UV/Vis (210/240 nm)
Flow: 1 mL/min
Eluents (mobile phase): A: 5 mM ammonium acetate in water, B: Acetonitrile
Gradient elution program:

| Time (min) | A (%) | B (%) |
|---|---|---|
| 0.0 | 90 | 10 |
| 1.5 | 90 | 10 |
| 6.0 | 10 | 90 |
| 8.0 | 10 | 90 |
| 8.5 | 90 | 10 |
| 10.0 | 90 | 10 |

Method E
HPLC: Waters analytical HPLC system; Column: X-Bridge Shield-RP-18 (4.6×250 mm, 5 m)
Detector: programmable diode array
Flow: 1 mL/min
Eluents: A: 2 mM ammonium acetate in water, B: Acetonitrile
Gradient elution program:

| Time (min) | A (%) | B (%) |
|---|---|---|
| 0.0 | 70 | 30 |
| 1.0 | 70 | 30 |
| 3.5 | 20 | 80 |
| 5.5 | 5 | 95 |
| 7.0 | 5 | 95 |
| 8.5 | 70 | 30 |
| 10.0 | 70 | 30 |

Example 3—Preparation of 2-Methoxy-4-(4,4,5,5-tetramethyl-1,3,2-dioxaborolan-2-yl)-N-[4-(trifluoromethyl)-2-pyridyl]benzamide (I-1)

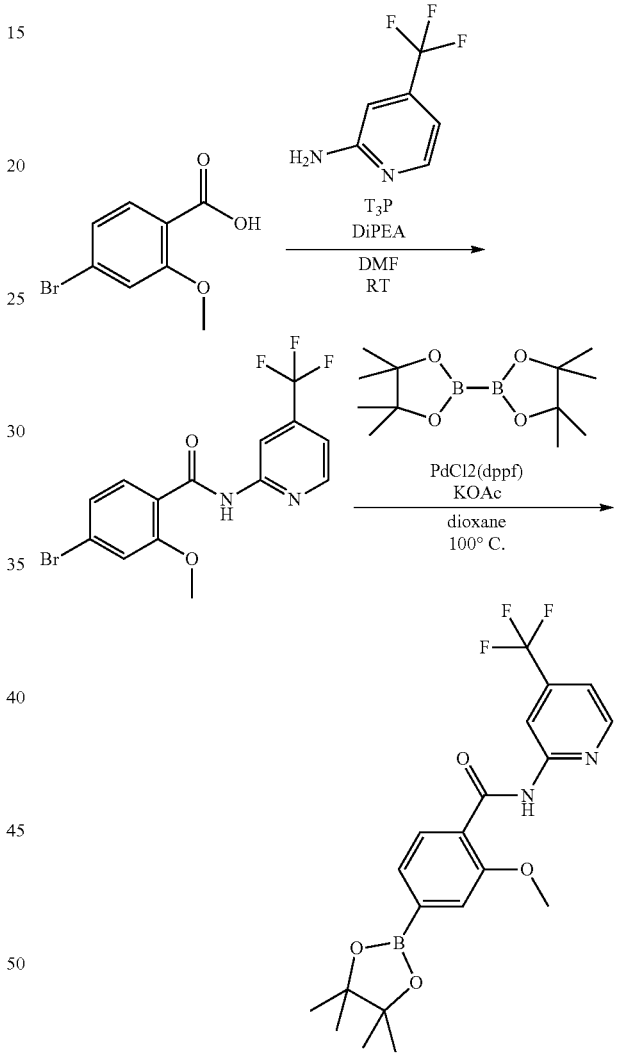

I-1

Preparation of 4-bromo-2-methoxy-N-[4-(trifluoromethyl)-2-pyridyl]benzamide. A solution of 4-(trifluoromethyl)pyridin-2-amine (13.0 g, 80.1 mmol) and 4-bromo-2-methoxy-benzoic acid (18.5 g, 80.1 mmoles) in DMF (150 mL) was cooled to 0° C., N,N-diisopropylethylamine (44.2 mL, 240.3 mmol) was added, then propylphosphonic anhydride solution (50% in dichloromethane, 76.4 g, 120.1 mmol) was added drop wise and the reaction mixture was heated at 80° C. for 16 hours. The reaction mixture was cooled and diluted with water (300 mL). The solid obtained was filtered off and washed with water (300 mL). This solid was dissolved in 10% methanol in dichloromethane (200 mL) and washed with water. The organic part was dried over sodium sulfate, filtered and concentrated to give 4-bromo-2-methoxy-N-[4-(trifluoromethyl)-2-pyridyl]benzamide (17.0 g, 56.8%) as light brown solid.

Preparation of 2-methoxy-4-(4,4,5,5-tetramethyl-1,3,2-dioxaborolan-2-yl)-N-[4-(trifluoromethyl)-2-pyridyl]benzamide. 4-bromo-2-methoxy-N-[4-(trifluoromethyl)-2-pyridyl]benzamide (17.0 g, 45.3 mmol), bis(pinacolato)diboron (13.7 g, 54.3 mmol) and potassium acetate (8.8 g, 90.6 mmol) was taken up in dioxane (170 mL) and the reaction mixture was degassed under nitrogen for 10 minutes. Then, PdCl$_2$(dppf)$_2$.DCM (1.7 g, 2.2 mmol) was added and the reaction mixture was heated at 100° C. for 16 hours. The reaction mixture was cooled, water (300 mL) was added to this mixture and extracted with ethyl acetate (200 mL). The organic part was dried over sodium sulfate, filtered and concentrated to give a residue which was further purified by column chromatography using silica gel (100-200 mesh) and 0-10% ethyl acetate in hexane to give 2-methoxy-4-(4,4,5,5-tetramethyl-1,3,2-dioxaborolan-2-yl)-N-[4-(trifluoromethyl)-2-pyridyl]benzamide (14.4 g, 77.0%) as an off white solid. HPLC (Method E) R$_t$: 5.99 min; $^1$H NMR (400 MHz, DMSO-d$_6$, 300 K): 10.9 (1H, s), 8.64 (1H, d, J=4.8 Hz), 8.56 (1H, s), 7.83 (d, 1H, J=7.6 Hz), 7.54 (d, 1H, J=4.8 Hz), 7.41-7.37 (m, 2H), 3.98 (s, 3H) and 1.32 (s, 12H).

Example 4—Preparation of benzyl N-[(1S)-1-(8-amino-1-bromo-imidazo[1,5-a]pyrazin-3-yl)ethyl]-N-methyl-carbamate (I-2)

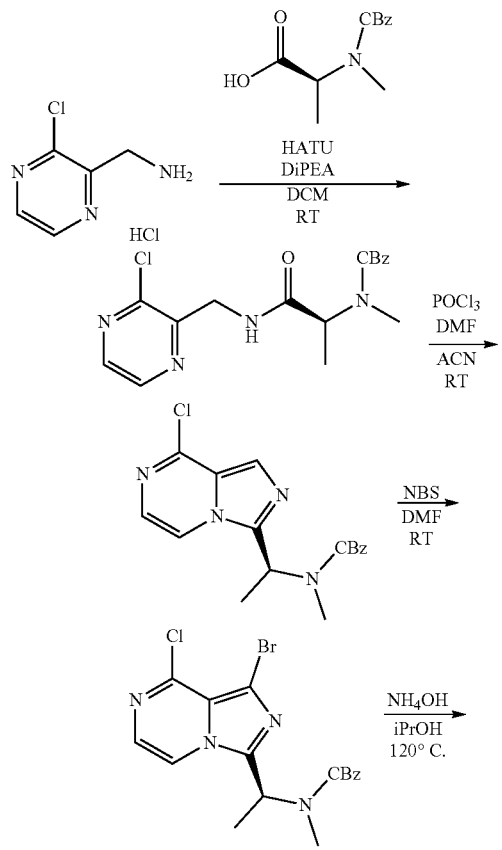

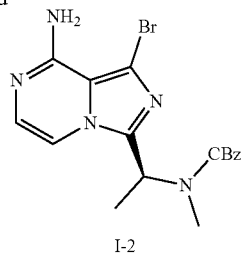

I-2

Preparation of benzyl N-[(1S)-2-[(3-chloropyrazin-2-yl)methylamino]-1-methyl-2-oxo-ethyl]-N-methyl-carbamate. N,N-Diisopropylethylamine (19.35 mL, 111.09 mmol) was added dropwise in ten minutes to a mixture of (2S)-2-[benzyloxycarbonyl(methyl)amino]propanoic acid (6.59 g, 27.77 mmol), (3-chloropyrazin-2-yl)methanamine hydrochloride (5.00 g, 27.77 mmol) and HATU (15.84 g, 41.66 mmol) in dichloromethane (250 mL) and the resulting mixture was stirred for three hours at 20° C. The mixture was washed once with aq. sat. sodium bicarbonate solution (200 mL) and once with aq. sat. ammonium chloride solution (200 mL). The organic layer was dried over sodium sulfate, filtered and evaporated to dryness. The residue was purified by flash column chromatography on silica gel (0-100% ethyl acetate in heptane) to give benzyl N-[(1S)-2-[(3-chloropyrazin-2-yl)methylamino]-1-methyl-2-oxo-ethyl]-N-methyl-carbamate (9.2 g, 91.3%) as a colorless oil. Data: LC-MS (Method A) R$_t$: 5.32 min; m/z 363.2 (M+H)$^+$.

Preparation of benzyl N-[(1S)-1-(8-chloroimidazo[1,5-a]pyrazin-3-yl)ethyl]-N-methyl-carbamate. POCl$_3$ (14.22 mL, 152.15 mmol) was added drop wise over 5 minutes at room temperature to a solution of benzyl N-[(1S)-2-[(3-chloropyrazin-2-yl)methylamino]-1-methyl-2-oxo-ethyl]-N-methyl-carbamate (9.2 g, 25.36 mmol) and DMF (0.2 mL, 2.54 mmol) in acetonitrile (200 mL) and the mixture was stirred for 2 hours at 70° C. The reaction mixture was cooled to room temperature and poured into ice (250 mL). The mixture was made pH-8 with sodium carbonate and extracted twice with ethyl acetate (250 mL). The combined organic extracts were washed once with brine (200 mL), dried over sodium sulfate and concentrated in vacuo. The residue was purified by flash column chromatography (100% ethyl acetate) to give benzyl N-[(1S)-1-(8-chloroimidazo[1,5-a]pyrazin-3-yl)ethyl]-N-methyl-carbamate (8.0 g, 91.5%) as an orange oil. Data: LC-MS (Method A) R$_t$: 6.18 min; m/z 345.1 (M+H)+.

Preparation of benzyl N-[(1S)-1-(1-bromo-8-chloro-imidazo[1,5-a]pyrazin-3-yl)ethyl]-N-methyl-carbamate. NBS (4.54 g, 25.52 mmol) was added to a solution of benzyl N-[(1S)-1-(8-chloroimidazo[1,5-a]pyrazin-3-yl)ethyl]-N-methyl-carbamate (8.0 g, 23.2 mmol) in NMP (50 mL) and the mixture was stirred for two hours at room temperature. Ethyl acetate (250 mL) and sat. aqueous sodium bicarbonate (250 mL) were added to the reaction mixture and the layers were separated. The organic extract was washed once with water (200 mL) and once with sat. brine (200 mL), dried over sodium sulfate, filtered and concentrated. The residue was purified by flash column chromatography (0 to 100% ethyl acetate in heptane) to give benzyl N-[(1S)-1-(1-bromo-8-chloro-imidazo[1,5-a]pyrazin-3-yl)ethyl]-N-methyl-carbamate (6.5 g, 66.1%) as a white solid. Data: LC-MS (Method A) R$_t$: 7.05 min; m/z 423.0+425.0 (1:1) (M+H)$^+$.

Preparation of benzyl N-[(1S)-1-(8-amino-1-bromo-imidazo[1,5-a]pyrazin-3-yl)ethyl]-N-methyl-carbamate. In two microwave vials (1×0.9 g; 1×1.3 g) benzyl-N-[(1S)-1-(1- bromo-8-chloro-imidazo[1,5-a]pyrazin-3-yl)ethyl]-N-methyl-carbamate (2.2 g, 5.19 mmol) was suspended in IPA (2×12 mL), ammonium hydroxide (28% in water) (2×8 mL, 410.84 mmol) was added and the mixtures were heated in the microwave for 2 hours at 120° C. The reaction mixtures were pooled and concentrated to a small volume. The solids were filtered off, washed with water (50 mL) and coevaporated once with acetonitrile (25 mL) to give the title compound (1.8 g, 85.8% yield) as a yellow solid. Data: LC-MS (Method A) $R_t$: 4.27 min; m/z 404.1+406.1 (1:1) (M+H)⁺.

Example 5—Preparation of 4-[8-amino-3-[(1S)-1-(methylamino)ethyl]imidazo[1,5-a]pyrazin-1-yl]-N-(2-pyridyl)benzamide (I-3)

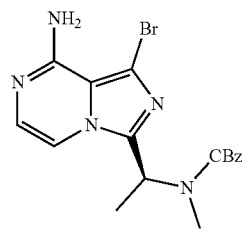

+

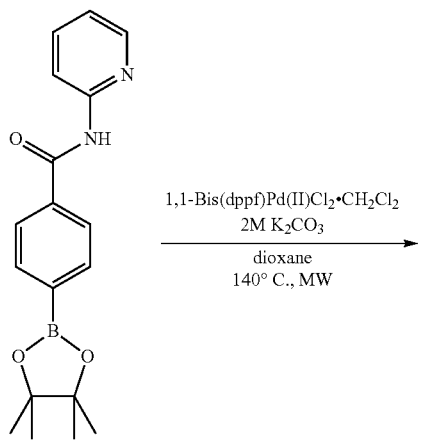

1,1-Bis(dppf)Pd(II)Cl₂·CH₂Cl₂
2M K₂CO₃
dioxane
140° C., MW

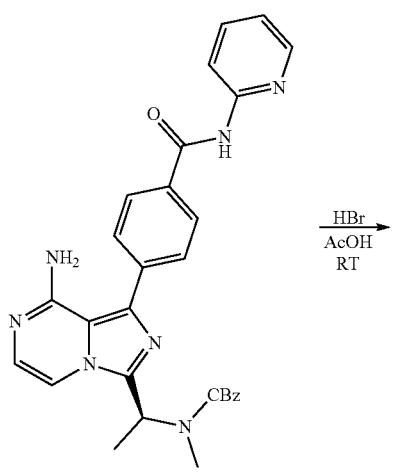

HBr
AcOH
RT

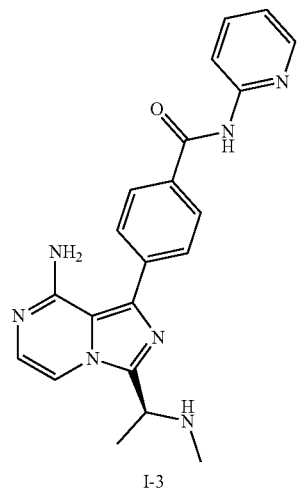

I-3

Preparation of benzyl N-[(1S)-1-[8-amino-1-[4-(2-pyridylcarbamoyl)phenyl]imidazo[1,5-a]pyrazin-3-yl]ethyl]-N-methyl-carbamate. Intermediate 1-2 (300 mg, 0.74 mmol) was added to N-(2-pyridyl)-4-(4,4,5,5-tetramethyl-1,3,2-dioxaborolan-2-yl)benzamide (313 mg, 0.96 mmol) in 1,4-dioxane (15 mL), 2 M aq. potassium carbonate solution (3 mL) was added and the mixture was purged with N₂ gas for 5 minutes. Bis(dppf)Pd(II)C12 (30.3 mg, 0.04 mmol) was added, the mixture was purged again and the reaction mixture was stirred for 30 minutes at 140° C. in the microwave. The reaction mixture was poured into water (50 mL) and extracted two times with ethyl acetate (100 mL). The combined organic extracts were washed once with sat. brine (100 mL), dried over sodium sulfate and concentrated in vacuo. The residue was purified by flash column chromatography (0 to 8% methanol in dichloromethane) to give benzyl N-[(1S)-1-[8-amino-1-[4-(2-pyridylcarbamoyl)phenyl]imidazo[1,5-a]pyrazin-3-yl]ethyl]-N-methyl-carbamate (205 mg, 53.0%) as a yellow oil. Data: LC-MS (Method A) $R_t$: 4.69 min; m/z 522.2 (M+H)⁺.

Preparation of 4-[8-amino-3-[(1S)-1-(methylamino)ethyl]imidazo[1,5-a]pyrazin-1-yl]-N-(2-pyridyl)benzamide. A mixture of hydrobromic acid in acetic acid (33 wt %; 4 mL, 70.2 mmol) and benzyl N-[(1S)-1-[8-amino-1-[4-(2-pyridylcarbamoyl)phenyl]imidazo[1,5-a]pyrazin-3-yl]ethyl]-N-methyl-carbamate (200 mg, 0.38 mmol) was stirred for four hours at room temperature. The reaction mixture was poured into water (50 mL) and extracted two times with dichloromethane (30 mL). The aqueous phase was made basic (pH-10) with solid sodium carbonate, extracted once with dichloromethane (30 mL) and twice with ethyl acetate (50 mL). The combined organic extracts were washed once with sat. brine (100 mL), dried over sodium sulfate and concentrated to give 4-[8-amino-3-[(1S)-1-(methylamino)ethyl]imidazo[1,5-a]pyrazin-1-yl]-N-(2-pyridyl)benzamide (115 mg, 77.4%) as an off white solid. Data: LC-MS (Method A) $R_t$: 1.09 min; m/z 388.2 (M+H)⁺.

Example 6—Preparation of 2-methoxy-N-(2-pyridyl)-4-(4,4,5,5-tetramethyl-1,3,2-dioxaborolan-2-yl)benzamide (I-4)

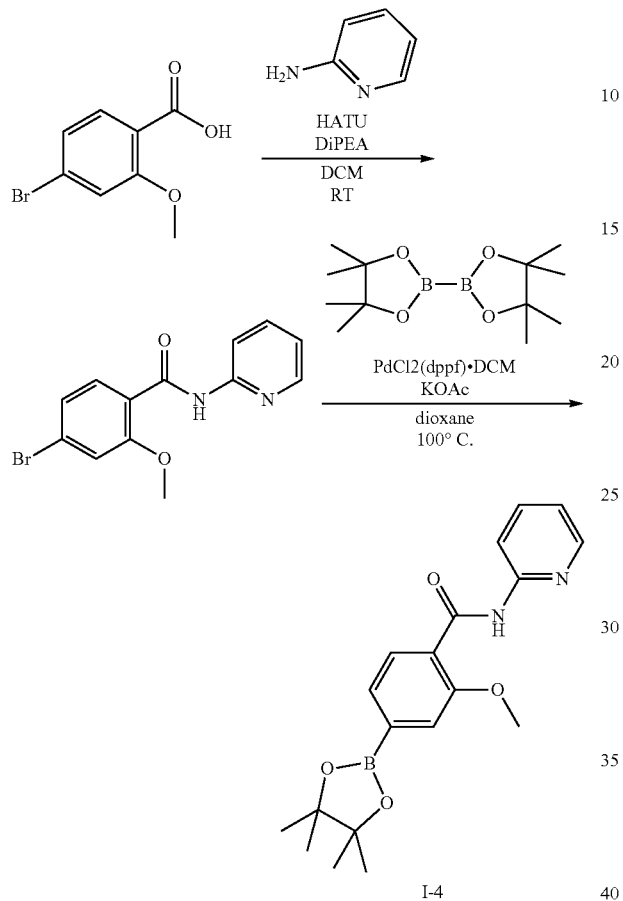

Preparation of 4-bromo-2-methoxy-N-(2-pyridyl)benzamide. To a solution of 4-bromo-2-methoxy-benzoic acid (15.3 g, 66.2 mmol) in dichloromethane (250 mL) was added pyridin-2-amine (6.9 g, 72.8 mmol) and DIPEA (34.6 mL, 198.7 mmol). HATU (32.7 g, 86.1 mmol) was added and the mixture was stirred at room temperature overnight. Water (200 mL) was added and the reaction mixture was stirred for 1 hour. The organic layer was concentrated under reduced pressure. DCM (50 mL) was added and the solution was allowed to crystallize over the weekend. The solids were filtered off, washed twice with diethyl ether (10 mL) and dried under reduced pressure to give 4-bromo-2-methoxy-N-(2-pyridyl)benzamide (14.4 g, 66.8%) as light brown crystals. Data: LC-MS (Method A) $R_t$: 6.05 min; m/z 307.0+309.0 (1:1) (M+H)$^+$.

Preparation of 2-methoxy-N-(2-pyridyl)-4-(4,4,5,5-tetramethyl-1,3,2-dioxaborolan-2-yl)benzamide. To a solution of 4-bromo-2-methoxy-N-(2-pyridyl)benzamide (14.4 g, 46.9 mmol) in 1,4-dioxane (175 mL) was added bis(pinacolata)diboron (14.3 g, 56.3 mmol) and potassium acetate (9.2 g, 93.8 mmol). PdCl$_2$(dppf).DCM (1.9 g, 2.3 mmol) was added and the mixture was stirred at 100° C. for 5 hours. The reaction mixture was diluted with water (150 mL) and extracted twice with ethyl acetate (150 mL). The combined organic layers were dried over sodium sulfate, filtered and concentrated under reduced pressure. The residue was purified by flash column chromatography (0 to 50% ethyl acetate in heptane). The fractions containing product were concentrated under reduced pressure. The residue was suspended in heptane (150 mL) and stirred for 30 minutes. The solids were filtered off and washed twice with heptane (15 mL), to give 2-methoxy-N-(2-pyridyl)-4-(4,4,5,5-tetramethyl-1,3,2-dioxaborolan-2-yl)benzamide (10.4 g, 62.6%) as a white solid. Data: LC-MS (Method A) $R_t$: 6.86 min; m/z 355.2 (M+H)$^+$. $^1$H NMR (400 MHz, DMSO-d$_6$, 300 K): δ=10.51 (1H, s), 8.36 (1H, m), 8.26 (1H, d, J=8.4 Hz), 7.89 (1H, d, J=7.6 Hz), 7.85 (1H, m), 7.41 (1H, dd, J1=7.6 Hz, J2=0.9 Hz), 7.38 (1H, s), 7.17 (1H, m), 4.01 (3H, s), 1.33 (12H, s).

Example 7—Preparation of 4-[8-amino-3-[(1S)-1-(methylamino)ethyl]imidazo[1,5-a]pyrazin-1-yl]-2-methoxy-N-(2-pyridyl)benzamide (I-5)

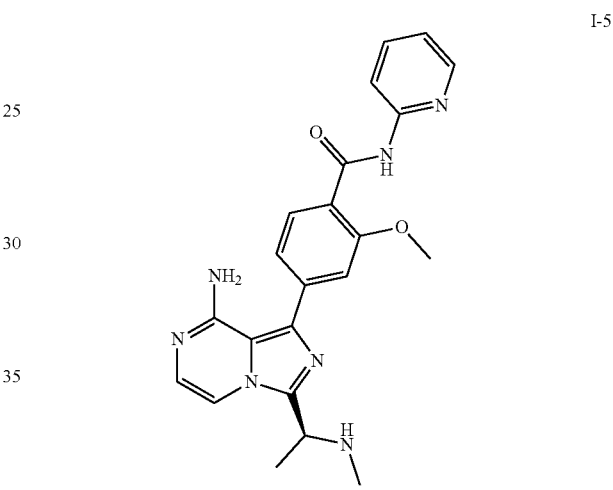

Preparation of 4-[8-amino-3-[(1S)-1-(methylamino)ethyl]imidazo[1,5-a]pyrazin-1-yl]-2-methoxy-N-(2-pyridyl)benzamide. This compound was prepared in an analogous manner as described for Intermediate I-3 using Intermediate I-2 and I-4 to afford the title compound (320 mg, 100%, over two steps) as a light yellow solid. Data: LC-MS (Method A) $R_t$: 2.38 min; m/z 418.2 (M+H)$^+$.

Example 8—Preparation of N-(5-methyl-2-pyridyl)-4-(4,4,5,5-tetramethyl-1,3,2-dioxaborolan-2-yl)benzamide (I-6)

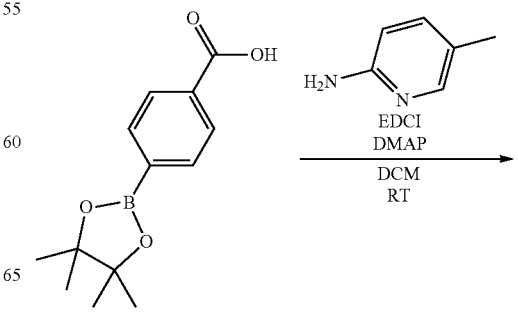

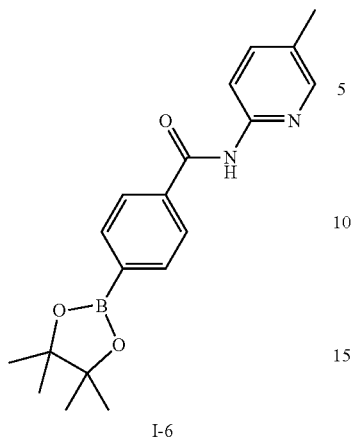

I-6

Preparation of N-(5-methyl-2-pyridyl)-4-(4,4,5,5-tetramethyl-1,3,2-dioxaborolan-2-yl)benzamide. 4-(4,4,5,5-Tetramethyl-1,3,2-dioxaborolan-2-yl)benzoic acid (3.0 g, 12.09 mmol), 5-methylpyridin-2-amine (1.43 g, 13.3 mmol), EDCI (2.55 g, 13.3 mmol) and DMAP (177.3 mg, 1.45 mmol) were dissolved in DCM (50 mL). The reaction mixture was stirred overnight at 21° C. 50 mL 3% aqueous citric acid solution was added to the reaction mixture and the reaction mixture was stirred for 15 minutes. The organic layer was washed sequentially with 50 mL 1% aqueous citric acid and brine (50 mL), poured over a PE-filter and concentrated in vacuo, yielding the title compound as an off-white solid (3.52 g, 86.0%). Data: LC-MS $R_t$: 6.397 min; m/z 339.3 (M+H)+; $^1$H NMR (400 MHz, CDCl$_3$, 300 K): δ=8.86 (1H, s), 8.32 (1H, d, J=8.5 Hz), 8.12 (1H, m), 7.93 (4H, s), 7.60 (1H, dd, J1=2.3 Hz, J2=8.5 Hz), 2.33 (3H, s), 1.37 (12H, s).

Example 9—Preparation of 4-[8-amino-3-[(1S)-1-(methylamino)ethyl]imidazo[1,5-a]pyrazin-1-yl]-N-(5-methyl-2-pyridyl)benzamide (I-7)

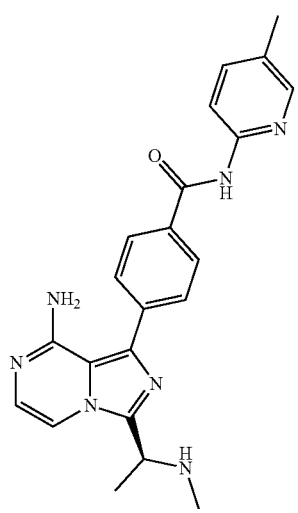

I-7

Preparation of 4-[8-amino-3-[(1S)-1-(methylamino)ethyl]imidazo[1,5-a]pyrazin-1-yl]-N-(5-methyl-2-pyridyl)benzamide. This compound was prepared in an analogous manner as described for Intermediate I-3 using Intermediate I-2 and I-6 to afford the title compound (275 mg, 92%, over two steps) as a light yellow solid. Data: LC-MS (Method A) $R_t$: 1.60 min; m/z 402.1 (M+H)+.

Example 10—Preparation of 2-methoxy-N-(5-methyl-2-pyridyl)-4-(4,4,5,5-tetramethyl-1,3,2-dioxaborolan-2-yl)benzamide (I-8)

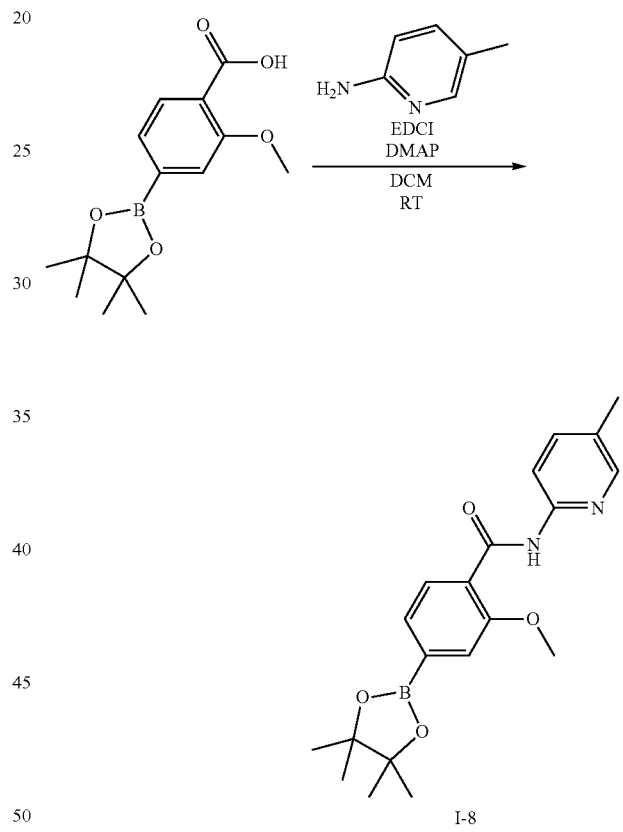

I-8

Preparation of 2-methoxy-N-(5-methyl-2-pyridyl)-4-(4,4,5,5-tetramethyl-1,3,2-dioxaborolan-2-yl)benzamide. This compound was prepared in an analogous manner as described for Intermediate I-6 using 2-methoxy-4-(4,4,5,5-tetramethyl-1,3,2-dioxaborolan-2-yl)benzoic acid to afford the title compound (4.21 g, 75.2%) as an off-white solid. Data: LC-MS $R_t$: 7.178 min; m/z 369.3 (M+H)+; $^1$H NMR (400 MHz, CDCl$_3$, 300 K): δ=10.34 (1H, s), 8.33 (1H, d, J=8.6 Hz), 8.25 (1H, d, J=7.7 Hz), 8.14 (1H, m), 7.55 (2H, d, J=7.8 Hz), 7.44 (1H, s), 4.12 (3H, s), 2.31 (3H, s), 1.37 (12H, s).

Example 11—Preparation of 4-[8-amino-3-[(1S)-1-(methylamino)ethyl]imidazo[1,5-a]pyrazin-1-yl]-2-methoxy-N-(5-methyl-2-pyridyl)benzamide (I-9)

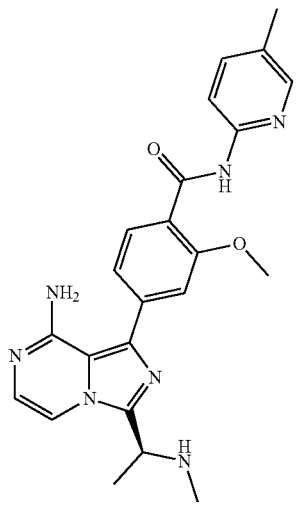

I-9

Preparation of 4-[8-amino-3-[(1S)-1-(methylamino)ethyl]imidazo[1,5-a]pyrazin-1-yl]-2-methoxy-N-(5-methyl-2-pyridyl)benzamide. This compound was prepared in an analogous manner as described for Intermediate I-3 using Intermediate I-2 and I-8 to afford the title compound (209 mg, 66%, over two steps) as a light yellow solid. Data: LC-MS (Method A) $R_t$: 2.86 min; m/z 432.2 (M+H)$^+$.

Example 12—Preparation of benzyl-(2S)-2-(8-amino-1-bromo-imidazo[1,5-a]pyrazin-3-yl)pyrrolidine-1-carboxylate sulfate salt (I-10)

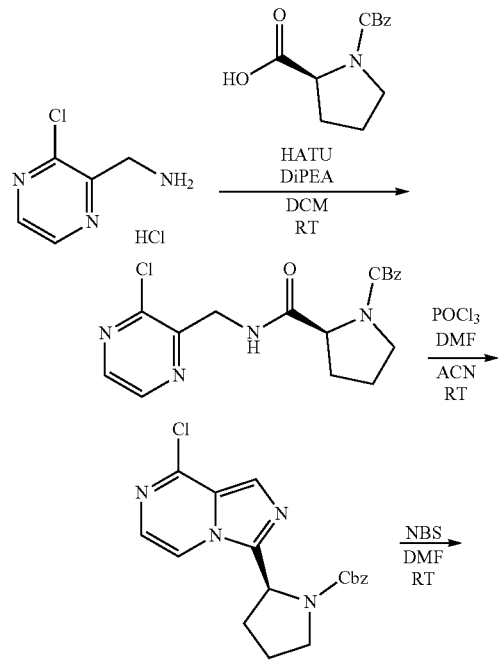

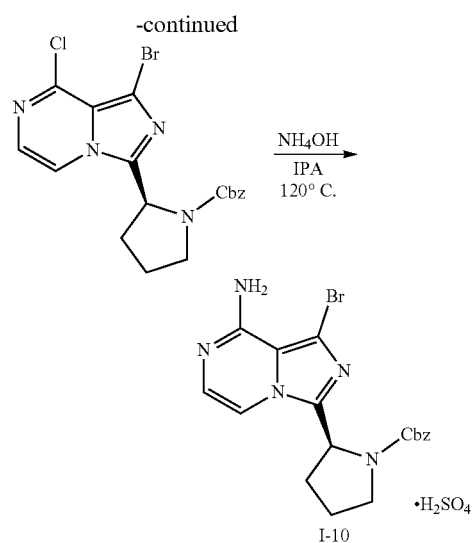

I-10

Preparation of benzyl (2S)-2-(8-amino-1-bromo-imidazo[1,5-a]pyrazin-3-yl)pyrrolidine-1-carboxylate sulfate. This compound was prepared in an analogous manner as described in International Patent Application Publication No. WO 2013/010868 A1, the disclosure of which is incorporated herein by reference, to afford the title compound as a beige solid. Data: LC-MS (Method A) $R_t$: 3.736 min; m/z 414.1+416.1 (1:1) (M+H)$^+$.

Example 13—Preparation of 4-[8-amino-3-[(2S)-pyrrolidin-2-yl]imidazo[1,5-a]pyrazin-1-yl]-2-methoxy-N-[4-(trifluoromethyl)-2-pyridyl]benzamide (I-11)

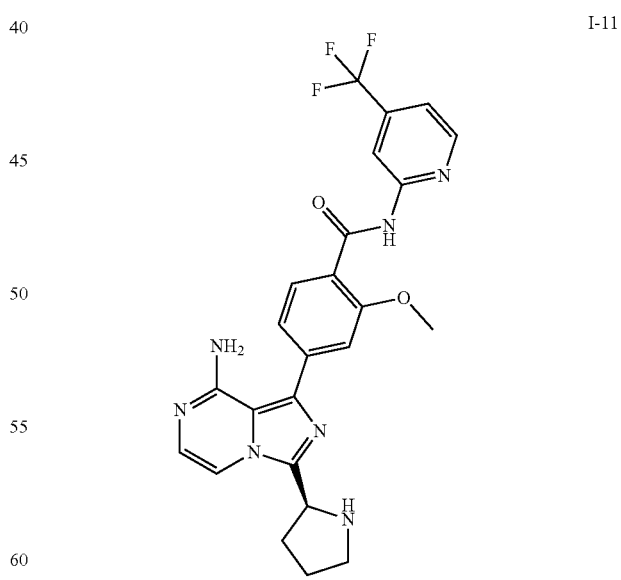

I-11

Preparation of 4-[8-amino-3-[(2S)-pyrrolidin-2-yl]imidazo[1,5-a]pyrazin-1-yl]-2-methoxy-N-[4-(trifluoromethyl)-2-pyridyl]benzamide. This compound was prepared in an analogous manner as described for Intermediate I-3 using Intermediate I-1 and I-10 to afford the title compound (165 mg, 47%, over two steps) as a light yellow solid. Data: LC-MS (Method A) $R_t$: 3.86 min; m/z 498.3 (M+H)$^+$.

Example 14—Preparation of benzyl N-[(1S)-1-(8-amino-1-bromo-imidazo[1,5-a]pyrazin-3-yl)ethyl]carbamate (I-12)

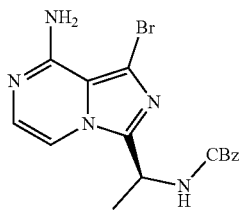

I-12

Preparation of benzyl N-[(1S)-1-(8-amino-1-bromo-imidazo[1,5-a]pyrazin-3-yl)ethyl]carbamate. This compound was prepared in an analogous manner as described for Intermediate I-2 using (2S)-2-(benzyloxycarbonylamino)propanoic acid to afford the title compound (1.8 g, 42%, over four steps) as a white solid. Data: LC-MS (Method A) $R_t$: 3.59 min; m/z 390.0+392.0 (1:1) (M+H)$^+$.

Example 15—Preparation of 4-[8-amino-3-[(1S)-1-aminoethyl]imidazo[1,5-a]pyrazin-1-yl]-2-methoxy-N-[4-(trifluoromethyl)-2-pyridyl]benzamide (I-13)

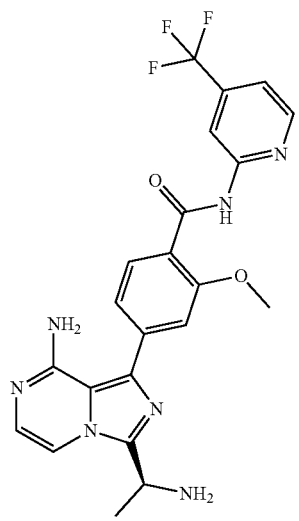

I-13

Preparation of 4-[8-amino-3-[(1S)-1-aminoethyl]imidazo[1,5-a]pyrazin-1l-yl]-2-methoxy-N-[4-(trifluoromethyl)-2-pyridyl]benzamide. This compound was prepared in an analogous manner as described for Intermediate I-3 using Intermediate I-1 and I-12 to afford the title compound (79 mg, 65%, over two steps). Data: LC-MS (Method A) $R_t$: 3.771 min; m/z 472.2 (M+H)$^+$.

Example 16—Preparation of 4-[8-amino-3-[(1S)-1-aminoethyl]imidazo[1,5-a]pyrazin-1-yl]-2-methoxy-N-(2-pyridyl)benzamide (I-14)

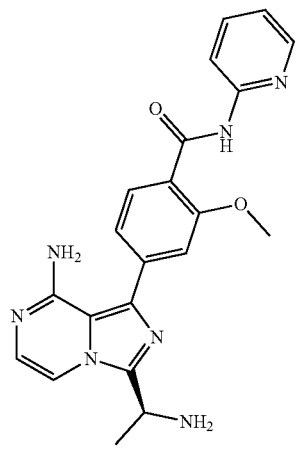

I-14

Preparation of 4-[8-amino-3-[(1S)-1-aminoethyl]imidazo[1,5-a]pyrazin-1-yl]-2-methoxy-N-(2-pyridyl)benzamide. This compound was prepared in an analogous manner as described for Intermediate I-3 using Intermediate I-4 and I-12 to afford the title compound (164 mg, 66%, over two steps) as a yellow solid. Data: LC-MS (Method A) $R_t$: 2.04 min; m/z 404.1 (M+H)$^+$.

Example 17—Preparation of 4-(4,4,5,5-tetramethyl-1,3,2-dioxaborolan-2-yl)-N-[4-(trifluoromethyl)-2-pyridyl]benzamide (I-15)

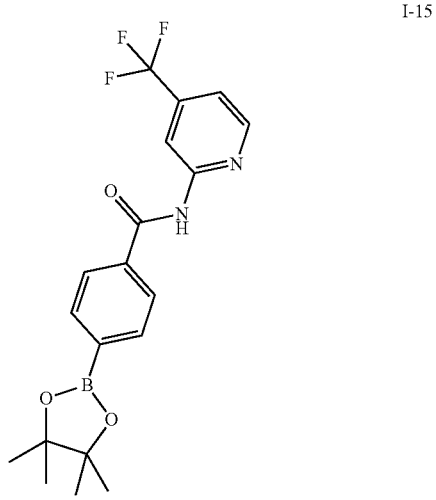 [SMILES: CC1(C)OB(c2ccc(C(=O)Nc3cc(C(F)(F)F)ccn3)cc2)OC1(C)C]

I-15

Preparation of 4-(4,4,5,5-tetramethyl-1,3,2-dioxaborolan-2-yl)-N-[4-(trifluoromethyl)-2-pyridyl]benzamide. This compound was prepared in an analogous manner as described for Intermediate I-6 using 4-(trifluoromethyl)pyridin-2-amine to afford the title compound (694 mg, 43.9%) as a white solid. Data: LC-MS (Method A) $R_t$: 7.74 min; m/z 393.3 (M+H)$^+$.

Example 18—Preparation of 4-[8-amino-3-[(1S)-1-aminoethyl]imidazo[1,5-a]pyrazin-1-yl]-N-[4-(trifluoromethyl)-2-pyridyl]benzamide (I-16)

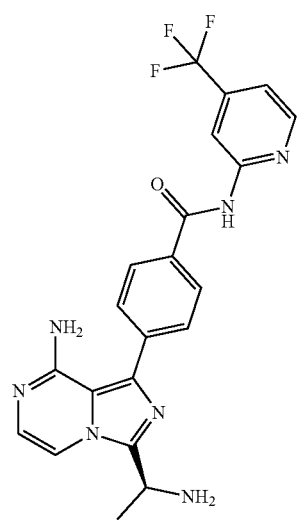

I-16

Preparation of 4-[8-amino-3-[(1S)-1-aminoethyl]imidazo[1,5-a]pyrazin-1-yl]-N-[4-(trifluoromethyl)-2-pyridyl]benzamide. This compound was prepared in an analogous manner as described for Intermediate I-3 using Intermediate I-12 and I-15 to afford the title compound (135 mg, 59.6%, over two steps) as a yellow solid. Data: LC-MS (Method A) $R_t$: 3.40 min; m/z 442.2 (M+H)$^+$.

Example 19—Preparation of 4-[8-amino-3-[(1S)-1-aminoethyl]imidazo[1,5-a]pyrazin-1-yl]-N-(5-methyl-2-pyridyl)benzamide (I-17)

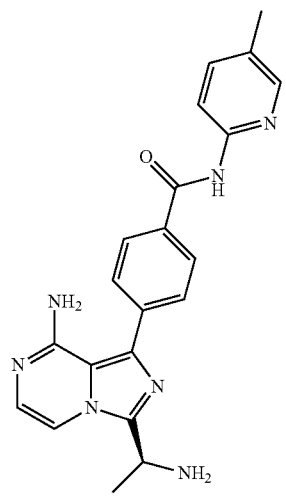

I-17

Preparation of 4-[8-amino-3-[(1S)-1-aminoethyl]imidazo[1,5-a]pyrazin-1-yl]-N-(5-methyl-2-pyridyl)benzamide. This compound was prepared in an analogous manner as described for Intermediate I-3 using Intermediate I-12 and I-6 to afford the title compound (217 mg, 70%, over two steps) as a light yellow solid. Data: LC-MS (Method A) $R_t$: 1.28 min; m/z 388.2 (M+H)$^+$.

Example 20—Preparation of 4-[8-amino-3-[(1S)-1-aminoethyl]imidazo[1,5-a]pyrazin-1-yl]-2-methoxy-N-(5-methyl-2-pyridyl)benzamide (I-18)

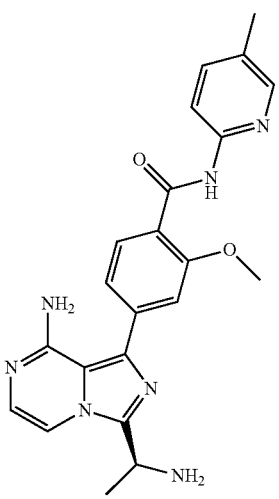

I-18

Preparation of 4-[8-amino-3-[(1S)-1-aminoethyl]imidazo[1,5-a]pyrazin-1-yl]-2-methoxy-N-(5-methyl-2-pyridyl)benzamide. This compound was prepared in an analogous manner as described for Intermediate I-3 using Intermediate I-12 and I-8 to afford the title compound (219 mg, 77%, over two steps) as a yellow solid. Data: LC-MS (Method A) $R_t$: 2.68 min; m/z 418.2 (M+H)$^+$.

Example 21—Preparation of 2-methoxy-4-(4,4,5,5-tetramethyl-1,3,2-dioxaborolan-2-yl)-N-thiazol-2-yl-benzamide (I-19)

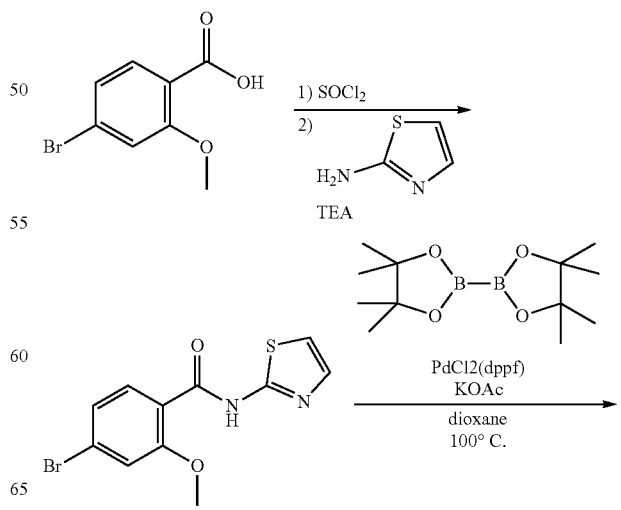

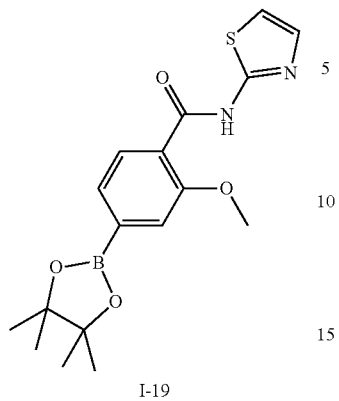

I-19

Preparation of 4-bromo-2-methoxy-benzoyl chloride. 4-Bromo-2-methoxy-benzoic acid (8.38 g, 36.27 mmol) was dissolved in DCM (75 mL). Thionyl chloride (5.29 mL, 72.54 mmol) and a catalytic amount of DMF were added. The reaction mixture was stirred for 3 hours at reflux. The reaction mixture was concentrated in vacuo and dried on the oil pump yielding a yellow solid with a quantitative yield (9.5 g).

Preparation of 4-bromo-2-methoxy-N-thiazol-2-yl-benzamide. 4-Bromo-2-methoxy-benzoyl chloride (4.00 g, 16.03 mmol) was added to a solution of thiazol-2-amine (3.21 g, 32.07 mmol) and triethylamine (3.34 mL, 24.1 mmol) in acetonitrile (100 mL). The mixture was stirred overnight at 21° C. The reaction mixture was diluted with water (100 mL) and was washed twice with EtOAc (2×100 mL). The organic layer was washed with brine (150 mL), dire over sodium sulfate and concentrated in vacuo. The crude product was purified using flash chromatography eluting with 0-100% EtOAc in heptane, yielding the title compound as a white solid (1.01 g, 20.1%). Data: LC-MS $R_t$: 6.065 min; m/z 313.0+315.0 (M, M+2)$^+$.

Preparation of 2-methoxy-4-(4,4,5,5-tetramethyl-1,3,2-dioxaborolan-2-yl)-N-thiazol-2-yl-benzamide. 4-Bromo-2-methoxy-N-thiazol-2-yl-benzamide (1.01 g, 3.23 mmol) was dissolved in dry 1,4-dioxane (32 mL). Bis(pinacolato)diboron (983 mg, 3.87 mmol) and potassium acetate (633 mg, 6.45 mmol) were added. The mixture was purged with nitrogen gas for 10 min. PdCl$_2$(dppf)$_2$ (132 mg, 0.16 mmol) was added and the mixture was purged again with nitrogen gas for 5 minutes. The reaction mixture was stirred overnight at 100° C. under a nitrogen gas atmosphere. The reaction mixture was diluted with water (40 mL) and extracted with EtOAc (50 mL). The organic layer was washed with brine (40 mL), dried over sodium sulfate and concentrated in vacuo resulting a brown/black oil (1.76 g crude >100%), which was used crude in the next step. LC-MS $R_t$: 6.928 min; m/z 361.2 (M+H)$^+$.

Example 22—Preparation of 4-[8-amino-3-[(2S)-pyrrolidin-2-yl]imidazo[1,5-a]pyrazin-1-yl]-2-methoxy-N-thiazol-2-yl-benzamide (I-20)

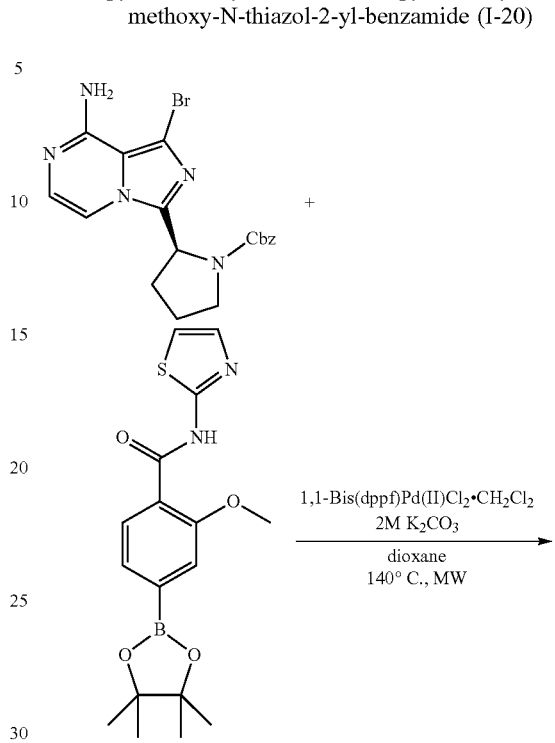

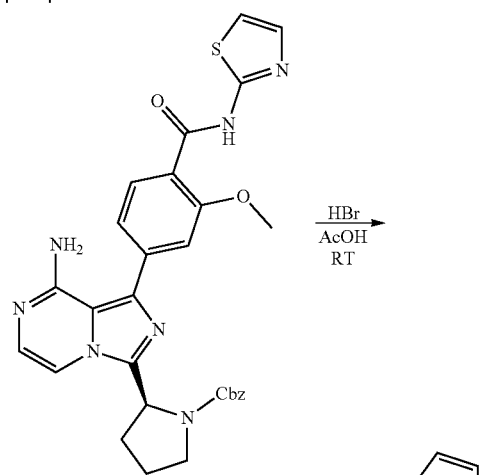

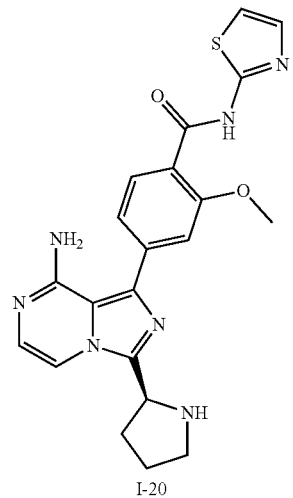

I-20

Preparation of 4-[8-amino-3-[(2S)-pyrrolidin-2-yl]imidazo[1,5-a]pyrazin-1-yl]-2-methoxy-N-thiazol-2-yl-benzamide. This compound was prepared in an analogous manner as described for Intermediate I-3 using Intermediate I-10 and I-19 to afford the title compound (89 mg, 42%, over two steps) as a yellow solid. Data: LC-MS (Method A) R$_t$: 2.851 min; m/z 436.3 (M+H)$^+$.

Example 23—Preparation of 4-[8-amino-3-[(2S)-pyrrolidin-2-yl]imidazo[1,5-a]pyrazin-1-yl]-N-(5-methyl-2-pyridyl)benzamide (I-21)

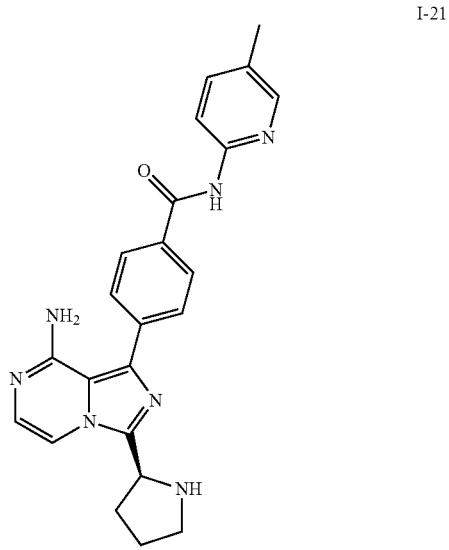 [SMILES: Cc1ccc(NC(=O)c2ccc(-c3nc([C@@H]4CCCN4)n4ccnc(N)c34)cc2)nc1]

I-21

Preparation of 4-[8-amino-3-[(2S)-pyrrolidin-2-yl]imidazo[1,5-a]pyrazin-1-yl]-N-(5-methyl-2-pyridyl)benzamide. This compound was prepared in an analogous manner as described for Intermediate I-3 using Intermediate I-10 and I-6 to afford the title compound (176 mg, 87%, over two steps) as a yellow solid. Data: LC-MS (Method A) R$_t$: 1.728 min; m/z 414.2 (M+H)$^+$.

Example 24—Preparation of 4-[8-amino-3-[(2S)-pyrrolidin-2-yl]imidazo[1,5-a]pyrazin-1-yl]-2-methoxy-N-(5-methyl-2-pyridyl)benzamide (I-22)

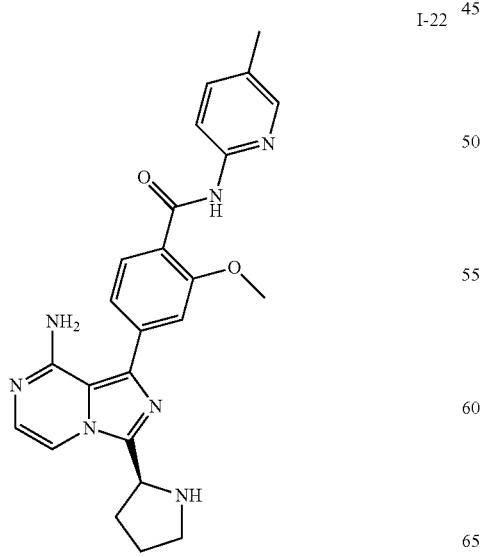

I-22

Preparation of 4-[8-amino-3-[(2S)-pyrrolidin-2-yl]imidazo[1,5-a]pyrazin-1-yl]-2-methoxy-N-(5-methyl-2-pyridyl)benzamide. This compound was prepared in an analogous manner as described for Intermediate I-3 using Intermediate I-10 and I-8 to afford the title compound (187 mg, 87%, over two steps) as a yellow solid. Data: LC-MS (Method A) R$_t$: 2.975 min; m/z 444.2 (M+H)$^+$.

Example 25—Preparation of 4-[8-amino-3-[(1S)-1-[but-2-ynoyl(methyl)amino]ethyl]imidazo[1,5-a]pyrazin-1-yl]-N-(2-pyridyl)benzamide (E-1)

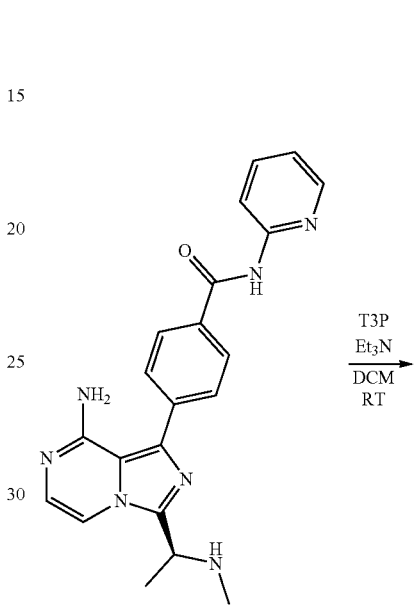

T3P
Et$_3$N
DCM
RT

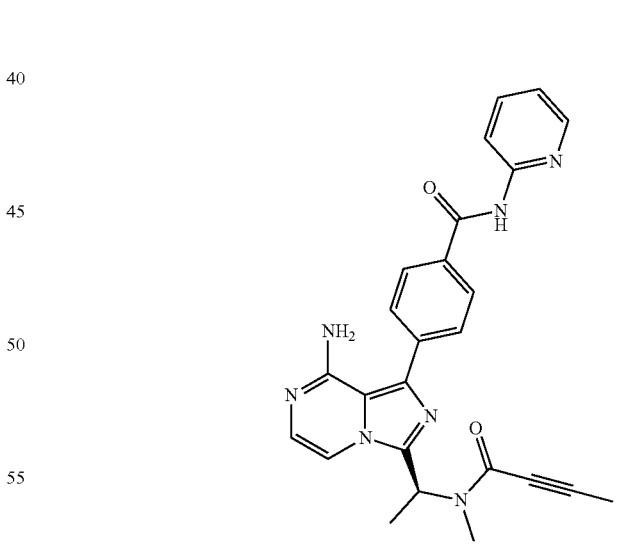

Preparation of 4-[8-amino-3-[(1S)-1-[but-2-ynoyl(methyl)amino]ethyl]imidazo[1,5-a]pyrazin-1-yl]-N-(2-pyridyl)benzamide. Propylphosphonic anhydride solution (50% in DMF) (0.08 mL, 0.15 mmol) was added to a solution of triethylamine (0.05 mL, 0.39 mmol), but-2-ynoic acid (13.67 mg, 0.16 mmol) and Intermediate I-3 (60 mg, 0.15 mmol) in dichloromethane (10 mL) and the mixture was stirred for two hours at room temperature. The reaction mixture was directly loaded on a SiO$_2$-column and purified by flash column chromatography (0 to 8% methanol in dichloromethane), the purest fractions were combined and concentrated. The residue was lyophilized as a suspension from acetonitrile/water (1:1) to give the title compound (56.9 mg, 81.0%) as a light yellow solid. Data: LC-MS $R_t$: 3.77 min; m/z 454.2 (M+H)+; HPLC (Method C) $R_t$: 4.95 min, 100% purity; $^1$H NMR (400 MHz, DMSO-$d_6$, 300 K): δ=10.88 (1H, s), 8.43 (1H, ddd, J1=4.8 Hz, J2=1.9 Hz, J3=0.9 Hz), 8.25 (1H, dt, J1=8.3 Hz, J2=0.9 Hz), 8.19 (2H, dd, J1=8.5 Hz, J2=1.5 Hz), 7.88 (1H, m), 7.79 (2H, dd, J1=8.5 Hz, J2=2.2 Hz), 7.40 (0.3H, d J=5.1 Hz), 7.32 (0.7H, d J=5.1 Hz), 7.25 (0.3H, d, J=4.9), 7.20 (1.7H, m), 6.28 (2H, br. s), 6.16 (1H, m), 2.88 (2.1H, s), 2.60 (0.9H, s), 2.16 (0.9H, s), 2.05 (2.1H, s), 1.74 (0.9H, d, J=6.9 Hz), 1.65 (2.1H, d, J=6.9 Hz).

Example 26—Preparation of 4-[8-amino-3-[(1S)-1-[but-2-ynoyl(methyl)amino]ethyl]imidazo[1,5-a]pyrazin-1-yl]-2-methoxy-N-(2-pyridyl)benzamide (E-2)

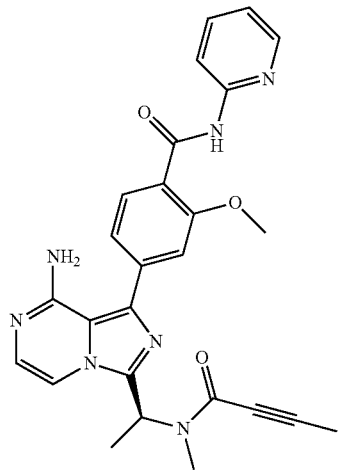 [SMILES: CC#CC(=O)N(C)[C@@H](C)c1nc(-c2ccc(C(=O)Nc3ccccn3)c(OC)c2)c2c(N)nccn12]

Preparation of 4-[8-amino-3-[(1S)-1-[but-2-ynoyl(methyl)amino]ethyl]imidazo[1,5-a]pyrazin-1-yl]-2-methoxy-N-(2-pyridyl)benzamide. This compound was prepared in an analogous manner as described for Example E-1 using Intermediate I-5 and but-2-ynoic acid to afford the title compound (67 mg, 57%) as a light yellow solid. Data: LC-MS (Method A) $R_t$: 4.19 min; m/z 484.1 (M+H)+; HPLC (Method C) $R_t$: 5.93 min, 99.0% purity; $^1$H NMR (400 MHz, DMSO-$d_6$, 300 K): δ=10.50 (1H, s), 8.38 (1H, m), 8.30 (1H, d, J=8.2 Hz), 8.05 (1H, d, J=8.0 Hz), 7.87 (1H, m), 7.43 (2H, m), 7.39 (0.3H, d, J=5.0 Hz), 7.30 (0.7H, d, J=5.1 Hz), 7.24 (0.3H, d, J=4.9 Hz), 7.18 (1.7H, m), 6.35 (2H, m), 6.14 (1H, m), 4.08 (3H, s), 2.87 (2H, s), 2.60 (1H, s), 2.14 (1H, s), 2.03 (2H, s), 1.73 (1H, d, 6.8 Hz), 1.64 (2H, d, J=6.8 Hz).

Example 27—Preparation of 4-[8-amino-3-[(1S)-1-[but-2-ynoyl(methyl)amino]ethyl]imidazo[1,5-a]pyrazin-1-yl]-N-(5-methyl-2-pyridyl)benzamide (E-3)

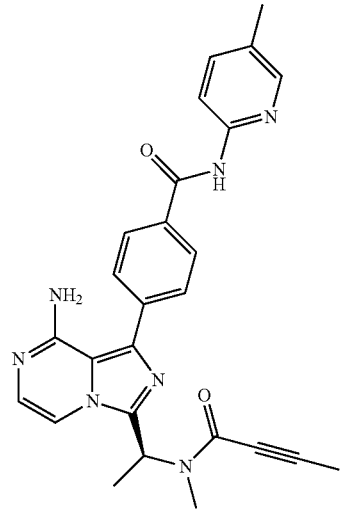 [SMILES: CC#CC(=O)N(C)[C@@H](C)c1nc(-c2ccc(C(=O)Nc3ccc(C)cn3)cc2)c2c(N)nccn12]

Preparation of 4-[8-amino-3-[(1S)-1-[but-2-ynoyl(methyl)amino]ethyl]imidazo[1,5-a]pyrazin-1-yl]-N-(5-methyl-2-pyridyl)benzamide. This compound was prepared in an analogous manner as described for Example E-1 using Intermediate I-7 and but-2-ynoic acid to afford the title compound (67 mg, 57%) as a light yellow solid. Data: LC-MS (Method A) $R_t$: 3.89 min; m/z 468.3 (M+H)$^+$; HPLC (Method C) $R_t$: 5.25 min, 99.9% purity; $^1$H NMR (400 MHz, DMSO-$d_6$, 300 K): δ=10.79 (1H, s), 8.26 (1H, m), 8.19 (2H, dd, J1=8.6 Hz, J2=1.6 Hz), 8.14 (1H, d, J=8.5 Hz), 7.78 (2H, dd, J1=8.6 Hz, J2=2.3 Hz), 7.70 (1H, dd, J1=8.6 Hz, J2=2.0 Hz), 7.40 (0.3H, d, J=5.0 Hz), 7.31 (0.7H, d, J=5.0 Hz), 7.25 (0.3H, d, J=4.9 Hz), 7.19 (0.7H, d, J=4.9 Hz), 6.28 (2H, m), 6.16 (1H, m), 2.88 (2H, s), 2.61 (1H, s), 2.31 (3H, s), 2.16 (1H, s), 2.05 (2H, s), 1.74 (1H, d, J=6.8 Hz), 1.65 (2H, d, J=6.8 Hz).

Example 28—Preparation of 4-[8-amino-3-[(1S)-1-[but-2-ynoyl(methyl)amino]ethyl]imidazo[1,5-a]pyrazin-1-yl]-2-methoxy-N-(5-methyl-2-pyridyl)benzamide (E-4)

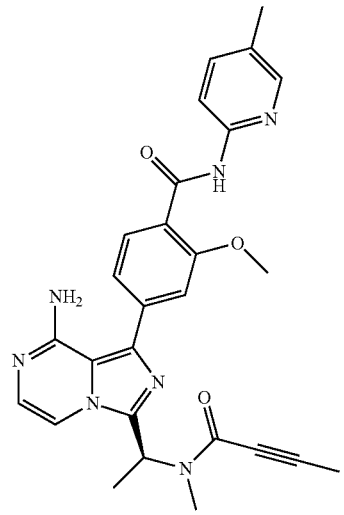 [SMILES: CC#CC(=O)N(C)[C@@H](C)c1nc(-c2ccc(C(=O)Nc3ccc(C)cn3)c(OC)c2)c2c(N)nccn12]

Preparation of 4-[8-amino-3-[(1S)-1-[but-2-ynoyl(methyl)amino]ethyl]imidazo[1,5-a]pyrazin-1-yl]-2-methoxy-N-(5-methyl-2-pyridyl)benzamide. This compound was prepared in an analogous manner as described for Example E-1 using Intermediate I-9 and but-2-ynoic acid to afford the title compound (68 mg, 59%) as a white solid. Data: LC-MS (Method A) R$_t$: 4.39 min; m/z 498.2 (M+H)+; HPLC (Method C) R$_t$: 5.90 min, 100% purity; $^1$H NMR (400 MHz, DMSO-d$_6$, 300 K): δ=10.42 (1H, s), 8.20 (2H, m), 8.05 (1H, d, J=8.0 Hz), 7.69 (1H, dd, J1=8.6 Hz, J2=2.3 Hz), 7.17-7.45 (4H, m), 6.35 (2H, m). 6.14 (1H, m), 4.07 (3H, s), 2.86 (2H, s), 2.60 (1H, s), 2.29 (3H, s), 2.04 (2H, s), 1.97 (1H, s), 1.73 (1H, d, J=6.8 Hz), 1.64 (2H, d, J=6.8 Hz).

Example 29—Preparation of 4-[8-amino-3-[(2S)-1-but-2-ynoylpyrrolidin-2-yl]imidazo[1,5-a]pyrazin-1-yl]-2-methoxy-N-[4-(trifluoromethyl)-2-pyridyl]benzamide (E-5)

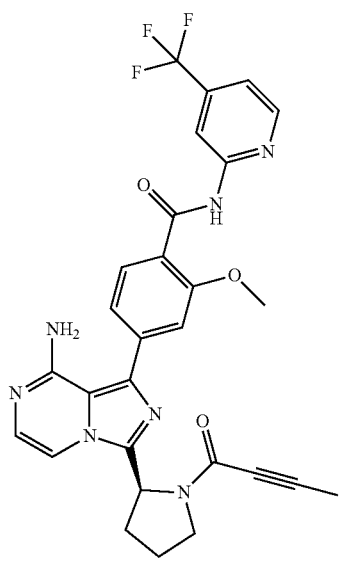 [SMILES: CC#CC(=O)N1CCC[C@H]1c1nc(-c2ccc(C(=O)Nc3cc(C(F)(F)F)ccn3)c(OC)c2)c2c(N)nccn12]

Preparation of 4-[8-amino-3-[(2S)-1-but-2-ynoylpyrrolidin-2-yl]imidazo[1,5-a]pyrazin-1-yl]-2-methoxy-N-[4-(trifluoromethyl)-2-pyridyl]benzamide. This compound was prepared in an analogous manner as described for Example E-1 using Intermediate I-11 and but-2-ynoic acid to afford the title compound (54 mg, 89%) as a light yellow solid. Data: LC-MS (Method A) R$_t$: 5.05 min; m/z 564.4 (M+H)+; HPLC (Method C) R$_t$: 6.82 min, 99.1% purity; $^1$H NMR (400 MHz, DMSO-d$_6$, 300 K): δ=10.86 (1H, s), 8.66 (1H, d, J=5.1 Hz), 8.62 (1H, s), 8.01 (1H, dd, J1=8.1 Hz, J2=1.9 Hz), 7.82 (0.4H, d, J=5.1 Hz), 7.80 (0.6H, d, J=5.1 Hz), 7.56 (1H, d, J=5.1 Hz), 7.40 (2H, m), 7.18 (0.4H, d, J=4.9 Hz), 7.14 (0.6H, d, J=4.9 Hz), 6.26 (2H, m), 5.74 (0.4H, dd, J1=7.6 Hz, J2=4.1 Hz), 5.48 (0.6H, dd, J1=7.6 Hz, J2=4.1 Hz), 4.06 (3H, s), 3.83 (1.3H, m), 3.61 (0.7H, m), 2.48-1.65 (7H, m).

Example 30—Preparation of 4-[8-amino-3-[(1S)-1-[[(E)-4-methoxybut-2-enoyl]-methyl-amino]ethyl]imidazo[1,5-a]pyrazin-1-yl]-N-(5-methyl-2-pyridyl)benzamide (E-6)

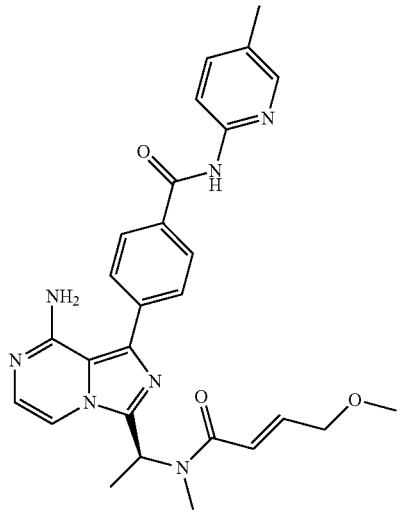 [SMILES: COC/C=C/C(=O)N(C)[C@@H](C)c1nc(-c2ccc(C(=O)Nc3ccc(C)cn3)cc2)c2c(N)nccn12]

Preparation of 4-[8-amino-3-[(1S)-1-[[(E)-4-methoxybut-2-enoyl]-methyl-amino]ethyl]imidazo[1,5-a]pyrazin-1-yl]-N-(5-methyl-2-pyridyl)benzamide. This compound was prepared in an analogous manner as described for Example E-1 using Intermediate I-7 and (E)-4-methoxybut-2-enoic acid. Yield 26.8 mg (42%). Data: LC-MS (Method A) R$_t$: 3.85 min; m/z 500.2 (M+H)+; HPLC (Method C) R$_t$: 5.35 min, 97.3% purity; $^1$H NMR (400 MHz, DMSO-d$_6$, 300 K): δ=10.79 (1H, s), 8.26 (1H, d, J=2.4 Hz), 8.19 (2H, d, J=8.5 Hz), 8.14 (1H, d, J=8.7 Hz), 7.79 (2H, d, J=8.6 Hz), 7.70 (1H, dd, J1=8.7 Hz, J2=2.3 Hz), 7.38 (1H, d, J=5.0 Hz), 7.16 (1H, d, J=4.9 Hz), 6.85 (1H, dt, J1=15.0 Hz, J2=4.2 Hz), 6.55 (1H, d, J=15.2 Hz), 6.33 (1H, q, J1, J2=7.1 Hz), 6.24 (2H, s), 4.10 (1H, dd, J1=2.1 Hz, J2=2.7 Hz), 3.31 (3H, s), 2.79 (3H, s), 2.31 (3H, s) 1.64 (3H, d, J=6.8 Hz).

Example 31—Preparation of 4-[8-amino-3-[(1S)-1-[but-2-ynoyl(methyl)amino]ethyl]imidazo[1,5-a]pyrazin-1-yl]-2-methoxy-N-[4-(trifluoromethyl)-2-pyridyl]benzamide (E-7)

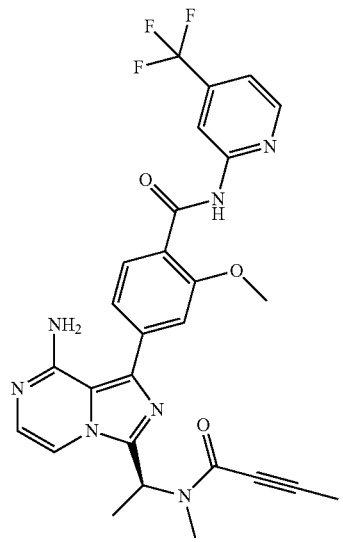 [SMILES: CC#CC(=O)N(C)[C@@H](C)c1nc(-c2ccc(C(=O)Nc3cc(C(F)(F)F)ccn3)c(OC)c2)c2c(N)nccn12]

Preparation of 4-[8-amino-3-[(1S)-1-[but-2-ynoyl(methyl)amino]ethyl]imidazo[1,5-a]pyrazin-1-yl]-2-methoxy-N-[4-(trifluoromethyl)-2-pyridyl]benzamide. This compound was prepared in an analogous manner as described for Example E-1 using Intermediate I-1 and but-2-ynoic acid. Yield 35.5 mg (62%). Data: LC-MS (Method A) R$_t$: 5.20 min; m/z 552.1 (M+H)$^+$; HPLC (Method C) R$_t$: 7.11 min, 99.4% purity; $^1$H NMR (400 MHz, DMSO-d$_6$, 300 K): δ=10.87 (1H, s), 8.66 (1H, d, J=5.2 Hz), 8.61 (1H, s), 8.02 (1H, d, J=8.0 Hz), 7.57 (1H, d, J=5.1 Hz), 7.42 (2H, m), 7.40 (0.3H, s), 7.28 (0.7H, s), 7.24 (0.3H, s), 7.19 (0.7H, s), 6.35 (2H, br. s), 6.15 (1H, m), 4.06 (3H, s), 2.87 (2H, s), 2.61 (1H, s), 2.15 (1H, s), 2.04 (2H, s), 1.73 (1H, d, J=6.8 Hz), 1.64 (2H, d, J=6.8 Hz).

Example 32—Preparation of 4-[8-amino-3-[(1S)-1-(but-2-ynoylamino)ethyl]imidazo[1,5-a]pyrazin-1-yl]-2-methoxy-N-[4-(trifluoromethyl)-2-pyridyl]benzamide (E-8)

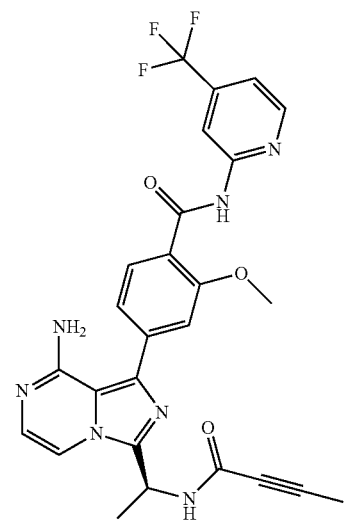 [SMILES: CC#CC(=O)N[C@@H](C)c1nc(-c2ccc(C(=O)Nc3cc(C(F)(F)F)ccn3)c(OC)c2)c2c(N)nccn12]

Preparation of 4-[8-amino-3-[(1S)-1-(but-2-ynoylamino)ethyl]imidazo[1,5-a]pyrazin-1-yl]-2-methoxy-N-[4-(trifluoromethyl)-2-pyridyl]benzamide. This compound was prepared in an analogous manner as described for Example E-1 using Intermediate I-13 and but-2-ynoic acid with a yield of 31.1 mg (54%). Data: LC-MS (Method A) R$_t$: 4.78 min; m/z 538.2 (M+H)$^+$; HPLC (Method C) R$_t$: 6.40 min, 99.8% purity; $^1$H NMR (400 MHz, DMSO-d$_6$, 300 K): δ=10.87 (1H, s), 9.22 (1H, d, J=8.0 Hz), 8.67 (1H, d, J=5.2 Hz), 8.61 (1H, s), 8.02 (1H, d, J=8.0 Hz), 7.56 (2H, m), 7.42 (2H, m), 7.16 (1H, d, J=4.9 Hz), 6.28 (2H, br. s), 5.48 (1H, m), 4.06 (3H, s), 1.98 (3H, s), 1.59 (3H, d, J=6.9 Hz).

Example 33—Preparation of 4-[8-amino-3-[(1S)-1-(but-2-ynoylamino)ethyl]imidazo[1,5-a]pyrazin-1-yl]-2-methoxy-N-(2-pyridyl)benzamide (E-9)

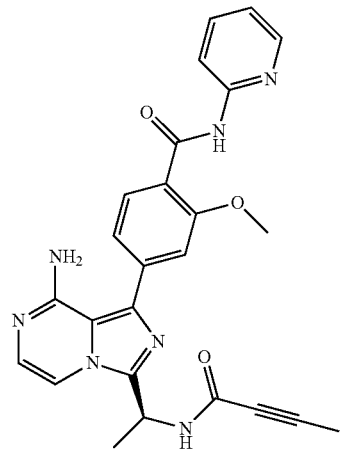 [SMILES: CC#CC(=O)N[C@@H](C)c1nc(-c2ccc(C(=O)Nc3ccccn3)c(OC)c2)c2c(N)nccn12]

Preparation of 4-[8-amino-3-[(1S)-1-(but-2-ynoylamino)ethyl]imidazo[1,5-a]pyrazin-1-yl]-2-methoxy-N-(2-pyridyl)benzamide. This compound was prepared in an analogous manner as described for Example E-1 using Intermediate I-14 to afford the title compound (55.5 mg, 47.4%) as a yellow solid. Data: LC-MS (Method A) R$_t$: 3.68 min; m/z 470.1 (M+H)$^+$; HPLC (Method C) R$_t$: 4.76 min, 97.3% purity; $^1$H NMR (400 MHz, DMSO-d$_6$, 300 K): δ=10.51 (1H, s), 9.22 (1H, d, J=8.0 Hz), 8.39 (1H, m), 8.32 (1H, d, J=8.3 Hz), 8.07 (1H, d, J=8.0 Hz), 7.89 (1H, m), 7.56 (1H, d, J=5.1 Hz), 7.43 (1H, m), 7.40 (1H, m), 7.20 (1H, m), 7.17 (1H, d, J=4.9 Hz), 6.29 (2H, s), 5.50 (1H, m), 4.08 (3H, s), 1.96 (3H, s), 1.60 (3H, d, J=6.9 Hz).

Example 34—Preparation of 4-[8-amino-3-[(1S)-1-(but-2-ynoylamino)ethyl]imidazo[1,5-a]pyrazin-1-yl]-N-[4-(trifluoromethyl)-2-pyridyl]benzamide (E-10)

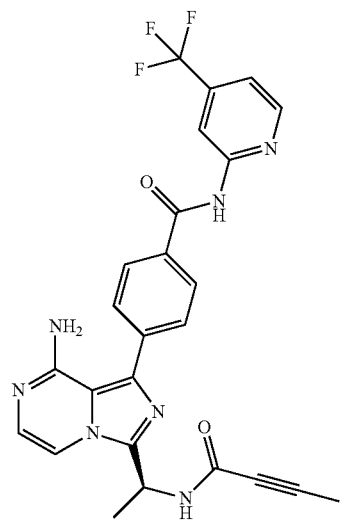 [SMILES: CC#CC(=O)N[C@@H](C)c1nc(-c2ccc(C(=O)Nc3cc(C(F)(F)F)ccn3)cc2)c2c(N)nccn12]

Preparation of 4-[8-amino-3-[(1S)-1-(but-2-ynoylamino)ethyl]imidazo[1,5-a]pyrazin-1-yl]-N-[4-(trifluoromethyl)-2-pyridyl]benzamide. This compound was prepared in an analogous manner as described for Example E-1 using Intermediate I-16 to afford the title compound (45.3 mg, 83.9%) as a light yellow solid. Data: LC-MS (Method A) $R_t$: 4.52 min; m/z 508.1 (M+H)$^+$; HPLC (Method C) $R_t$: 5.80 min, 100% purity; $^1$H NMR (400 MHz, DMSO-d$_6$, 300 K): δ=11.36 (1H, s), 9.18 (1H, d, J=8.2 Hz), 8.70 (1H, d, J=5.1 Hz), 8.58 (1H, m), 8.19 (2H, d, J=8.5 Hz), 7.77 (2H, d, J=8.5 Hz), 7.56 (1H, m), 7.53 (1H, d, J=5.1 Hz), 7.15 (1H, d, J=5.0), 6.21 (2H, s), 5.48 (1H, m), 1.95 (3H, s), 1.59 (3H, d, J=6.9 Hz).

Example 35—Preparation of 4-[8-amino-3-[(1S)-1-(but-2-ynoylamino)ethyl]imidazo[1,5-a]pyrazin-1-yl]-N-(5-methyl-2-pyridyl)benzamide (E-11)

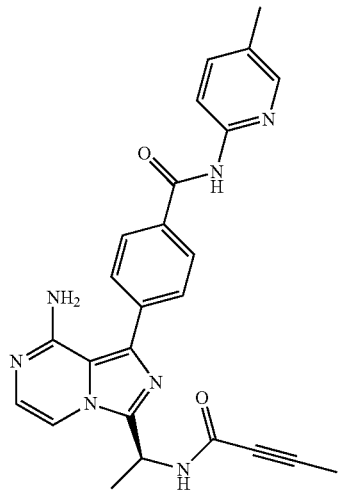 [SMILES: CC#CC(=O)N[C@@H](C)c1nc(-c2ccc(C(=O)Nc3ccc(C)cn3)cc2)c2c(N)nccn12]

Preparation of 4-[8-amino-3-[(1S)-1-(but-2-ynoylamino)ethyl]imidazo[1,5-a]pyrazin-1-yl]-N-(5-methyl-2-pyridyl)benzamide. This compound was prepared in an analogous manner as described for Example E-11 using Intermediate I-17 to afford the title compound (25.7 mg, 21.8%) as a light yellow solid. Data: LC-MS (Method A) $R_t$: 3.41 min; m/z 454.1 (M+H)$^+$; HPLC (Method C) $R_t$: 4.43 min, 99.5% purity; $^1$H NMR (400 MHz, DMSO-d$_6$, 300 K): δ=10.78 (1H, s), 9.20 (1H, d, J=8.2 Hz), 8.26 (1H, m), 8.18 (2H, d, J=8.6 Hz), 8.14 (1H, d, J=8.5 Hz), 7.76 (2H, d, J=8.5 Hz), 7.70 (1H, dd, J1=8.3 Hz, J2=2.4 Hz)), 7.54 (1H, d, J=5.1 Hz), 7.16 (1H, d, J=5.0 Hz), 6.21 (2H, s), 5.50 (1H, m), 2.31 (3H, s), 1.95 (3H, s), 1.60 (3H, d, J=7.0 Hz).

Example 36—Preparation of 4-[8-amino-3-[(1S)-1-(but-2-ynoylamino)ethyl]imidazo[1,5-a]pyrazin-1-yl]-2-methoxy-N-(5-methyl-2-pyridyl)benzamide (E-12)

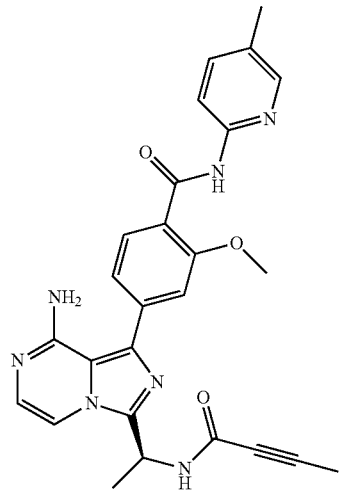 [SMILES: CC#CC(=O)N[C@@H](C)c1nc(-c2ccc(C(=O)Nc3ccc(C)cn3)c(OC)c2)c2c(N)nccn12]

Preparation of 4-[8-amino-3-[(1S)-1-(but-2-ynoylamino)ethyl]imidazo[1,5-a]pyrazin-1-yl]-2-methoxy-N-(5-methyl-2-pyridyl)benzamide. This compound was prepared in an analogous manner as described for Example E-1 using Intermediate I-18 to afford the title compound (55.4 mg, 44.9%) as a yellow solid. Data: LC-MS (Method A) $R_t$: 3.89 min; m/z 484.1 (M+H)$^+$; HPLC (Method C) $R_t$: 5.12 min, 96.2% purity; $^1$H NMR (400 MHz, DMSO-d$_6$, 300 K): δ=10.43 (1H, s), 9.21 (1H, d, J=8.0 Hz), 8.22 (2H, m), 8.07 (1H, d, J=8.0 Hz), 7.71 (1H, dd, J1=8.5 Hz, J2=2.2 Hz), 7.56 (1H, d, J=5.0 Hz), 7.41 (2H, m), 7.16 (1H, d, J=4.9 Hz), 6.29 (2H, s), 5.49 (1H, m), 4.08 (3H, s), 2.30 (3H, s), 1.96 (3H, s), 1.60 (3H, d, J=7.0 Hz).

Example 37—Preparation of 4-[8-amino-3-[(1S)-1-[[(E)-4-methoxybut-2-enoyl]amino]ethyl]imidazo[1,5-a]pyrazin-1-yl]-N-(5-methyl-2-pyridyl)benzamide (E-13)

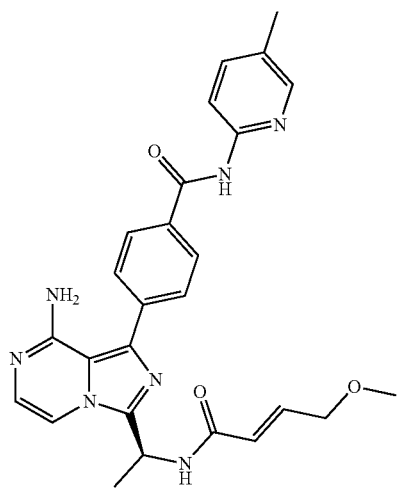 [SMILES: COC/C=C/C(=O)N[C@@H](C)c1nc(-c2ccc(C(=O)Nc3ccc(C)cn3)cc2)c2c(N)nccn12]

Preparation of 4-[8-amino-3-[(1S)-1-[[(E)-4-methoxybut-2-enoyl]amino]ethyl]imidazo[1,5-a]pyrazin-1-yl]-N-(5-methyl-2-pyridyl)benzamide. This compound was prepared in an analogous manner as described for Example E-1 using Intermediate I-17 and (E)-4-methoxybut-2-enoic acid to afford the title compound (24.0 mg, 57.6%) as a light yellow solid. Data: LC-MS (Method A) R$_t$: 3.41 min; m/z 486.2 (M+H)$^+$; HPLC (Method C) R$_t$: 4.47 min, 98.2% purity; $^1$H NMR (400 MHz, DMSO-d$_6$, 300 K): δ=10.76 (1H, s), 8.69 (1H, d, J=8.2 Hz), 8.24 (1H, m), 8.16 (2H, d, J=8.6 Hz), 8.12 (1H, d, J=8.5 Hz), 7.75 (2H, d, J=8.6 Hz), 7.68 (1H, dd, J1=8.5 Hz, J2=1.8 Hz), 7.56 (1H, d, J=5.1 Hz), 7.13 (1H, d, J=4.9), 6.69 (1H, m), 6.18 (2H, s), 6.10 (1H, m), 5.56 (1H, m), 4.02 (2H, m), 3.27 (3H, s), 2.30 (3H, s), 1.62 (3H, d, J=6.8 Hz).

Example 38—Preparation of 4-[8-amino-3-[(1S)-1-[[(E)-4-methoxybut-2-enoyl]amino]ethyl]imidazo[1,5-a]pyrazin-1-yl]-2-methoxy-N-(5-methyl-2-pyridyl)benzamide (E-14)

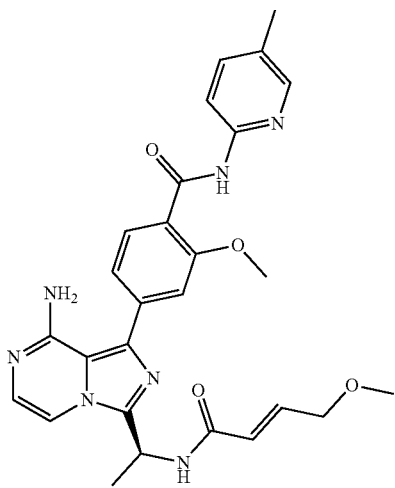 [SMILES: COC/C=C/C(=O)N[C@@H](C)c1nc(-c2ccc(C(=O)Nc3ccc(C)cn3)c(OC)c2)c2c(N)nccn12]

Preparation of 4-[8-amino-3-[(1S)-1-[[(E)-4-methoxybut-2-enoyl]amino]ethyl]imidazo[1,5-a]pyrazin-1-yl]-2-methoxy-N-(5-methyl-2-pyridyl)benzamide. This compound was prepared in an analogous manner as described for Example E-1 using Intermediate I-18 and (E)-4-methoxybut-2-enoic acid to afford the title compound (30.5 mg, 36.4%) as a light yellow solid. Data: LC-MS (Method A) R$_t$: 3.89 min; m/z 516.2 (M+H)$^+$; HPLC (Method C) R$_t$: 4.55 min, 98.8% purity; $^1$H NMR (400 MHz, DMSO-d$_6$, 300 K): δ=10.41 (1H, s), 8.71 (1H, d, J=8.7 Hz), 8.20 (2H, m), 8.05 (1H, d, J=8.0 Hz), 7.69 (1H, m), 7.58 (2H, d, J=5.0 Hz), 7.39 (2H, m), 7.13 (1H, d, J=5.0 Hz), 6.69 (1H, m), 6.26 (2H, s), 6.10 (1H, m), 5.56 (1H, m), 4.06 (3H, s), 4.02 (2H, m), 3.27 (3H, s), 2.29 (3H, s), 1.62 (3H, d, J=6.9 Hz).

Example 39—Preparation of 4-[8-amino-3-[(2S)-1-but-2-ynoylpyrrolidin-2-yl]imidazo[1,5-a]pyrazin-1-yl]-2-methoxy-N-thiazol-2-yl-benzamide (E-15)

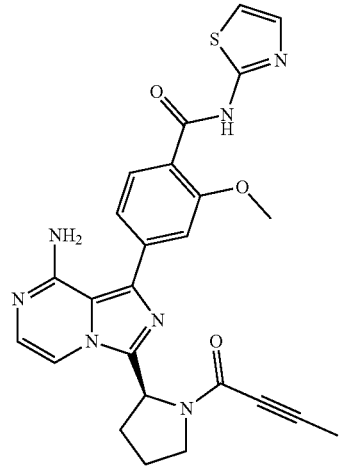 [SMILES: CC#CC(=O)N1CCC[C@H]1c1nc(-c2ccc(C(=O)Nc3nccs3)c(OC)c2)c2c(N)nccn12]

Preparation of 4-[8-amino-3-[(2S)-1-but-2-ynoylpyrrolidin-2-yl]imidazo[1,5-a]pyrazin-1-yl]-2-methoxy-N-thiazol-2-yl-benzamide. This compound was prepared in an analogous manner as described for Example E-1 to afford the title compound (12.6 mg, 21.8%) as a yellow solid. Data: LC-MS R$_t$: 4.095 min; m/z 502.3 (M+H)$^+$; HPLC (Method C) R$_t$: 5.42 min, 99.5% purity; $^1$H NMR (400 MHz, DMSO-d$_6$, 300 K): δ=11.82 (1H, s), 7.88 (2H, m), 7.82 (1H, d, J=5.1 Hz), 7.56 (1H, d, J=3.6 Hz), 7.40 (1H, dt, J1=1.3 Hz, J2=3.7 Hz), 7.36 (1H, dd, J1=1.3 Hz, J2=7.9 Hz), 7.32 (1H, d, J=3.6 Hz), 7.17 (1H, dd, J1=5.0 Hz, J2=16.1 Hz), 6.26 (2H, br d, J=27.0 Hz), 5.47-5.77 (1H, m), 4.03 (3H, d, J=2.3 Hz), 3.84 (1H, t, J=6.7 Hz), 3.62 (1H, m), 2.69 (1H, m), 2.34 (2H, m), 2.15 (1H, m), 2.03 (2H, s), 1.66 (1H, s).

Example 40—Preparation of 4-[8-amino-3-[(2S)-1-but-2-ynoylpyrrolidin-2-yl]imidazo[1,5-a]pyrazin-1-yl]-N-(5-methyl-2-pyridyl)benzamide (E-16)

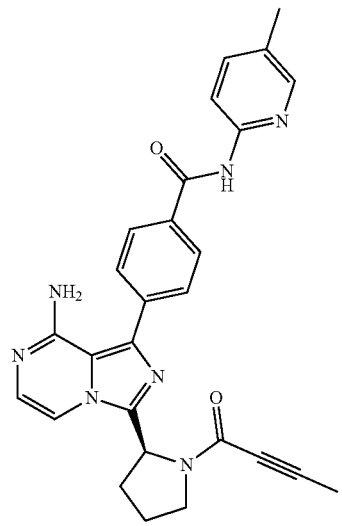 [SMILES: CC#CC(=O)N1CCC[C@H]1c1nc(-c2ccc(C(=O)Nc3ccc(C)cn3)cc2)c2c(N)nccn12]

Preparation of 4-[8-amino-3-[(2S)-1-but-2-ynoylpyrrolidin-2-yl]imidazo[1,5-a]pyrazin-1-yl]-N-(5-methyl-2-pyridyl)benzamide. This compound was prepared in an analogous manner as described for Example E-1 to afford the title compound (30.3 mg, 33.9%) as a yellow solid. Data: LC-MS $R_t$: 3.84 min; m/z 480.2 (M+H)$^+$; HPLC (Method C) $R_t$: 4.92 min, 99.9% purity; $^1$H NMR (400 MHz, DMSO-d$_6$, 300 K): δ=10.79 (1H, s), 8.26 (8.26, 1H), 8.17 (2H, dd, J1=1.6 Hz, J2=6.8 Hz), 8.14 (1H, d, J=8.4 Hz), 7.82-7.91 (1H, dd, J1=5.1 Hz, J2=22.8 Hz), 7.68-7.78 (3H, m), 7.16 (1H, dd, J1=5.0 Hz, J2=14.9 Hz), 6.35 (2H, br s), 5.47-5.77 (1H, m), 3.84 (2H, t, J=6.8 Hz), 3.61 (1H, m), 2.41 (1H, m), 2.31 (3H, s), 2.16 (1H, m), 2.03 (2H, s), 2.00 (1H, m), 1.65 (1H, s).

Example 41—Preparation of 4-[8-amino-3-[(2S)-1-but-2-ynoylpyrrolidin-2-yl]imidazo[1,5-a]pyrazin-1-yl]-2-methoxy-N-(5-methyl-2-pyridyl)benzamide (E-17)

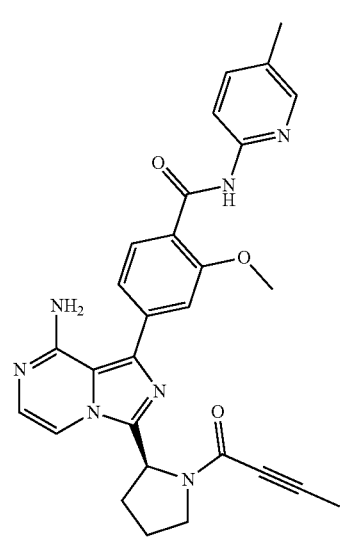 [SMILES: CC#CC(=O)N1CCC[C@H]1c1nc(-c2ccc(C(=O)Nc3ccc(C)cn3)c(OC)c2)c2c(N)nccn12]

Preparation of 4-[8-amino-3-[(2S)-1-but-2-ynoylpyrrolidin-2-yl]imidazo[1,5-a]pyrazin-1-yl]-2-methoxy-N-(5-methyl-2-pyridyl)benzamide. This compound was prepared in an analogous manner as described for Example E-1 to afford the title compound (48.3 mg, 56.0%) as a light yellow solid. Data: LC-MS $R_t$: 4.26 min; m/z 510.2 (M+H)$^+$; HPLC (Method C) $R_t$: 5.57 min, 100% purity; $^1$H NMR (400 MHz, DMSO-d$_6$, 300 K): δ=10.42 (1H, s), 8.22 (2H, q, J=2.3 Hz), 8.05 (1H, dd, J1=2.0 Hz, J2=8.1 Hz), 7.84 (1H, dd, J1=5.2 Hz, J2=25.2 Hz), 7.70 (1H, dd, J1=2.3 Hz, J2=8.3 Hz), 7.40 (2H, m), 7.17 (1H, dd, J1=4.9 Hz, J2=16.1 Hz). 6.26 (2H, br d, J=27.7 Hz), 5.46-5.78 (1H, m), 4.08 (3H, d, J=2.4 Hz), 3.84 (2H, t, J=6.4 Hz), 3.62 (1H, m), 2.38 (2H, m), 2.30 (3H, s), 2.15 (1H, m), 2.03 (2H, s), 1.66 (1H, s).

Example 42—Preparation of (S)-4-(8-amino-3-(1-(but-2-ynoyl)pyrrolidin-2-yl)imidazo[1,5-a]pyrazin-1-yl)-N-(thiazol-4-yl)benzamide (E-24)

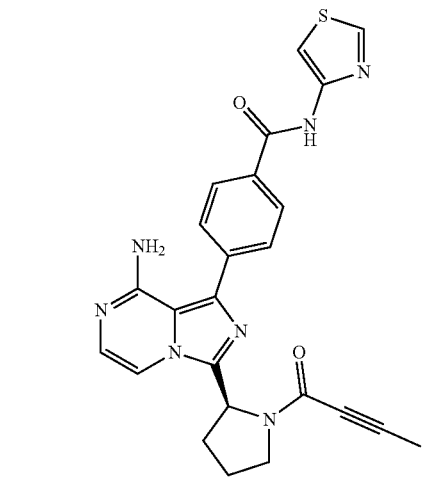 [SMILES: CC#CC(=O)N1CCC[C@H]1c1nc(-c2ccc(C(=O)Nc3cscn3)cc2)c2c(N)nccn12]

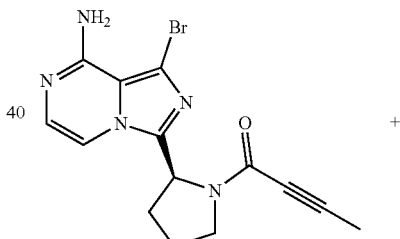

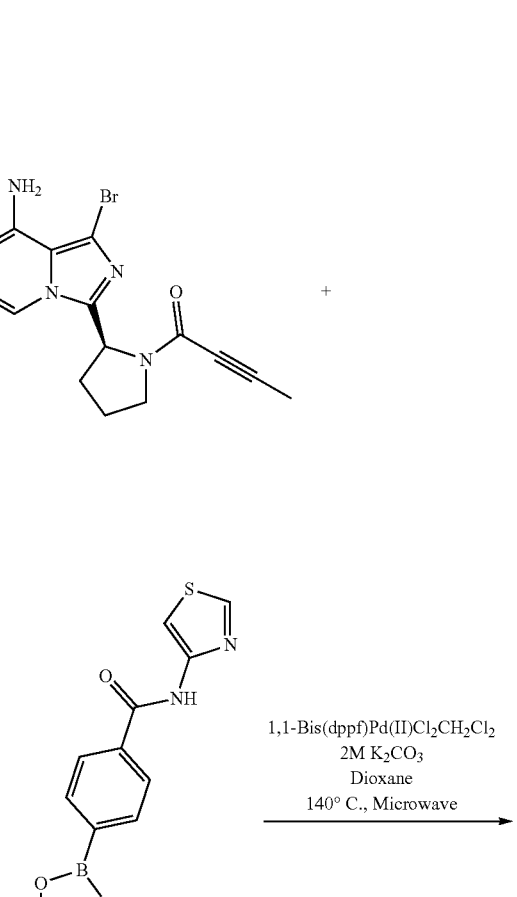

-continued

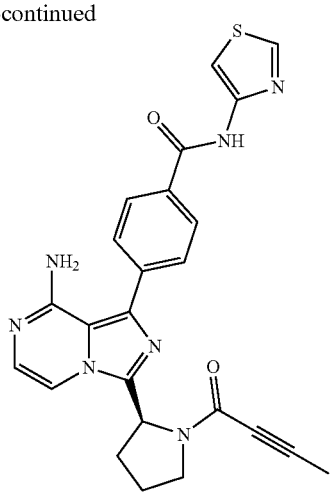

Preparation of 4-[8-amino-3-[(2S)-1-but-2-ynoylpyrrolidin-2-yl]imidazo[1,5-a]pyrazin-1-yl]-N-thiazol-4-yl-benzamide. A solution of intermediate I-23 (200 mg, 0.50 mmol, 1.0 eq), intermediate I-25 (277 mg, 0.70 mmol, 1.2 eq), 2M aqueous potassium carbonate (0.16 mL, 1.10 mmol, 2.0 eq) in 1,4-dioxane (5 mL) was degassed for 5 minutes. $PdCl_2$ $(dppf)_2$ (18 mg, 0.03 mmol, 0.05 eq) was added then the reaction mixture was again degassed for 5 minutes and stirred for 16 h at 100° C. After completion, the reaction mixture was diluted with water and extracted with ethyl acetate. The organic layer was dried over anhydrous sodium sulfate and concentrated. The residue was purified by HPLCprep purification to afford the title compound (15 mg, 6%) as a white solid. Data: LC-MS (Method G) $R_t$: 3.96 min; m/z 475.5 $(M+H)^+$. HPLC (Method H) Rt: 8.43 min, 95% purity; 1H NMR (400 MHz, DMSO-d6, 300 K): δ=11.49 (1H, s), 9.05 (1H, d, J=2.24 Hz), 8.16 (2H, dd J=2.60 Hz J=8.38 Hz), 7.89-7.84 (1H, m), 7.81 (1H, d, J=7.28 Hz), 7.74-7.71 (2H, m), 7.13 (1H, dd, J=4.92 Hz J=15.76 Hz), 6.14 (2H, bs), 5.72-5.46 (1H, m), 3.83-3.80 (1H, t), 3.60-3.58 (1H, m), 2.49-2.36 (1H, m), 2.28-2.10 (2H, m), 2.05-1.92 (3H, m), 1.62 (1H, s).

Example 43—Measurement of BTK, EGFR, and Other Enzyme Activity

BTK enzyme activity is measured using the IMAP (immobilized metal ion affinity-based fluorescence polarization) assay as outlined below.

BTK enzyme (His-BTK (Millipore catalog #14-552)), is diluted to 0.4 U/mL in KR buffer (10 mM Tris-HCl, 10 mM $MgCl_2$, 0.01% Tween-20, 0.05% $NaN_3$, 1 mM DTT, 2 mM $MnCl_2$, pH 7.2).

Serial dilutions log 10 from 2 mM to 63.2 nM of test compounds are made in 100% DMSO. The dilutions in DMSO are then diluted 50-fold in KR-buffer. Final compound concentration range in the assay ranged from 10 μM to 0.316 nM.

The assay is performed as follows: 5 μL/well of test compound in KR buffer (final DMSO concentration in the assay is 1%) is mixed with 5 l/well of 0.4 U/mL BTK enzyme (final concentration in the assay is 0.1 U/mL). Test compounds and BTK enzyme are pre-incubated 60 minutes at room temperature, before adding 5 μL/well of 200 nM Fluorescin labeled substrate peptide (Blk/Lyntide substrate, e.g. # R7188/# R7233, Molecular Devices) in KR-buffer. Final peptide substrate concentration in assay is 50 nM. The kinase assay is started by adding 5 μL/well of 20 μM ATP in KR-buffer (final ATP concentration is 5 μM ATP, Km ATP in BTK IMAP assay). Following incubation for 2 hours at room temperature the enzyme reaction is stopped by adding 40 μL/well IMAP Progressive Binding Solution (according to suppliers (Molecular Devices) protocol using 75% 1× buffer A and 25% 1× buffer B with 1:600 Progressive Binding Solution). After 60 min incubation at room temperature in the dark the FP signal is read. Fluorescence at 535 nm is measured using parallel and perpendicular filters to determine differences in rotation due to binding of the phosphorylated substrate peptide to the beads. Values are calculated as percentage of the difference in readout (ΔmPi) of the controls with and without ATP. $IC_{50}$ values are determined by curve fitting of the experimental results using Activity Base. The results are reported in Table 1.

EGFR enzyme activity is measured using the IMAP (immobilized metal ion affinity-based fluorescence polarization) assay as outlined below.

EGFR enzyme (Invitrogen catalog # PR7295B), is diluted to 2.5 μg/mL in KR buffer (10 mM Tris-HCl, 10 mM $MgCl_2$, 0.01% Tween-20, 0.1% $NaN_3$, 1 mM DTT, 2 mM $MnCl_2$, pH 7.5).

Serial dilution log 10 from 1 mM to 31.6 nM of test compounds are made in 100% DMSO. The dilutions in DMSO are then diluted 25-fold in KR-buffer of which 5 μL is used in the assay, leading to a final compound concentration range in the assay from 10 μM to 0.316 nM.

The assay is performed as follows: 5 μL/well of test compound in KR buffer (final DMSO concentration in the assay is 1%) is mixed with 5 l/well of 2.5 μg/mL EGFR enzyme (final concentration in the assay is 625 ng/mL). Test compounds and EGFR enzyme are pre-incubated 60 min at room temperature, before adding 5 μL/well of 200 nM Fluorescein labeled substrate peptide (PDGFR-tide substrate peptide RP7084, Molecular Devices) in KR-buffer. Final peptide substrate concentration in assay is 50 nM. The kinase assay is started by adding 5 μL/well of 8 μM ATP in KR-buffer (final ATP concentration is 2 μM, Km ATP in EGFR IMAP assay). Following incubation for 60 min at room temperature in the dark the enzyme reaction is stopped by adding 40 μL/well IMAP Progressive Binding Solution (according to suppliers (Molecular Devices) protocol using 20% 1× buffer A and 80% 1× buffer B with 600× diluted beads). After 60 min incubation at room temperature in the dark the FP signal is read. Fluorescence at 535 nm is measured using parallel and perpendicular filters to determine differences in rotation due to binding of the phosphorylated substrate peptide to the beads. Values are calculated as percentage of the difference in readout (ΔmPi) of the controls with and without ATP. $IC_{50}$ values are determined by curve fitting of the experimental results using GraphPad Prism6. The results are reported in Table 1.

ITK enzyme activity is measured using the IMAP (immobilized metal ion affinity-based fluorescence polarization) assay as outlined below.

ITK enzyme (Millipore #14-660M) is diluted to 0.2 U/mL in KR buffer (10 mM Tris-HCl, 10 mM $MgCl_2$, 0.01% Tween-20, 0.1% $NaN_3$, 1 mM DTT, 2 mM $MnCl_2$, pH 7.5)

Serial dilutions log 10 from 2 mM to 63.2 nM of test compounds are made in 100% DMSO. The dilutions in DMSO are then diluted 50-fold in KR-buffer. Final compound concentration range in the assay ranged from 10 μM to 0.316 nM.

The assay is performed as follows: 5 μL/well of test compound in KR buffer (final DMSO concentration in the assay is 1%) is mixed with 5 µL/well of 0.2 U/mL ITK enzyme (final concentration in the assay is 0.05 U/mL (8.4 nM)). Test compounds and ITK enzyme are pre-incubated 60 minutes at room temperature, before adding 5 µL/well of 200 nM Fluorescin labeled substrate peptide (Blk/Lyntide substrate # R8124, Molecular Devices) in KR-buffer. Final peptide substrate concentration in assay is 50 nM. The kinase assay is started by adding 5 µL/well of 20 µM ATP in KR-buffer (final ATP concentration is 5 µM ATP, Km ATP in ITK IMAP assay). Following incubation for 2 hours at room temperature the enzyme reaction is stopped by adding 40 µL/well IMAP Progressive Binding Solution (according to suppliers (Molecular Devices) protocol using 60% 1× buffer A and 40% 1× buffer B with 800× diluted beads (Progressive Binding System, Molecular Devices # R8124). After 60 min incubation at room temperature in the dark the FP signal is read. Fluorescence at 535 nm is measured using parallel and perpendicular filters to determine differences in rotation due to binding of the phosphorylated substrate peptide to the beads. Values are calculated as percentage of the difference in readout (ΔmPi) of the controls with and without ATP. $IC_{50}$ values are determined by curve fitting of the experimental results using Activity Base.

TEC enzyme activity is measured using the IMAP (immobilized metal ion affinity-based fluorescence polarization) assay as outlined below.

TEC enzyme (Millipore #14-801M), is diluted to 2 U/mL in KR buffer (10 mM Tris-HCl, 10 mM $MgCl_2$, 0.01% Tween-20, 0.1% $NaN_3$, 1 mM DTT, 2 mM $MnCl_2$, pH 7.5).

Serial dilutions log 10 from 2 mM to 63.2 nM of test compounds are made in 100% DMSO. The dilutions in DMSO are then diluted 50-fold in KR-buffer. Final compound concentration range in the assay ranged from 10 µM to 0.316 nM.

The assay is performed as follows: 5 µL/well of test compound in KR buffer (final DMSO concentration in the assay is 1%) is mixed with 5 µL/well of 2 U/mL TEC enzyme (final concentration in the assay is 0.5 U/mL (6.3 nM)). Test compounds and TEC enzyme are pre-incubated 60 minutes at room temperature, before adding 5 µL/well of 200 nM Fluorescin labeled substrate peptide (Blk/Lyntide substrate # R7188, Molecular Devices) in KR-buffer. Final peptide substrate concentration in assay is 50 nM. The kinase assay is started by adding 5 µL/well of 20 µM ATP in KR-buffer (final ATP concentration is 5 µM ATP, Km ATP in TEC IMAP assay). Following incubation for 2 hours at room temperature the enzyme reaction is stopped by adding 40 µL/well IMAP Progressive Binding Solution (according to suppliers (Molecular Devices) protocol using 60% 1× buffer A and 40% 1× buffer B with 800× diluted beads (Progressive Binding System, Molecular Devices # R8124). After 60 min incubation at room temperature in the dark the FP signal is read. Fluorescence at 535 nm is measured using parallel and perpendicular filters to determine differences in rotation due to binding of the phosphorylated substrate peptide to the beads. Values are calculated as percentage of the difference in readout (ΔmPi) of the controls with and without ATP. $IC_{50}$ values are determined by curve fitting of the experimental results using Activity Base.

TXK enzyme activity is measured using the IMAP (immobilized metal ion affinity-based fluorescence polarization) assay as outlined below.

TXK enzyme (Millipore #14-761), is diluted to 2.5 U/mL in KR buffer (10 mM Tris-HCl, 10 mM $MgCl_2$, 0.01% Tween-20, 0.1% $NaN_3$, 1 mM DTT, 2 mM $MnCl_2$, pH 7.5).

Serial dilutions log 10 from 2 mM to 63.2 nM of test compounds are made in 100% DMSO. The dilutions in DMSO are then diluted 50-fold in KR-buffer. Final compound concentration range in the assay ranged from 10 µM to 0.316 nM.

The assay is performed as follows: 5 µL/well of test compound in KR buffer (final DMSO concentration in the assay is 1%) is mixed with 5 µL/well of 2.5 U/mL TXK enzyme (final concentration in the assay is 0.625 U/mL (4.4 nM)). Test compounds and TXK enzyme are pre-incubated 60 minutes at room temperature, before adding 5 µL/well of 200 nM Fluorescin labeled substrate peptide (Blk/Lyntide substrate # R7188, Molecular Devices) in KR-buffer. Final peptide substrate concentration in assay is 50 nM. The kinase assay is started by adding 5 µL/well of 4 µM ATP in KR-buffer (final ATP concentration is 1 µM ATP, Km ATP in TXK IMAP assay). Following incubation for 2 hours at room temperature the enzyme reaction is stopped by adding 40 µL/well IMAP Progressive Binding Solution (according to suppliers (Molecular Devices) protocol using 60% 1× buffer A and 40% 1× buffer B with 800× diluted beads (Progressive Binding System, Molecular Devices). After 60 min incubation at room temperature in the dark the FP signal is read. Fluorescence at 535 nm is measured using parallel and perpendicular filters to determine differences in rotation due to binding of the phosphorylated substrate peptide to the beads. Values are calculated as percentage of the difference in readout (ΔmPi) of the controls with and without ATP. $IC_{50}$ values are determined by curve fitting of the experimental results using Activity Base.

BMX enzyme activity is measured using the IMAP (immobilized metal ion affinity-based fluorescence polarization) assay as outlined below.

BMX enzyme (Millipore #14-499M), is diluted to 0.5 U/mL in KR buffer (10 mM Tris-HCl, 10 mM $MgCl_2$, 0.01% Tween-20, 0.1% $NaN_3$, 1 mM DTT, 2 mM $MnCl_2$, pH 7.5)

Serial dilutions log 10 from 2 mM to 63.2 nM of test compounds are made in 100% DMSO. The dilutions in DMSO are then diluted 50-fold in KR-buffer. Final compound concentration range in the assay ranged from 10 µM to 0.316 nM.

The assay is performed as follows: 5 µL/well of test compound in KR buffer (final DMSO concentration in the assay is 1%) is mixed with 5 µL/well of 0.5 U/mL BMX enzyme (final concentration in the assay is 0.125 U/mL (4.5 nM)). Test compounds and BMX enzyme are pre-incubated 60 minutes at room temperature, before adding 5 µL/well of 200 nM Fluorescin labeled substrate peptide (Blk/Lyntide substrate # R7188, Molecular Devices) in KR-buffer. Final peptide substrate concentration in assay is 50 nM. The kinase assay is started by adding 5 µL/well of 20 µM ATP in KR-buffer (final ATP concentration is 5 µM ATP, Km ATP in BMX IMAP assay). Following incubation for 2 hours at room temperature the enzyme reaction is stopped by adding 40 µL/well IMAP Progressive Binding Solution (according to suppliers (Molecular Devices) protocol using 60% 1× buffer A and 40% 1× buffer B with 800× diluted beads (Progressive Binding System, Molecular Devices # R8124). After 60 min incubation at room temperature in the dark the FP signal is read. Fluorescence at 535 nm is measured using parallel and perpendicular filters to determine differences in rotation due to binding of the phosphorylated substrate peptide to the beads. Values are calculated as percentage of the difference in readout (ΔmPi) of the controls with and without ATP. $IC_{50}$ values are determined by curve fitting of the experimental results using Activity Base.

Example 44—Human Peripheral Blood Mononuclear Cell (PBMC) CD69 Assay

Whole blood was collected in heparin-coated Vacutainer tubes (BD Biosciences, San Jose, Calif.) and used for isolation of PBMCs using Ficoll-Hypaque (Pharmacia, Uppsala, Sweden). Isolated PBMCs were cryopreserved in 90% FCS/10% DMSO until later use.

Cells from cryogenic storage were thawed in a 37° C. water bath, diluted with RPMI/1% FCS, washed 2 times, and then plated at $1 \times 10^5$ cells per well in RPMI/10% FCS.

Serial dilutions log 10 from 10 mM to 316 nM of test compounds are made in 100% DMSO, followed by a 100-fold dilution into RPMI/1% FCS. For each well, 10 µL was then transferred to the deep well plate containing 90 µL of PBMC cells. Final compound concentration range in the assay ranged from 10 µM to 0.316 nM, with a final DMSO concentration of 0.1%. PBMCs are then incubated for 2 h at 37° C. in presence or absence of test compounds, prior to stimulation with goat F(ab')2 anti-IgM (Southern Biotech, #2022-14, final concentration in assay 5 µg/mL) for 18 hours.

Following stimulation with anti-IgM, PBMCs were incubated on ice for 30 min with anti-CD69-FITC, anti-CD19-BV421 (BD Biosciences #555530 and #562440, respectively) and 7AAD (Life Technologies # A1310). Flow cytometry was performed and fluorescence values were obtained from the CD69-FITC channel in CD19+ gated life B cells. $EC_{50}$ values are determined by curve fitting of the experimental results using GraphPad Prism.

TABLE 1

Activity data for BTK inhibitors.

| Compound | BTK (nM) | EGFR WT (nM) | TEC (nM) | Txk (nM) | ITK (nM) | ErbB 2[1] (nM) | ErbB 4[1] (nM) | Blk[1] (nM) | Bmx (nM) | Jak3[1] (nM) | PBMC Assay (CD69) $EC_{50}$ (nM) |
|---|---|---|---|---|---|---|---|---|---|---|---|
| (structure 1) | 1.6 | >1000 | 2.2 | 2.0 | >1000 | | | | 3.1 | | 1.3 |
| (structure 2) | 2.5 | >1000 | 3.9 | 16 | >1000 | >1000 | 99 | 489 | 14 | >1000 | 3.7 |

TABLE 1-continued

Activity data for BTK inhibitors.

| Compound | IMAP (IC$_{50}$) | | | | | | | | | | PBMC Assay (CD69) EC$_{50}$ (nM) |
|---|---|---|---|---|---|---|---|---|---|---|---|
| | BTK (nM) | EGFR WT (nM) | TEC (nM) | Txk (nM) | ITK (nM) | ErbB 2[1) (nM) | ErbB 4[1) (nM) | Blk[1) (nM) | Bmx (nM) | Jak3[1) (nM) | |
| | 2.0 | >1000 | 2.5 | 3.0 | >1000 | | | | 4.2 | | 2.4 |
| | 3.9 | >1000 | 7.2 | 7.1 | >1000 | | | | 12 | | 11 |
| | 4.2 | >1000 | 4.5 | 12 | >1000 | | | | 16 | | 3.7 |

TABLE 1-continued
Activity data for BTK inhibitors.
| Compound | IMAP (IC$_{50}$) | | | | | | | | | | PBMC Assay (CD69) EC$_{50}$ (nM) |
|---|---|---|---|---|---|---|---|---|---|---|---|
| | BTK (nM) | EGFR WT (nM) | TEC (nM) | Txk (nM) | ITK (nM) | ErbB 2[1] (nM) | ErbB 4[1] (nM) | Blk[1] (nM) | Bmx (nM) | Jak3[1] (nM) | |
| | 6.7 | >1000 | 3.8 | 11 | >1000 | | | | 11 | | 5.2 |
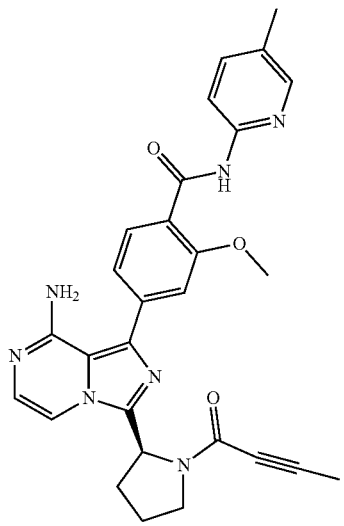 [SMILES: CC#CC(=O)N1CCC[C@H]1c1nc(-c2ccc(C(=O)Nc3ccc(C)cn3)c(OC)c2)c2c(N)nccn12]
| | | | | | | | | | | |
|---|---|---|---|---|---|---|---|---|---|---|
| 1.6 | 549 | 2.0 | 2.1 | 287 | | | | 2.9 | | 1.0 |
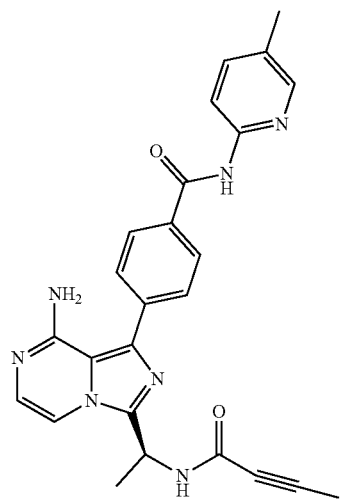 [SMILES: CC#CC(=O)N[C@@H](C)c1nc(-c2ccc(C(=O)Nc3ccc(C)cn3)cc2)c2c(N)nccn12]

TABLE 1-continued

Activity data for BTK inhibitors.

| Compound | IMAP (IC$_{50}$) | | | | | | | | | PBMC |
|---|---|---|---|---|---|---|---|---|---|---|
| | BTK (nM) | EGFR WT (nM) | TEC (nM) | Txk (nM) | ITK (nM) | ErbB 2[1) (nM) | ErbB 4[1) (nM) | Blk[1) (nM) | Bmx (nM) | Jak3[1) (nM) | Assay (CD69) EC$_{50}$ (nM) |
| *structure* | 1.9 | >1000 | 1.9 | 1.7 | >1000 | | | | 2.4 | | 1.3 |
| *structure* | 1.8 | 354 | 3.1 | 3.9 | 254 | | | | 4.5 | | 1.7 |
| *structure* | 2.1 | 123 | 5.0 | 3.7 | >1000 | | | | 7.5 | | 1.9 |

TABLE 1-continued
Activity data for BTK inhibitors.
| Compound | IMAP (IC$_{50}$) | | | | | | | | | | PBMC |
| | BTK (nM) | EGFR WT (nM) | TEC (nM) | Txk (nM) | ITK (nM) | ErbB 2[1) (nM) | ErbB 4[1) (nM) | Blk[1) (nM) | Bmx (nM) | Jak3[1) (nM) | Assay (CD69) EC$_{50}$ (nM) |
| --- | --- | --- | --- | --- | --- | --- | --- | --- | --- | --- | --- |
| 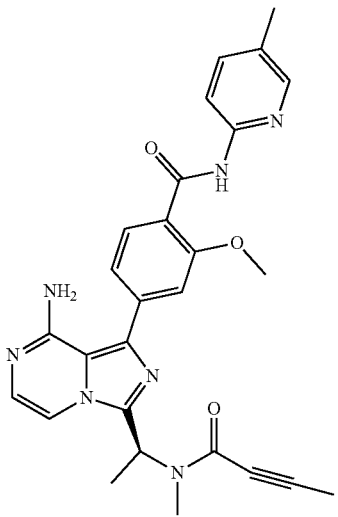 [SMILES: CC#CC(=O)N(C)[C@@H](C)c1nc(-c2ccc(C(=O)Nc3ccc(C)cn3)c(OC)c2)c2c(N)nccn12] | 5.1 | >1000 | 4.6 | 5.1 | >1000 | | | | 6.8 | | 5.1 |
| 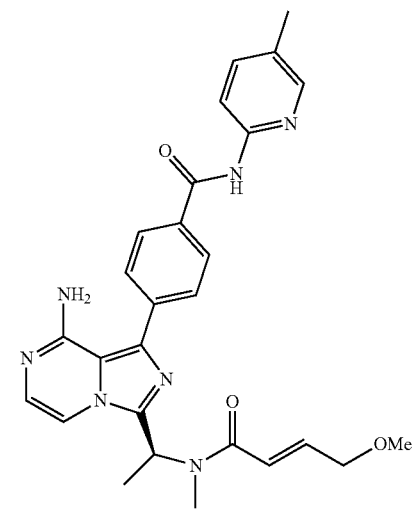 [SMILES: COC/C=C/C(=O)N(C)[C@@H](C)c1nc(-c2ccc(C(=O)Nc3ccc(C)cn3)cc2)c2c(N)nccn12] | 11 | >1000 | 3.8 | 14 | >1000 | | | | 15 | | 3.5 |

TABLE 1-continued
Activity data for BTK inhibitors.
| Compound | IMAP (IC$_{50}$) | | | | | | | | | | PBMC Assay (CD69) EC$_{50}$ (nM) |
|---|---|---|---|---|---|---|---|---|---|---|---|
| | BTK (nM) | EGFR WT (nM) | TEC (nM) | Txk (nM) | ITK (nM) | ErbB 2[1) (nM) | ErbB 4[1) (nM) | Blk[1) (nM) | Bmx (nM) | Jak3[1) (nM) | |
| | 2.4 | 360 | 1.9 | 1.5 | 478 | | | | 2.9 | | 4.2 |
| | 1.8 | 327 | 2.6 | 1.8 | 119 | | | | 1.9 | | 0.70 |
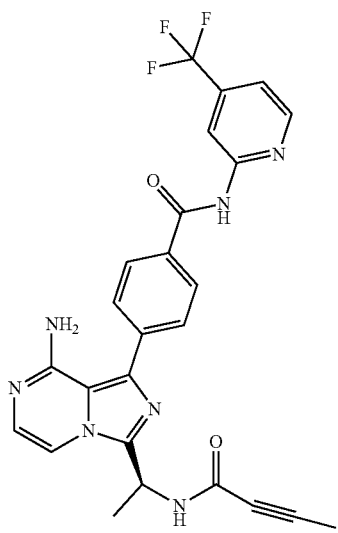 [SMILES: CC#CC(=O)N[C@@H](C)c1nc(-c2ccc(C(=O)Nc3cc(C(F)(F)F)ccn3)cc2)c2c(N)nccn12]

TABLE 1-continued

Activity data for BTK inhibitors.

| Compound | IMAP (IC$_{50}$) | | | | | | | | | | PBMC Assay (CD69) EC$_{50}$ (nM) |
|---|---|---|---|---|---|---|---|---|---|---|---|
| | BTK (nM) | EGFR WT (nM) | TEC (nM) | Txk (nM) | ITK (nM) | ErbB 2[1] (nM) | ErbB 4[1] (nM) | Blk[1] (nM) | Bmx (nM) | Jak3[1] (nM) | |
| | 2.2 | >1000 | 3.4 | 4.7 | >1000 | | | | 3.5 | | 1.4 |
| | 3.9 | >1000 | 1.6 | 2.7 | >1000 | | | | 3.0 | | 1.9 |

TABLE 1-continued
Activity data for BTK inhibitors.
| Compound | IMAP (IC$_{50}$) | | | | | | | | | | PBMC |
|---|---|---|---|---|---|---|---|---|---|---|---|
| | BTK (nM) | EGFR WT (nM) | TEC (nM) | Txk (nM) | ITK (nM) | ErbB 2[1] (nM) | ErbB 4[1] (nM) | Blk[1] (nM) | Bmx (nM) | Jak3[1] (nM) | Assay (CD69) EC$_{50}$ (nM) |
| 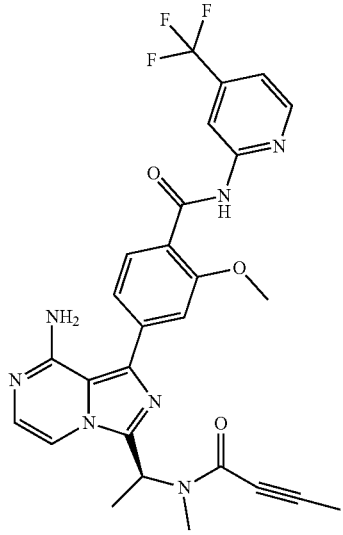 [SMILES: CC#CC(=O)N(C)[C@@H](C)c1nc(-c2ccc(C(=O)Nc3cc(C(F)(F)F)ccn3)c(OC)c2)c2c(N)nccn12] | 3.5 | >1000 | 7.0 | 13 | >1000 | | | | 7.9 | | 2.7 |
| 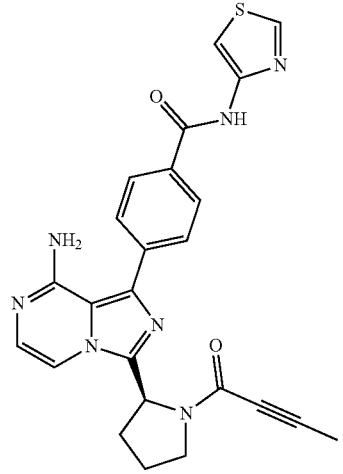 [SMILES: CC#CC(=O)N1CCC[C@H]1c1nc(-c2ccc(C(=O)Nc3cscn3)cc2)c2c(N)nccn12] | 6.3 | | 6.2 | 33.5 | >1000 | | | | 97.4 | | 9.5 |
[1]Values obtained from Z-LYTE assay performed at Life Technologies (Bleiswijk, Netherlands).

We claim:
1. A compound of Formula (I) having the structure:
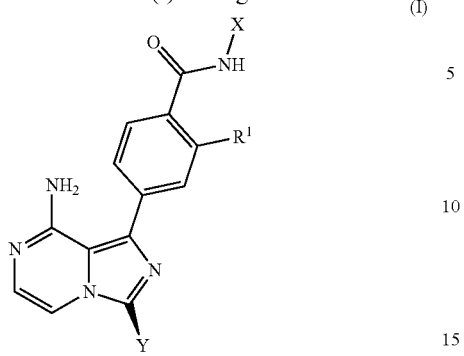
(I)
or a pharmaceutically acceptable salt thereof, wherein:
R¹ is hydrogen or methoxy, wherein methoxy is optionally substituted with one or two fluoro;
X is:
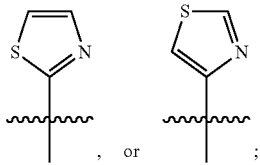 [SMILES: *c1nccs1 ; *c1cscn1]
, or ;
Y is:
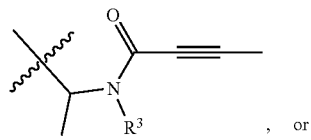
, or
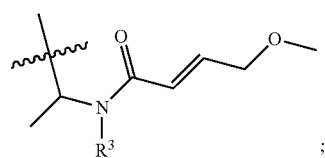
;
R³ is H or methyl.
2. A pharmaceutical composition comprising a compound of claim 1 and at least one pharmaceutically acceptable excipient.
* * * * *